(12) United States Patent
Alhamadsheh et al.

(10) Patent No.: US 10,596,269 B2
(45) Date of Patent: *Mar. 24, 2020

(54) DELIVERING ENHANCED ACTIVE AGENTS

(71) Applicant: Mamoun M Alhamadsheh, Stockton, CA (US)

(72) Inventors: Mamoun M. Alhamadsheh, Stockton, CA (US); Miki S. Park, Stockton, CA (US); William K. Chan, Elk Grove, CA (US); Xiaoling Li, Dublin, CA (US); Sravan C. Penchala, Stockton, CA (US); Mark R. Miller, Stockton, CA (US)

(73) Assignee: Mamoun M. Alhamadsheh, Stockton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/436,412

(22) Filed: Jun. 10, 2019

(65) Prior Publication Data

US 2019/0365912 A1     Dec. 5, 2019

Related U.S. Application Data

(63) Continuation of application No. 16/193,407, filed on Nov. 16, 2018, now Pat. No. 10,363,318, which is a continuation of application No. 15/446,212, filed on Mar. 1, 2017, now Pat. No. 10,172,959, which is a continuation of application No. 14/804,024, filed on Jul. 20, 2015, now abandoned.

(60) Provisional application No. 62/037,592, filed on Aug. 14, 2014.

(51) Int. Cl.
| | |
|---|---|
| *A61K 47/64* | (2017.01) |
| *A61K 31/4745* | (2006.01) |
| *A61K 49/00* | (2006.01) |
| *A61K 31/00* | (2006.01) |
| *A61K 47/54* | (2017.01) |
| *A61K 38/00* | (2006.01) |
| *C07D 231/12* | (2006.01) |

(52) U.S. Cl.
CPC .............. *A61K 47/64* (2017.08); *A61K 31/00* (2013.01); *A61K 31/4745* (2013.01); *A61K 47/545* (2017.08); *A61K 49/0052* (2013.01); *A61K 38/00* (2013.01); *C07D 231/12* (2013.01)

(58) Field of Classification Search
CPC .... A61K 47/64; A61K 31/00; A61K 31/4745; A61K 47/545; A61K 49/0052; A61K 38/00; C07D 231/12
See application file for complete search history.

(56) References Cited

U.S. PATENT DOCUMENTS

| | | |
|---|---|---|
| RE28,819 E | 5/1976 | Thompson |
| 4,171,365 A | 10/1979 | Diana et al. |
| 4,232,161 A | 11/1980 | Diana et al. |
| 4,234,725 A | 11/1980 | Diana et al. |
| 4,255,329 A | 3/1981 | Ullman |
| 4,261,928 A | 4/1981 | Diana et al. |
| 4,328,245 A | 5/1982 | Yu et al. |
| 4,358,603 A | 11/1982 | Yu |
| 4,409,239 A | 10/1983 | Yu |
| 4,410,545 A | 10/1983 | Yu et al. |
| 4,522,811 A | 6/1985 | Eppstein et al. |
| 4,657,914 A | 4/1987 | Bernardi et al. |
| 4,668,640 A | 5/1987 | Wang et al. |
| 5,315,015 A | 5/1994 | Hui et al. |
| 5,413,990 A | 5/1995 | Haviv et al. |
| 5,521,202 A | 5/1996 | Yano et al. |
| 5,709,874 A | 1/1998 | Hanson et al. |
| 5,714,142 A | 2/1998 | Blaney et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |

(Continued)

FOREIGN PATENT DOCUMENTS

| | | |
|---|---|---|
| SU | 1824398 | 4/1991 |
| WO | WO 95/12815 | 5/1995 |

(Continued)

OTHER PUBLICATIONS

U.S. Appl. No. 62/037,592, Alhamadsheh, et al.—related case, filed Aug. 14, 2014.

(Continued)

*Primary Examiner* — Michael G. Hartley
*Assistant Examiner* — Leah H Schlientz
(74) *Attorney, Agent, or Firm* — Brian S. Boyer; Syndicated Law, PC

(57) ABSTRACT

The teachings provide methods of delivering active agents that are conjugated with delivery systems that increase the half-life, and reduce the immunogenicity, of the active agents. Delivery systems and methods of making and using the delivery systems are also provided. The delivery systems have (i) a ligand that is selective for an endogeneous plasma protein in the serum of a subject; and, (ii) a linker configured for operatively attaching the ligand covalently to an active agent to increase the half-life of the active agent in the serum.

20 Claims, 20 Drawing Sheets
Specification includes a Sequence Listing.

(56) References Cited

U.S. PATENT DOCUMENTS

| | | | |
|---|---|---|---|
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 7,214,695 | B2 | 5/2007 | Kelly et al. |
| 7,459,567 | B2 | 12/2008 | Fobare et al. |
| 7,560,488 | B2 | 7/2009 | Kelly et al. |
| 7,598,269 | B2 | 10/2009 | Kong et al. |
| 7,943,652 | B2 | 5/2011 | Shultz et al. |
| 8,143,424 | B2 | 3/2012 | Chhipa et al. |
| 8,378,118 | B2 | 2/2013 | Chhipa et al. |
| 8,877,795 | B2 | 11/2014 | Graef et al. |
| 10,172,959 | B2 | 1/2019 | Alhamadsheh et al. |
| 10,363,318 | B2 | 7/2019 | Alhamadsheh et al. |
| 2003/0032803 | A1 | 2/2003 | Duan et al. |
| 2003/0195154 | A1 | 10/2003 | Walker et al. |
| 2006/0160796 | A1 | 7/2006 | Pfahl et al. |
| 2011/0045587 | A1 | 2/2011 | Sullivan et al. |
| 2014/0179751 | A1 | 6/2014 | Graef et al. |
| 2016/0045609 | A1 | 2/2016 | Alhamadsheh et al. |

FOREIGN PATENT DOCUMENTS

| | | |
|---|---|---|
| WO | WO 98/27972 | 7/1998 |
| WO | WO 02/059621 | 1/2002 |
| WO | WO 2004/056315 | 7/2004 |
| WO | WO 2004/096808 | 11/2004 |
| WO | WO 2005/054179 A2 | 6/2005 |
| WO | WO 2006/009826 | 1/2006 |
| WO | WO 2008/016811 | 2/2008 |
| WO | WO 2008/077597 | 7/2008 |
| WO | WO 2008/141020 | 11/2008 |
| WO | WO 2008/145616 A1 | 12/2008 |
| WO | WO 2008/154241 | 12/2008 |
| WO | WO 2009/148961 | 12/2009 |
| WO | WO 2010/010190 | 1/2010 |
| WO | WO 2010/030592 | 3/2010 |
| WO | WO 2011/075210 | 6/2011 |
| WO | WO 2011/140333 | 11/2011 |

OTHER PUBLICATIONS

PCT/US2013/076213, The Board of Trustees of the Leland Stanford Junior University, Jun. 26, 2014.
International Search Report PCT/US2013/076213, The Board of Trustees of the Leland Stanford Junior University, dated Jun. 26, 2014.
PCT/US2015/041189, Alhamadsheh, et al.—related case, Jul. 20, 2015.
International Search Report PCT/US2015/041189, Alhamadsheh, et al.—related case, dated Jul. 20, 2015.
Written Opinion PCT/US2015/041189, Alhamadsheh, et al.—related case, dated Jul. 20, 2015.
European search report for EP 15831770, dated Jun. 21, 2017, Alhamadsheh, Mamoun, M., et al.—related case.
Adamski-Werner, S.L., et al. Diflunisal analogues stabilize the native state of transthyretin. J. Med. Chem. 47(2): 355-374 (2004).
Ahlskog, J.K.J., et al. In vivo targeting of tumor-associated carbonic anhydrases using acetazolamide derivatives. Bioorganic & Medicinal Chemistry Lettters 19: 4851-4856 (2009).
Alconcel, S.N.S., et al. FDA-approved poly(ethylene glycol)-protein conjugate drugs. Polymer Chemistry 2: 1442-1448 (2011).
Aldred, A.R., et al. The cerebral expression of plasma protein genes in different species. Comp. Biochem. Physiol. B Biochem. Mol. Biol. 111(1): 1-15.
Alhamadsheh, M.M., et al. A biomimetic approach for enhancing the in vivo half-life of peptides. Nat. Chem. Bio. DOI: 10.1038/NCHEMBIO.1907 (2015).
Alhamadsheh, M.M., et al. Design, total synthesis, and evaluation of novel open-chain epothilone analogues. Org. Lett. 8(4): 685-688 (2006).
Alhamadsheh, M.M., et al. Alkyl-CoA disulfides as inhibitors and mechanistic probes for FabH enzymes. Chem. Biol. 14(5): 513-524 (2007).
Alhamadsheh, M.M., et al. Modular polyketide synthases and cis bond double formation: establishment of activated cis-3-cyclohexylpropenoic acid as the diketide intermediate in phoslactomycin biosynthesis. Journ Amer. Chem. Soc. 129(7): 1910-1911 (2007).
Alhamadsheh, M.M., et al. Synthesis and biological evaluation of thiazolidine-2-one 1,1-dioxide as inhibitors of *Escherichia coli* beta-ketoacyl-ACP-synthase III (FabH). Bioorg. Med. Chem. Lett. 17(4): 879-883 (2007).
Alhamadsheh, M.M., et al. Synthesis and biological evaluation of novel sulfonyl-naphthalene-1,4-diols as FabH inhibitors. Bioorg. Med. Chem. Lett. 18(24): 6402-6405 (2008).
Alhamadsheh, M.M., et al. Total synthesis and selective activity of a new class of conformationally restrained epothilones. Chemistry—A European Journal 14(2): 570-581 (2008).
Alhamadsheh, M.M., et al. Potent kinetic stabilizers that prevent transthyretin-mediated cardiomyocyte proteotoxicity. Sci. Transl. Med. 3(97): 1-17 (2011).
Almeida, M.R., et al. Small transthyretin (TTR) ligands as possible therapeutic agents in TTR amyloidoses. Curr. Drug Targets CNS Neurol. Disord. 4(5): 587-596 (2005).
Anderes, K.L., et al. Biological characterization of a novel, orally active small molecule gonadotropin-releasing hormone (GnRH) antagonist using castrated and intact rats. Journal of Pharmacology and Experimental Therapeutics 305(2): 688-695 (2003).
Arkin, M.R., et al. Small-molecule inhibitors of protein-protein interactions: progressing towards the dream. Nat. Rev. Drug Discov. 3(4): 301-317 (2004).
Barelli, H., et al. Role of endopeptidase 3.4.24.16 in the catabolism of neurotensin, in vivo, in the vascularly perfused dog ileum. Br. Journ. Pharmacol. 112: 127-132 (1994).
Bartalena, L., et al. Thyroid hormone transporter proteins. Clin. Lab. Med. 13(3): 583-598 (1993).
Bendele, A., et al. Short communication: renal tubular vacuolation in animals treated with polyethylene-glycol-conjugated proteins. Toxicol. Sci. 42: 152-157 (1998).
Blake, C.C., et al. Structure of prealbumin: secondary, tertiary and quaternary interactions determined by Fourier refinement at 1.8 A. J. Mol. Biol. 121(3): 339-356 (1978).
Bleiberg-Daniel, F., et al. Failure of tryptophan deficiency to reduce specifically serum levels of transthyretin or albumin in rats. Journ. Nutr. 120(12): 1610-1616 (1990).
Boohaker, R.J., et al. The use of therapeutic peptides to target and to kill cancer cells. Current Medicinal Chemistry 19(22): 3794-3804 (2012).
Borgulya, J., et al. Catechol-O-methyltransferase-inhibiting pyrocatechol derivatives: synthesis and structure-activity studies. Helvetica Chimica Acta 72(5): 952-968 (1989).
Bourgault, S., et al. Mechanisms of transthyretin cardiomyocyte toxicity inhibition by resveratrol analogs. Biochem. Biophys. Res. Comm. 410(4): 707-713 (2011).
Buxbaum, J.N., et al. Transthyretin protects alzheimer's mice from the behavioral and biochemical effects of A(beta) toxicity. Proc. Nat. Acad. Sci. 105(7): 2681-2686 (2008).
Buxbaum, J.N., et al. Significance of the amyloidogenic transthyretin Val 122 Ile allele in African Americans in the arteriosclerosis risk in communities (ARIC) and cardiovascular health (CHS) studies. American Heart Journal 159(5): 864-870 (2010).
Cativiela, C., et al. Synthesis of 3-Substituted Pentane-2,4-diones: Valuable Intermediates for Liquid Crystals. J. Org. Chem. 60(10): 3074-83 (1995).

(56) References Cited

OTHER PUBLICATIONS

Chan, R.L. and Nerenberg, C.A. Pharmacokinetics and metabolism of LHRH analogs in LHRH and Its Analogs. Springer: 577-593 (1987).
Chang, L., et al. Evolution of thyroid hormone binding by transthyretins in birds and mammals. Eur. Journ. Biochem. 259(1-2): 534-542 (1999).
Choi, S., et al. Accelerated A(beta) deposition in APPswe/PS1(delta)E9 mice with hemizygous deletions of TTR (transthyretin). Journ. Neuroscience 27(26):7006-7010 (2007).
Choi, S., et al. Chemoselective small molecules that covalently modify one lys in a non-enzyme protein in plasma. Nat. Chem. Biol. 6(2): 133-139 (2010).
Choi, S. and Kelly, J.W. A competition assay to identify amyloidogenesis inhibitors by monitoring the fluorescence emitted by the covalent attachment of a stilbene derivative to transthyretin. Bioorg. Med. Chem. 19(4): 1505-1514.
Choi, J.H., et al. Antidiabetic actions of a non-agonist PPARy ligand blocking Cdk5-mediated phosphorylation. Nature 477: 477-481 (2011).
Coelho, T., et al. A strikingly benign evolution of FAP in an individual found to be a compound heterozygote for two TTR mutations: TTR Met 30 and TTR Met 119. Journ. Rheumatol. 120: 179 (1993).
Coelho, T. Familial amyloid polyneuropathy: new developments in genetics and treatment. Curr. Opin. Neurol. 9(5): 355-359 (1996).
Cohen, F.E. and Kelly, J.W. Therapeutic approaches to protein-misfolding diseases. Nature 426(6968): 905-909 (2003).
Colon, W. and Kelly, J.W. Partial denaturation of transthyretin is sufficient for amyloid fibril formation in vitro. Biochemistry 31(36): 8654-8660 (1992).
Connelly, et al. Structure-based design of kinetic stabilizers that ameliorate the transthyretin amyloidosis. Current Opinion in Structural Biology 20(1): 5462 (2010).
Connors, L.H., et al. Tabulation of human transthyretin (TTR). Amyloid 10(3): 160-184 (2003).
Connors, L.H., et al. Cardiac amyloidosis in African Americans: comparison of clinical and laboratory features of transthyretin V122I amyloidosis and immunoglobulin light chain amyloidosis. Amer. Heart Journ. 158(4): 607-614 (2009).
Davidson, M.M., et al. Novel cell lines derived from adult human ventricular cardiomyocytes. Journ. Mol. Cell Cardiol. 39(1):133-147 (2005).
Dennis, M.S., et al. Albumin binding as a general strategy for improving the pharmacokinetics of proteins. Journ. Biol. Chem. 277(38): 35035-35043 (2002).
Desai, H.V., et al. Cardiac amyloidosis: approaches to diagnosis and management. Cardiol. Rev. 18(1): 1-11 (2010).
Dewar, M.J.S., et al. Development and use of quantum mechanical molecular models. 76. AM1: a new general purpose quantum mechanical molecular model. Journ. Amer. Chem. Soc. 107(13): 3902-3909 (1985).
Diana, G. D., et al. Synthesis and Antiherpetic Activity of Some 4-[(Aryloxy)alkyl]pyrazoles. J. Med. Chem. 24: 731-735 (1981).
Dickson, P.W., et al. Metabolism of prealbumin in rats and changes induced by acute inflammation. Eur. J. Biochem. 129: 289-293 (1982).
Douglass, E.F., et al. A comprehensive mathematical model for three-body binding equilibria. Journ. Amer. Chem. Soc. 135(16): 6092-6099 (2013).
El-Zohry, et al. Synthesis of some new 3-(2'-heterocylicethyl)-2-methyl-3,4-dihydroquinazolin-4-one derivatives as antimicrobial agents. J. Chem. Tech. Biotechnol. 55(3): 209-215 (1992).
Emerson, S.D., et al. NMR characterization of interleukin-2 in complexes with the IL-2R(alpha) receptor component, and with low molecular weight compounds that inhibit the IL-2/IL-R(alpha) interaction. Prot. Sci. 12(4): 811-822 (2003).
Engstrom, T., et al. Oxytocin receptor binding and uterotonic activity of carbetocin and its metabolites following enzymatic degradation. Eur. J. Pharmacol. 355: 203-210 (1998).

Epstein, M. Non-steroidal anti-inflammatory drugs and the continuum of renal dysfunction. Journ. Hypertens. Suppl. 20(6): S17-23 (2002).
Eswar, N., et al. Comparative protein structure modeling using Modeller. Curr. Prot. Bioinform. Ch. 5(Unit 5.6): 5.6.1-5.6.47 (2014).
Falk, R.H., et al. The systemic amyloidoses. New Engl. Journ. Med. 337(13): 898-909 (1997).
Fauci, A.S., et al. Harrison's Principles of Internal Medicine. 17 vol. 1448: 1763-1770 (2008).
Faulkes, C.G., et al. Social suppression of ovarian cyclicity in captive and wild colonies of naked mole-rats, Heterocephalus glaber. Journ. Reprod. Fertil. 88(2): 559-568.
Fenalti, G., et al. Molecular control of (delta)-opioid receptor signaling. Nature 506(7487): 191-196 (2014).
Fiser, A., et al. Modeling of loops in protein structures. Protein Sci. 9(9): 1753-1773 (2000).
Fishburn, C.S. The pharmacology of PEGylation: balancing PD with PK to generate novel therapeutics. Journ. Pharm. Sci. 97(10): 4167-4183 (2008).
Gaberc-Porekar, V., et al. Obstacles and pitfalls in the PEGylation of therapeutic proteins. Curr. Opin. Drug Disc. Devel. 11(2): 242-250 (2008).
Gallwitz, B. Glucagon-like peptide-1 analogues for type 2 diabetes mellitus: current and emerging agents. Drugs 71(13): 1675-1688 (2011).
Gell, D.A., et al. The detection and quantitation of protein oligomerization. Adv. Exp. Med. Biol. 747: 19-41 (2012).
Green, N.S., et al. Genistein, a natural product from soy, is a potent inhibitor of transthyretin amyloidosis. Proc. Nat. Acad. Sci. 102(41): 14545-14550.
Guo, H., et al. Influences of hydrocarbon linkers on the receptor binding affinities of gonadotropin-releasing hormone peptides. Bioorgan. Med. Chem. Lett. 23(20): 5484-5487 (2013).
Haigis, M.C. and Yankner, B.A. The aging stress response. Mol. Cell 40(2): 333-344 (2010).
Halmos, G., et al. Down-regulation of pituitary receptors for luteinizing hormone-releasing hormone (LH-RH) in rats by LH-RH antagonist cetrorelix. Proc. Nat. Acad. Sci. USA 93: 2398-2402 (1996).
Hammarstrom, P., et al. Trans-suppression of misfolding in amyloid disease. Science 293(5539): 2337-2572 (2001).
Hammarstrom, P., et al. Prevention of transthyretin amyloid disease by changing protein misfolding energetics. Science 299(5607): 713-716 (2003).
Hamour, I.M., et al. Heart transplantation for homozygous familial transthyretin (TTR) V122I cardiac amyloidosis. Amer. Journ. Heart Transplant. 8(5): 1056-1059 (2008).
Hayden, C. GnRH analogues: applications in assisted reproductive techniques. Eur. J. Endocrinol. 159: S17-S25 (2008).
He, M.M., et al. Small-molecule inhibition of TNF-alpha. Science 310(5750): 1022-1025 (2005).
Hill, R. T., et al. Plasmon Ruler with Angstrom Length Resolution. ACS Nano 6(10):9237-46 (2012).
Hopp, J., et al. The effects of affinity and valency of an albumin-binding domain (ABD) on the half-life of a single-chain diabody-ABD fusion protein. Protein Eng. Des. Sel. 23(11): 827-834 (2010).
Hull, R.L., et al. Islet amyloid: a critical entity in the pathogenesis of type 2 diabetes. Journ. Clin. Endocrinol. Metab. 89(8): 3629-3643 (2004).
Ingenbleek, Y. and Young, V. Transthyretin (prealbumin) in health and disease: nutritional implications. Annu. Rev. Nutr. 14: 495-533 (1994).
Jacobson, D.R., et al. A homozygous transthyretin variant associated with senile systemic amyloidosis: evidence for a late-onset disease of genetic etiology. Am. Journ. Hum. Gen. 47(1): 127-136 (1990).
Jacobson, D.R., et al. Variant-sequence transthyretin (isoleucine 122) in late-onset cardiac amyloidosis in black americans. New Engl. Journ. Med. 336(7): 466-473 (1997).
Jiang, X., et al. The V122I cardiomyopathy variant of transthyretin increases the velocity of rate-limiting tetramer dissociation, resulting in accelerated amyloidosis. Proc. Natl Acad. Sci. USA 98(26): 14943-14948 (2001).

(56) References Cited

OTHER PUBLICATIONS

Johnson, S.M., et al. Native state kinetic stabilization as a strategy to ameliorate protein misfolding diseases: a focus on the transthyretin amyloidases. Acc. Chem. Res. 38: 911-921 (2005).
Johnson, S.M., et al. Toward optimization of the linker substructure common to transthyretin amyloidogenesis inhibitors using biochemical and structural studies. Journ. Med. Chem. 51(20): 6348-6358 (2008).
Jonsen, E., et al. Early liver transplantation is essential for familial amyloidotic polyneuropathy patients' quality of life. Amyloid 8(1): 52-57 (2001).
Kaspar, A.A. and Reichert, J.M. Future directions for peptide therapeutics development. Drug Discovery Today 18(17/18): 807-817 (2013).
Kearney, P.M., et al. Do selective cyclo-oxygenase-2 inhibitors and traditional non-steroidal anti-inflammatory drugs increase the risk of atherothrombosis? Meta-analysis of randomised trials. 332(7553): 1302-1308 (2006).
Kirchheiner, J. and Brockmoller, J. Clinical consequences of cytochrome P450 2C9 polymorphisms. Clin. Pharmacol. Ther. 77(1): 1-16 (2005).
Koehler, A.N., et al. Discovery of an inhibitor of a transcription factor using small molecule microarrays and diversity-oriented synthesis. Journ. Am. Chem. Soc. 125(28): 8420-8421 (2003).
Kohno, K., et al. Analysis of amyloid deposition in a transgenic mouse model of homozygous familial amyloidotic polyneuropathy. Amer. Journ. Pathol. 150(4): 1497-1508 (1997).
Kolstoe, S.E. and Wood, S.P. Drug targets for amyloidosis. Biochem. Soc. Trans. 38(2): 466-470 (2010).
Konterman, R. in Therapeutic Proteins: Strategies to Modulate Their Plasma Half-lives. Weinheim: Wiley-VCH Verlag GmbH & Co. (2012).
Lang, P.T., et al. DOCK 6: Combining techniques to model RNA-small molecule complexes. RNA 15: 1219-1230 (2009).
Leavitt, S. and Freire, E. Direct measurement of protein binding energetics by isothermal titration calorimetry. Curr. Opin. Struct. Biol. 11(5): 560-566.
Levy, O.E., et al. Novel exenatide analogs with peptidic albumin binding domains: potent anti-diabetic agents with extended duration of action. PLoS One 9 e87704 (2014).
Li, Z.J. and Cho, C.H. Development of peptides as potential drugs for cancer therapy. Curr. Pharm. Des. 16(10): 1180-1189 (2010).
Liu, J., et al. Calcineurin is a common target of cyclophilin-cyclosporin A and FKBP-FK506 complexes. Cell 66(4): 513-524 (1991).
Lu, et al. Structure and Composition of Dodecane Layers Spread on Aqueous Solutions of Dodecyl- and Hexadecyltrimethylammonium Bromides Studied by Neutron Reflection. J. Phys. Chem 99: 4113-23 (1995).
Lubberink, M.L., et al. In-DTPA-D-Phe1-ocreotide for imaging of neuroendocrine tumors with PET. J. Nucl. Med. 43(10): 1391-1397 (2002).
Mager, D.E. and Jusko, W.J. General pharmacokinetic model for drugs exhibiting target-mediated drug disposition. J. Pharmacokinet. Pharmacodyn. 28(6): 507-532 (2001).
Marinec, P.S., et al. FK506-binding protein (FKBP) partitions a modified HIV protease inhibitor into blood cells and prolongs its lifetime in vivo. Proc. Nat. Acad. Sci. USA. 106(5): 1336-1341 (2009).
Marnett, L.J. and Kalgutkar, A.S. Cyclooxygenase 2 inhibitors: discovery, selectivity, and the future. Trends Pharmacol. Sci. 20(11): 465-469 (1999).
McCutchen, S.L., et al. Transthyretin mutation Leu-55-Pro significantly alters tetramer stability and increases amyloidogenicity. Biochemistry 32(45): 12119-12127 (1993).
Miller, S.R., et al. Native state stabilization by NSAIDs inhibits transthyretin amyloidogenesis from the most common familial disease variants. Lab Invest. 84(5): 545-552 (2004).

Mitragotri, S., et al. Overcoming the challenges in administering biopharmaceuticals: formulation and delivery strategies. Nat. Rev. Drug Discov. 13: 655-672 (2014).
Miyawaki, A. Development of probes for cellular functions using fluorescent proteins and fluorescence resonance energy transfer. Annu. Rev. Biochem. 80: 357-373 (2011).
Mock, E.J., et al. Daily rhythmicity of serum testosterone concentration in the male laboratory rat. Endocrinology 103(4): 1111-1121 (1978).
Monaco, H.L., et al. Structure of a complex of two plasma proteins: transthyretin and retinol-binding protein. Science 268: 1039-1041 (1995).
Moradi, S.V., et al. Synthesis and in vitro evaluation of glycosyl derivatives of luteinizing hormone-releasing hormone (LHRH). Bioorg. Med. Chem. 21(14): 4259-4265 (2013).
Morgat, C., et al. Targeting neuropeptide receptors for cancer imaging and therapy: perspectives with bombesin, neurotensin, and neuropeptide-Y receptors. J. Nucl. Med. 55(10): 1650-1657 (2014).
Mukherjee, D., et al. Risk of cardiovascular events associated with selective COX-2 inhibitors. Journ. Amer. Med. Assoc. 286(8): 954-959 (2001).
Nagy, A. and Schally, A.V. Targeting cytotoxic conjugates of somatostatin, luteinizing hormone-releasing hormone and bombesin to cancers expressing their receptors: a "smarter" chemotherapy. Curr. Pharm. Des. 11(9): 1167-1180.
Nagy, A. and Schally, A.V. Targeting of cytotoxic luteinizing hormone-releasing hormone analogs to breast, ovarian, endometrial, and prostate cancers. Biology of Reproduction 73: 851-859 (2005).
Naor, Z., et al. Characterization of gonadotropin-releasing hormone with receptors in cultured rat pituitary cells. Endocrinology 107(4): 1144-1152.
Naor, Z., et al. Interaction of fluorescent gonadotropin-releasing hormone with receptors in cultured pituitary cells. Journ. Biol. Chem. 256(6): 3049-3052 (1981).
Naylor, H.M. and Newcomer, M.E. The structure of human retinol-binding protein (RBP) with its carrier protein transthyretin reveals an interaction with the carboxy terminus of RBP. Biochemistry 38: 2647-2653 (1999).
Noy, N., et al. Interactions of retinol with binding proteins: studies with retinol-binding protein and with transthyretin. Biochemistry 31(45): 11118-11124.
Page, J. and Henry, D. Consumption of NSAIDs and the development of congestive heart failure in elderly patients: an under-recognized public health problem. Arch. Intern. Med. 160(6): 777-784 (2000).
Patching, S.G. Surface plasmon resonance spectroscopy for characterization of membrane protein-ligand interactions and its potential for drug discovery. Biochim. Biophys. Acta 1838(1 Pt A): 43-55 (2104).
Penchala, S.C., et al. AG10 inhibits amyloidogenesis and cellular toxicity of the familial amyloid cardiomyopathy-associated V122I transthyretin. Proc. Nat. Acad. Sci. USA 110 (24): 9992-9997 (2013).
Peterson, S.A., et al. Inhibiting transthyretin conformational changes that lead to amyloid fibril formation. Proc. Nat. Acad. Sci. USA 95(22): 12956-12960.
Prapunpoj, P., et al. Change in structure of the N-terminal region of transthyretin produces change in affinity of transthyretin to T4 and T3. FEBS Journal 273(17): 4013-4023 (2006).
Quintas, A., et al. The amyloidogenic potential of transthyretin variants correlates with their tendency to aggregate in solution. FEBS Letters 418(3): 297-300 (1997).
Ran, C., et al. Non-conjugated small molecule FRET for differentiating monomers from higher molecular weight amyloid beta species. PLoS One 6(4): e19362 1-6 (2011).
Rapezzi, C., et al. Transthyretin-related amyloidosis and the heart: a clinical overview. Nat. Rev. Cardiol. 7(7): 398-408 (2010).
Raz, A. and Goodman, D.S. The interaction of thyroxine with human plasma prealbumin and with the prealbumin-retinol-binding protein complex. Journ. Biol. Chem. 244(12): 3230-3237 (1969).

(56) References Cited

OTHER PUBLICATIONS

Reixach, N., et al. Tissue damage in the amyloidosis: transthyretin monomers and nonnative oligomers are the major cytotoxic species in tissue culture. Proc. Nat. Acad. Sci. USA 101(9): 2817-2822 (2004).
Rickert, M., et al. The structure of interleukin-2 complexed with its alpha receptor. Science 308(5727): 1477-1480 (2005).
Rink, H. Solid-phase synthesis of protected peptide fragments using a trialkoxy-diphenyl-methylester resin. Tetrahedron Lett. 28(33): 3787-3790 (1987).
Rodrigues, A.D. Impact of CYP2C9 genotype on pharmacokinetics: are all cyclooxygenase inhibitors the same? Drug Metab. Dispos. 33(11): 1567-1575 (2005).
Ruggiero, A., et al. Paradoxical glomerular filtration of carbon nanotubes. Proc. Nat. Acad. Sci. USA 107(27): 12369-12374 (2010).
Sali, A. and Blundell, T.L. Comparative protein modeling by satisfaction of spatial restraints. J. Mol. Biol. 234: 779-815 (1993).
Saraiva, M.J. Transthyretin mutations in health and disease. Human Mutation 5(3): 191-196 (1995).
Saraiva, M.J. Transthyretin mutations in hyerthyroxinemia and amyloid diseases. Human Mutation 17(6): 493-503 (2001).
Schellenberger, V., et al. A recombinant polypeptide extends the in vivo half-life of peptides and proteins in a tunable manner. Nat. Biotechnol. 27(12): 1186-1190 (2009).
Sekijima, Y., et al. Pathogenesis of and therapeutice strategies to ameliorate the transthyretin amyloidosis. Curr. Pharm. Des. 14(30): 3219-3230 (2008).
Selkoe, D.J. Folding proteins in fatal ways. Nature 426(6968): 900-904 (2003).
Selkoe, D.J. Cell biology of protein misfolding: the examples of alzheimer's and parkinson's diseases. Nat. Cell Biol. 6(11): 1054-1061 (2004).
Seminara, S.B., et al. Gonadotropin-releasing hormone deficiency in the human (idiopathic hypogonadotropic hypogonadism and Kallman's syndrome): pathophysiological and genetic considerations. Endocrine Reviews 19(5): 521-539 (1998).
Shah, K.B., et al. Amyloidosis and the heart: a comprehensive review. Arch. Intern. Med. 166(17): 1805-1813 (2006).
Sleep, D., et al. Albumin as a versatile platform for drug half-life extension. Biochim. Biophys. Acta Gen. Subj. 1830(12): 5526-5534 (2013).
Spinks, A.C., et al. Circulating LH levels and the response to exogenous GnRH in the common mole-rat: implications for reproductive regulation in this social, seasonal breeding species. Horm. Behav. 37(3): 221-228 (2000).
Sroda, K., et al. Repeated injections of PEG-PE liposomes generate anti-PEG antibodies. Cell. Mol. Biol. Lett. 10(1): 37-47 (2005).
Stefani, M. Protein misfolding and aggregation: new examples in medicine and biology of the dark side of the protein world. Biochimica et Biophysica Acta 1739: 5-25 (2004).
Suhr, O.B., et al. Liver transplantation for hereditary transthyretin amyloidosis. Liver Transplantation 6(3): 263-276 (2000).
Sundelin, J., et al. The primary structure of rabbit and rat prealbumin and a comparison with the tertiary structure of human prealbumin. J. Biol. Chem. 260(10): 6481-6487 (1985).
Trivella, D.B., et al. Conformational differences between the wild type and V30M mutant transthyretin modulate its binding to genistein: implications to tetramer stability and ligand-binding. Journ. Struct. Biol. 170(3): 522-531.
Trussel, S., et al. New strategy for the extension of the serum half-life of antibody fragments. Bioconjug. Chem. 20: 2286-2292 (2009).
Tweedle, M.F. Peptide-targeted diagnostics and radiotherapeutics. Acc. Chem. Res. 42(7): 958-968 (2009).
Vickery, B.H. Comparison of the potential for therapeutic utilities with gonadotropin-releasing hormone agonists and antagonists. Endocrine Reviews 7(1): 115-124 (1986).
Wallace, J.L. Pathogenesis of NSAID-induced gastroduodenal mucosal injury. Best Pract. Res. Clin. Gastroenterol. 15(5): 691-703 (2001).
Wegener, D., et al. A fluorogenic histone deacetylase assay well suited for high-throughput activity screening. Chemistry & Biology 10: 61-68 (2003).
Westermark, P., et al. Fibril in senile systemic amyloidosis is derived from normal transthyretin. Proc. Nat. Acad. Sci. USA 87(7): 2843-2845 (1990).
Wiseman, R.L., et al. Kinetic stabilization of an oligomeric protein by a single ligand binding event. Journ. Am. Chem. Soc. 127(15): 5540-5551 (2005).
Wojtczak, A., et al. Structures of human transthyretin complexed with thyroxine at 2.0 a resolution and 3',5'-dinitro-N-acetyl-L-thyronine at 2.2 a resolution. Acta Crystallographica Section D Biological Crystallography 52(4): 758-765 (1996).
Yi, S., et al. Systemic amyloidosis in transgenic mice carrying the human mutant transthyretin (Met30) gene. Pathologic similarity to human familial amyloidotic polyneuropathy, type I. Amer. Journ. Pathol. 138(2): 403-412 (1991).
Zhang, J.H., et al. A simple statistical parameter for use in evaluation and validation of high throughput screening assays. Journ. Biomol. Screen. 4(2): 67-73 (1999).
Zobel, K., et al. Phosphate ester serum albumin affinity tags greatly improve peptide half-life in vivo. Bioorg. Med. Chem. Lett. 13: 1513-1515 (2003).
http://clinicaltrials.gov/ct2/show/NCT00294671.
http://clinicaltrials.gov/ct2/show/NCT00791492.

VIIIc

TLHE1

TLHE2

TLHE3

Conj8

Conj9

Conj10

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Leu Tyr Glu Asn Lys Pro Arg Arg Pro Tyr Ile Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu His Trp Ser Tyr Gly Leu Arg Pro Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Lys

<400> SEQUENCE: 3

Glu His Trp Ser Tyr Lys Leu Arg Pro Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (6)..(6)
<223> OTHER INFORMATION: D-Lys

<400> SEQUENCE: 4

Glu His Trp Ser Tyr Lys Leu Arg Pro Gly
1               5                   10
```

DELIVERING ENHANCED ACTIVE AGENTS

CROSS-REFERENCE TO RELATED APPLICATION

This application is a continuation of U.S. application Ser. No. 16/193,407, filed Nov. 16, 2018, which is a continuation of Ser. No. 15/446,212, filed Mar. 1, 2017, which is a continuation of Ser. No. 14/804,024, filed Jul. 20, 2015, which claims the benefit of U.S. Provisional Application No. 62/037,592, filed Aug. 14, 2014, each of which is hereby incorporated herein by reference in it's entirety.

STATEMENT REGARDING FEDERALLY SPONSORED RESEARCH OR DEVELOPMENT

The inventions disclosed herein were made with governmental support under grant 1R15GM110677-01 from the National Institutes of Health. The government has certain rights in the inventions.

SEQUENCE LISTING

This application contains a Sequence Listing which has been submitted in ASCII format via EFS-Web in U.S. application Ser. No. 16/193,407, filed Nov. 16, 2018 ("the 407 application"), and is hereby transferred and incorporated by reference in its entirety from the 407 application. Said ASCII copy, created on Jul. 20, 2015, is named UOPDP001US01_SL.txt and is 1,588 in size. The Sequence Listing is filed in accordance with WIPO Handbook on Industrial Property Information and Documentation, Standard ST.25 paragraph 39.

BACKGROUND

Field of the Invention

The teachings provided herein are directed to a delivery system for active agents having a ligand that is selective for transthyretin (TTR) in the serum of a subject; and, a linker configured for operatively attaching the ligand covalently to an active agent to increase the half-life of the active agent in the serum.

Description of the Related Art

Many seemingly useful drugs have not fulfilled their potential due to their poor pharmacokinetic (PK) profiles. This is true of many potentially useful drugs, for example, that are comprised of a peptide, an oligopeptide, a polypeptide, a protein, an antibody, an oligonucleotide, a polynucleotide, a virus-like particle, a small molecule, an oligosaccharide, an imaging agent, or a combination thereof. For example, peptides, such as those less than about 50 amino acids in length, play a crucial role in many biochemical and physiological processes. Many FDA-approved drugs are peptides used for a range of disorders, such as cancer, diabetes, among others. In addition, peptides hold great potential as both diagnostic agents and targeting ligands. The higher potency, selectivity, and safety of peptides over small molecule drugs have made peptides attractive as drug candidates and, therefore, the number of new peptides entering clinical trials continues to grow. Unfortunately, the poor pharmacokinetic profile of many peptides represents a major challenge in their continued development. This problem, in particular, has limited the ability of many peptides to reach their tremendous therapeutic potential.

The half-life of a peptide in the blood serum of a subject is of serious concern. This is because many otherwise useful peptides have a very short in vivo half-life of, perhaps, of 2-30 minutes. This is usually due to (i) enzymatic degradation by serum proteases and/or (ii) fast renal clearance due to the molecular weight cutoff for peptides and proteins to be cleared through glomerular filtration being relatively high at approximately 30 kilodaltons. Those of skill in the art recognize that the short in vivo half-life of peptides has limited their clinical potential by increasing the size and frequencies of doses needed to achieve the desired results, for example.

FIG. 1 illustrates the half-life problem and a state-of-the-art remedy that has been used in the art to address the problem by increasing the hydrodynamic size of a peptide through PEGylation. The right panel of FIG. 1 shows the inactivation of peptides by serum proteases and kidney filtration, whereas the left panel shows a covalent conjugation of peptides to macromolecules. The PEGylation shown in FIG. 1 is covalent conjugation 105 of peptides 110 to polyethylene glycol (PEG) polymers 115. This remedy has been used to the extent that a few PEGylated peptides have reached the market, including peginesatide (OMONTYS by Affymax, Cupertino, Calif.). Peginesatide is an example of a ~5 kDa peptide that is covalently linked to a PEG polymer to increase it's half-life in blood serum. It has a molecular weight of ~45 kDa and has been used to treat anemia associated with chronic kidney disease in adult patients on dialysis. By increasing the hydrodynamic size of peptides through covalent PEGylation, the in vivo half-life of the peptide increases by reducing filtration 120 by the kidneys, for example. In addition, the steric bulk of PEG moiety increases in vivo half-life of the peptide 110 by protecting it against degradation 125 by proteases. Unfortunately, PEGylation has introduced some problems to art: (i) the steric hindrance 130 of the large PEG moiety often harms the binding affinity of the peptide 110 to its extra-cellular receptor 135 on a target cell 140, which compromises the therapeutic pharmacodynamic (PD) properties of the peptide 110, such that the the binding affinity of the peptides to its receptor is compromised; (ii) renal tubular vacuolation that correlates to the PEGylation has been reported in animal models (iii) animals and humans could generate antibodies against PEG, resulting in an undesirable immune response and, (iv) the manufacturing process and refrigerated storage add significantly to the costs of making, storing, and transporting the PEGylated peptides.

Serum proteins have also been conjugated to peptides, such serum proteins selected as being too large to be filtered through the kidneys. An example is the covalent peptide conjugation to a recombinant human serum albumin (rHSA). Human serum albumin has a molecular weight of 67 kDa, combining the long, ~20 day serum half-life of the HSA with the therapeutic effect of the peptide. One problem is that the serum half-life of the HSA is a bit too long for some peptide therapies, and other serum proteins, such as recombinant transthyretin (TTR) have been investigated. Transthyretin has a molecular weight of 55 kDa and a half-life of ~2 days. The covalent conjugation of TTR to peptides has been successful at increasing their serum half-lives. Unfortunately, however, both the rHSA and TTR conjugations share many of the limitations of the PEGylation approach, including a decreased binding affinity and potency of the peptide, in addition to increased costs of making, storing, and transporting the peptide for use.

AG10 (Compound VIIc) is a potent and selective small-molecule TTR ligand. FIGS. 2A-2B illustrate the structure of hTTR bound to AG10 (Compound VIIc) and the structure of AG10 with potential sites for linker attachment are labeled as ortho & meta, according to some embodiments. And, FIGS. 3A-3C illustrate linker-modified AG10 analogs that enhance in vitro and in vivo half-life of peptides, according to some embodiments. We refer to these analogs as TTR ligands for half-life extension, or TLHEs. One of skill will appreciate that we successfully demonstrate that conjugation of a TLHE to a number of peptides enhances the in vitro and in vivo half-life of the peptide without compromising its target affinity, and that this translates into superior in vivo efficacy.

Accordingly, and for at least the above reasons, the art will appreciate having a delivery system that (i) improves the half-life of active agents that are otherwise very useful; (ii) avoids steric hindrance problems that affect binding affinity and potency of the active agents; (iii) avoids the renal tubular vacuolation caused by PEGylation; (iv) avoids the generation of antibodies that create immune response problems; and (v) avoids the manufacturing process and refrigerated storage that add significantly to the costs of making, storing, and transporting the PEGylated, Fc, and albumin conjugated peptides and active agents.

SUMMARY

The teachings provided herein are directed to a delivery system for active agents having a ligand that is selective for a plasma protein, for example, transthyretin, in the serum of a subject; and, a linker configured for operatively attaching the ligand covalently to an active agent to increase the half-life of the active agent in the serum.

The teachings include a delivery system for an active agent comprising a ligand with (i) a high selectivity for a plasma protein endogeneous to the subject, the molecular weight of the plasma protein ranging from about 30 kDa to about 80 kDa; (ii) a high binding affinity, Kd, of at least $10^{-6}$ M for the plasma protein; and, (iii) a molecular weight ranging from about 200 Da to about 2000 Da; and, a linker that ranges in length from about 10 angstroms to about 50 angstroms, or from 8 atoms to 50 atoms. The active agent can have a structure selected from the group consisting of a peptide, an oligopeptide, a polypeptide, a protein, an antibody, an oligonucleotide, a polynucleotide, a virus-like particle, a small molecule, an imaging agent, and combinations thereof.

In some embodiments, the plasma protein can be selected from the group consisting of serum albumin, transferrin, Retinol binding protein, alpha-1 globulins, alpha-2 globulins, beta globulins, and gamma globulins, or a combination thereof. In some embodiments, the plasma protein is HSA. And, in some embodiments, the plasma protein is TTR.

The teachings also include a delivery system for an active agent comprising a ligand of particular interest which is selective for transthyretin in the serum of a subject; and, a linker configured for operatively attaching the ligand covalently to an active agent. In some embodiments, the linker ranges in length from 10 angstroms to 50 angstroms, or from 10 atoms to 22 atoms. The ligand can have the following structure of Compound (I)

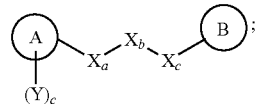

(I)

where $X_a$, $X_b$ and $X_c$ are independently selected from $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

a ring is a 4 to 12-membered ring, in certain embodiments the 4 to 12-membered ring is an aromatic or heteroaromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano;

c is an integer ranging from 0 to 5; and,

B ring is a heterocyclic ring selected from the following (h1-h30):

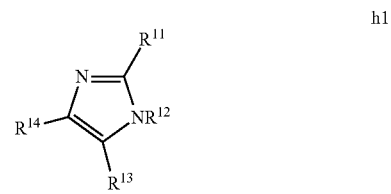

h1

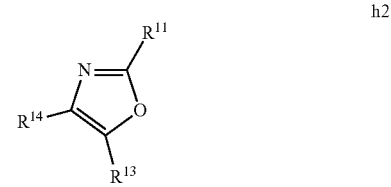

h2

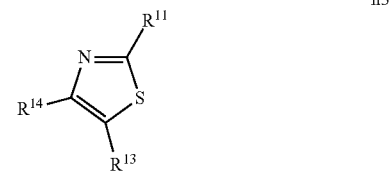

h3

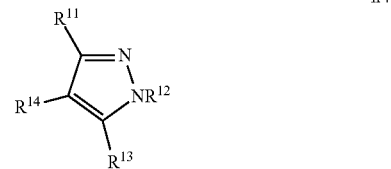

h4

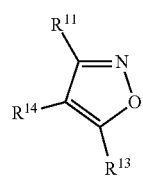 h5
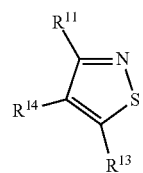 h6
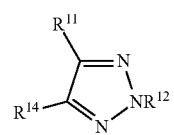 h7
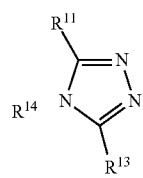 h8
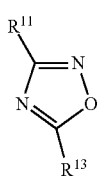 h9
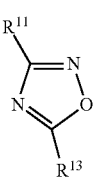 h10
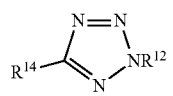 h11
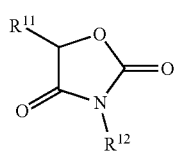 h12
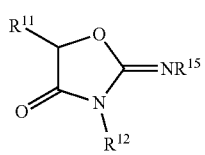 h13
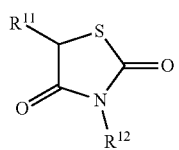 h14
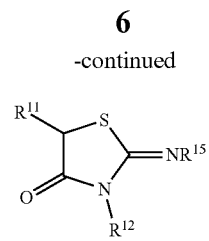 h15
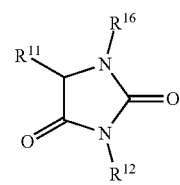 h16
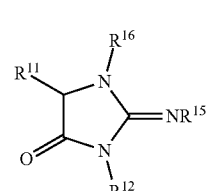 h17
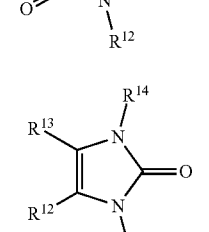 h18
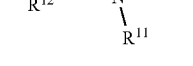 h19
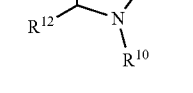 h20
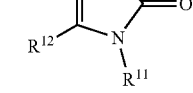 h21
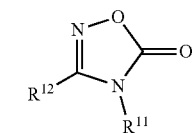 h22
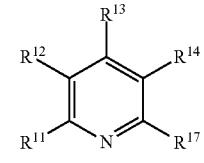 h23
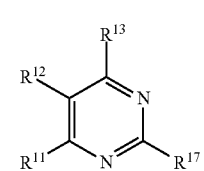

-continued

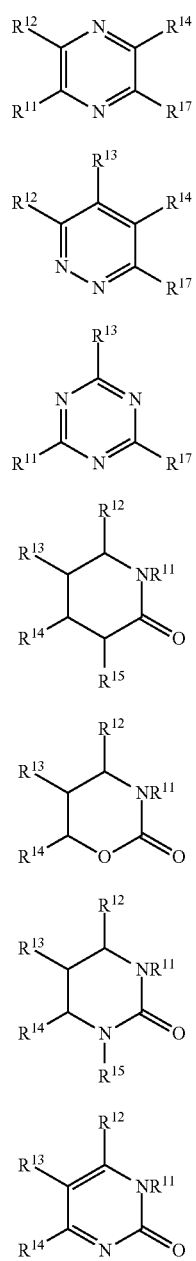

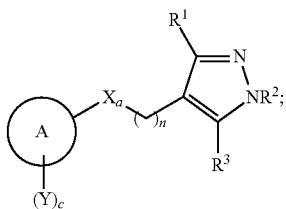

where $R^{11}$-$R^{16}$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano; $R^{17}$ is selected from a hydroxyl, alkyl, amino, and alkyl amino; and at least one of $R^{11}$—$R^{16}$ is the linking group to $X_c$;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand can have the following structure of Compound (II), comprising:

where,
n is an integer ranging from 0 to 8;
$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano;
$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;
A is a 5 to 12-membered ring, in certain embodiments the 5 to 12-membered ring is an aromatic or heteroaromatic ring;
each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and,
c is a number from zero to 5;
or, a pharmaceutically acceptable salt, ester, enol ether, enol ester, amide, acetal, ketal, orthoester, hemiacetal, hemiketal, hydrate, solvate or prodrug thereof.

In some embodiments, the ligand has the structure of Compound (III), comprising:

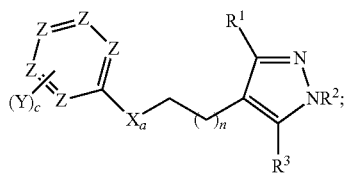

where,
n is an integer ranging from 0 to 7;
Z is carbon and/or up to three of the five Z may be nitrogen;
R1, R2 and R3 are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

Xa is C(R4)(R5), O, N—R5 or S; where R4 and R5 are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is an integer ranging from 0 to 5;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand of Compound (III) is a structure in which n is 3; and, X is O.

In some embodiments, the ligand has the structure of Compound (IV), comprising:

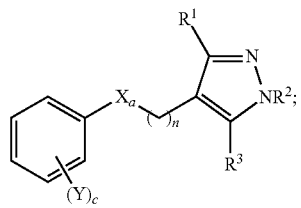

(IV)

where, n is an integer ranging from 1 to 4;

$R^1$ is a short chain alkyl having 1 to 4 carbon atoms;

$R^2$ is hydrogen;

$R^3$ is a short chain alkyl having 1 to 4 carbon atoms;

$X_a$ is $C(R^4)(R^5)$, 0, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, halogen, acyl, substituted acyl, carboxyl, heterocyclic group, alkoxycarbonyl sulfonamide, sulfonyl fluoride, thioester and substituted alkoxycarbonyl; and c is 2;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand of Compound (IV) is a structure in which R1 is methyl and R3 is methyl; Xa is O; and, Y is fluoro or carboxyl.

In some embodiments, the ligand has structure of Compound (V), comprising:

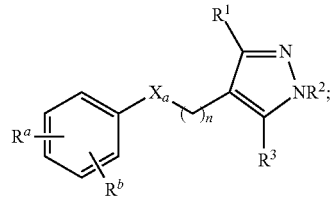

(V)

where, n is 1 to 8;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halo, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, 0, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^a$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, CF$_3$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

$R^b$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, CF$_3$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

$R^6$ is alkyl, haloalkyl, cycloalkyl, or heterocyclyl;

$R^7$ and $R^8$ are each independently hydrogen, alkyl, alkenyl, alkynyl, cycloalkyl, heterocyclyl, or heteroaryl; and, $R^9$ is the side chain of a naturally occurring α-amino carboxylic acid;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand of Compound (V) is a structure in which $R^b$ is selected from bromo, chloro and fluoro.

In some embodiments, the ligand has the structure of Compound (VI), comprising:

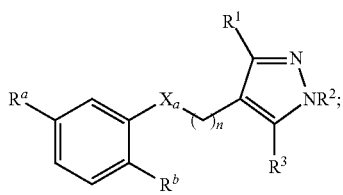

(VI)

where, n is 3;

$R^1$ is a short chain alkyl having 1 to 4 carbon atoms;

$R^2$ is hydrogen;

$R^3$ is a short chain alkyl having 1 to 4 carbon atoms;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^a$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, hydrogen, an acyl, substituted acyl, carboxyl, alkoxycarbonyl, heterocyclic group, sulfonamide, sulfonyl fluoride, thioester, or substituted alkoxycarbonyl;

$R^b$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, a halogen or heterocyclic group;

$R^6$ is alkyl, haloalkyl, cycloalkyl, or heterocyclyl;

$R^7$ and $R^8$ are each independently hydrogen, alkyl, alkenyl, alkynyl, cycloalkyl, heterocyclyl, or heteroaryl; and $R^9$ is the side chain of a naturally occurring α-amino carboxylic acid;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIc):

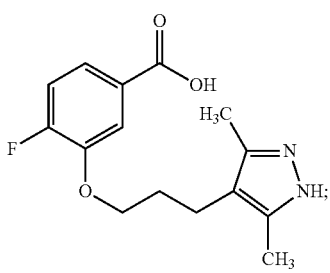

(VIIc)

or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIa), comprising:

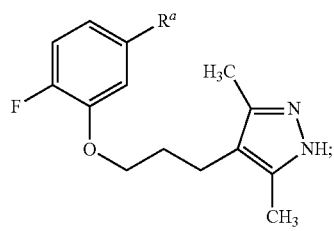

(VIIa)

where, $R^a$ is OH, CHO, COOH, CONH$_2$, CONH(OH), COOR$^6$, CONHR$^6$;

$R^6$ is straight of branched alkyl of 1-3 carbon atoms;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIb), comprising:

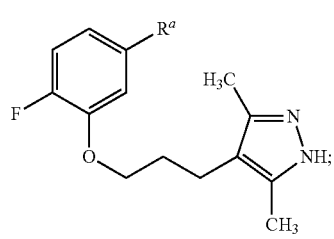

(VIIb)

where, $R^a$ is COOH, CONH$_2$, CONH(OH), COOR$^6$, CONHR$^6$;

$R^6$ is straight of branched alkyl of 1-3 carbon atoms;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand is selected from the group consisting of:

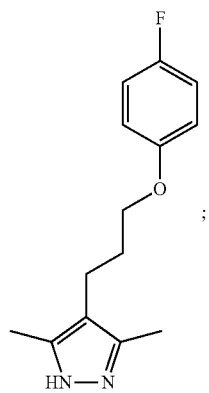

(VIId)

(VIIe)
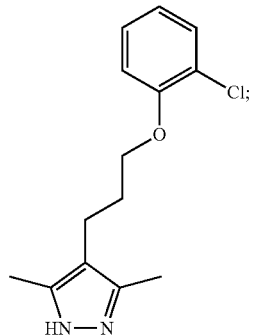
(VIIf)
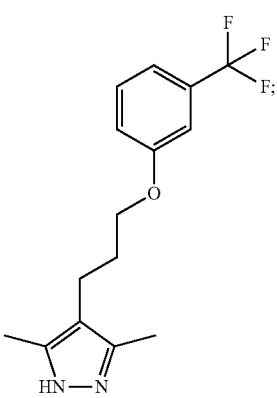
(VIIg)
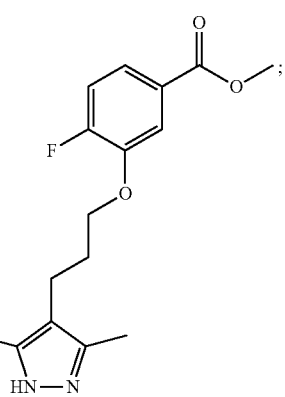
(VIIh)
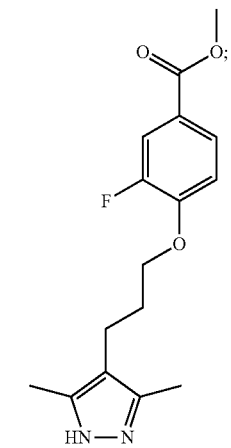
(VIIi)
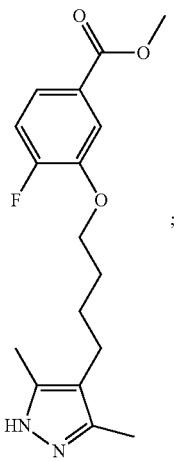
(VIIj)
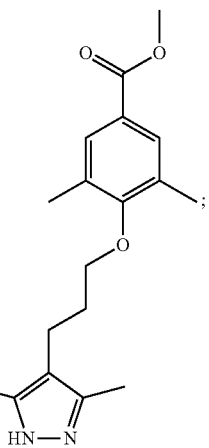
(VIIk)
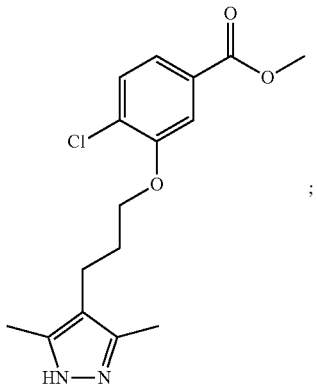

-continued
(VIII)
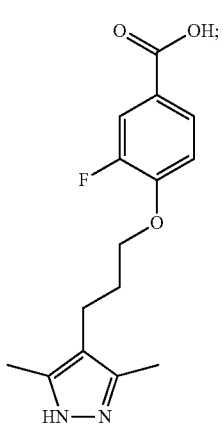
(VIIm)
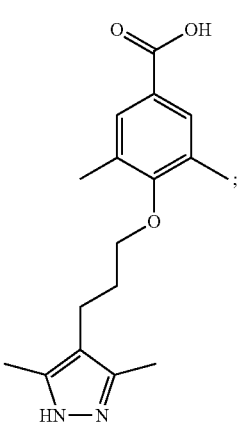
(VIIn)
-continued
(VIIo)
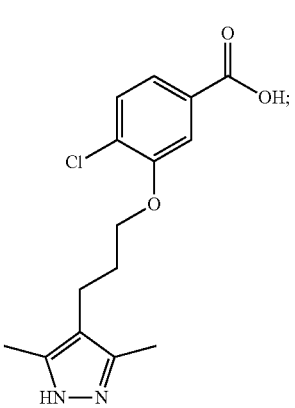
(VIIIa)
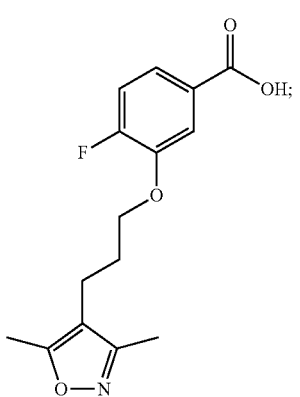
(VIIIb)
and, a pharmaceutically acceptable salt, ester, enol ether, enol ester, acetal, amide, ketal, orthoester, hemiacetal, hemiketal, hydrate, solvate or prodrug thereof.
In some embodiments, the ligand has the structure of Compound (VIIIc):

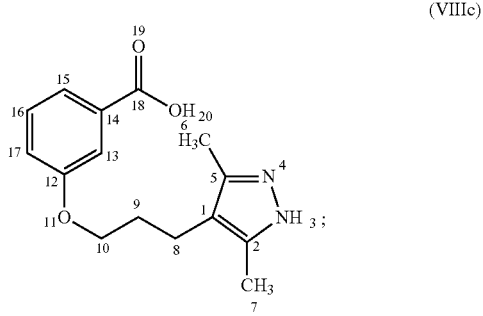 [SMILES: Cc1n[nH]c(C)c1CCCOc1cccc(C(=O)O)c1]

(VIIIc)

or, a pharmaceutically acceptable salt, ester, enol ether, enol ester, acetal, amide, ketal, orthoester, hemiacetal, hemiketal, hydrate, solvate or prodrug thereof; and,
the linker is attached to the ligand ortho at C15 to the carboxyl group at C14.

In some embodiments, the ligand has the structure of Compound (VIIIc):

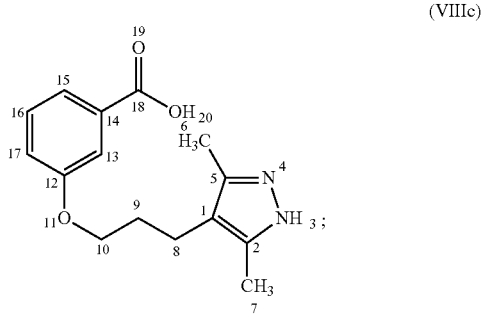 [SMILES: Cc1n[nH]c(C)c1CCCOc1cccc(C(=O)O)c1]

(VIIIc)

or, a pharmaceutically acceptable salt, ester, enol ether, enol ester, acetal, amide, ketal, orthoester, hemiacetal, hemiketal, hydrate, solvate or prodrug thereof; and,
the linker is attached to the ligand meta at C16 to the carboxy carbon at C14.

The teachings include a method of increasing the in vivo half-life of an active agent, the method comprising covalently attaching any of the delivery systems taught above to an active agent.

The teachings include a method of administering an active agent to a subject, the method comprising covalently attaching any of the delivery systems taught above to an active agent to create a conjugated active agent; and, administering the conjugated active agent to the subject.

The teachings include a method of reducing the immunogenicity of an active agent in a subject, the method comprising obtaining a delivery system having a ligand with (i) a high selectivity for a plasma protein endogeneous to the subject, the molecular weight of the plasma protein ranging from about 30 kDa to about 80 kDa; (ii) a high binding affinity, Kd, of at least $10^{-6}$ M for the plasma protein; and, (iii) a molecular weight ranging from about 200 Da to about 2000 Da; and, a linker that ranges in length from about 10 angstroms to about 50 angstroms, or from 10 atoms to 50 atoms. The method also includes covalently attaching the delivery system to an active agent to create a conjugated active agent; and, administering the conjugated active agent to the subject; wherein, the plasma protein shields the active agent from antibody generation in the subject after the administering.

In some embodiments, the delivery system can be any of the delivery systems taught above. In some embodiments, the plasma protein can be selected from the group consisting of serum albumin, transferrin, Retinol binding protein, alpha-1 globulins, alpha-2 globulins, beta globulins, and gamma globulins, or a combination thereof. In some embodiments, the plasma protein is HSA. And, in some embodiments, the plasma protein is TTR.

Moreover, it should be appreciated that the active agent can be any active agent known to one of skill that can benefit from the delivery systems taught herein. In some embodiments, the active agent comprises a structure selected from the group consisting of a peptide, an oligopeptide, a polypeptide, a protein, an antibody, an oligonucleotide, a polynucleotide, a virus-like particle, a small molecule, an oligosaccharide, an imaging agent, and combinations thereof.

DETAILED DESCRIPTION

Figure 1:
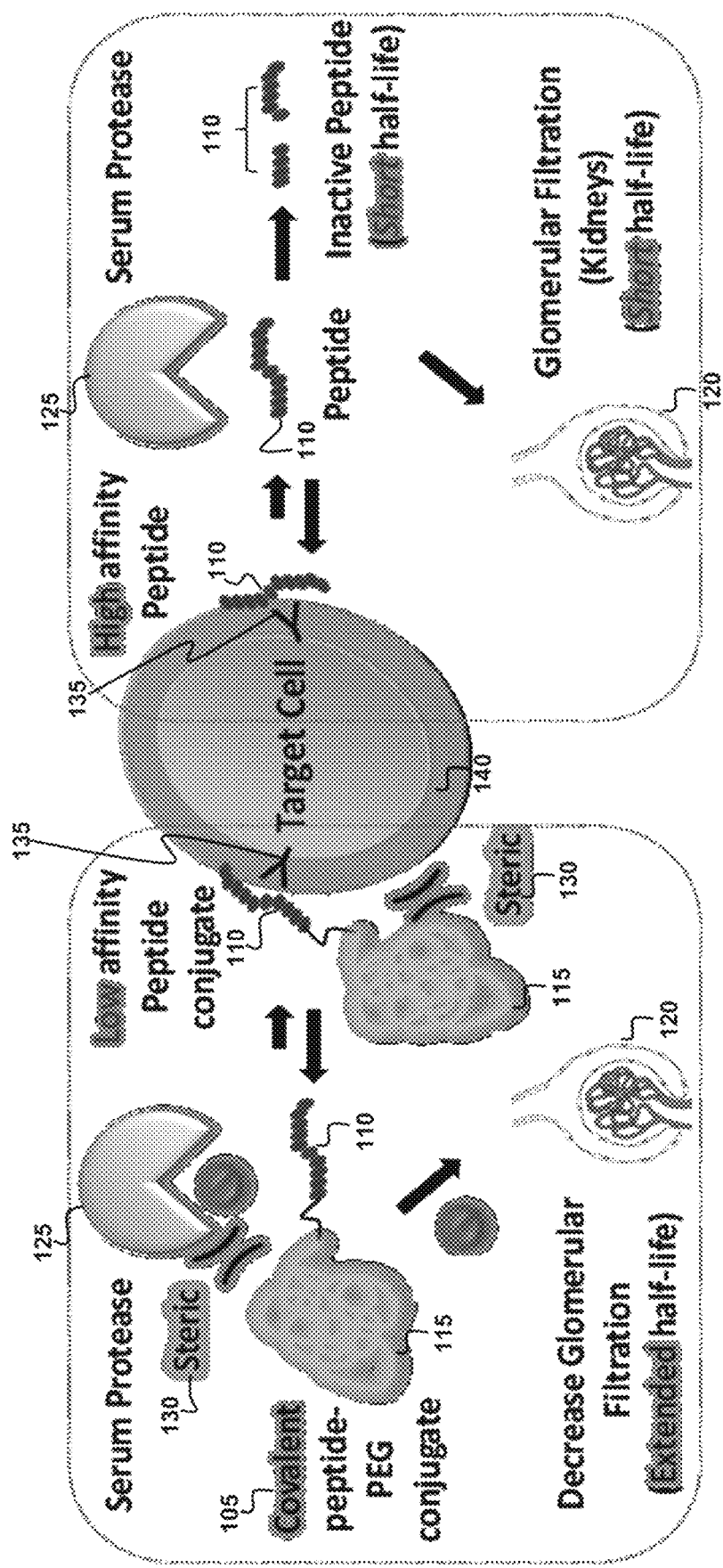
FIG. 1 illustrates the half-life problem and a state-of-the-art remedy that has been used in the art to address the problem by increasing the hydrodynamic size of a peptide through PEGylation.

A delivery system for active agents, and methods of making and using the systems, are provided. The delivery systems have (i) a ligand that is selective for an endogeneous plasma protein in the serum of a subject; and, (ii) a linker configured for operatively attaching the ligand covalently to an active agent to increase the half-life of the active agent in the serum.

The term "half-life" can be used to refer to lose half of its activity, for example, its pharmacologic, physiologic, or radiologic activity. The term "half-life" can be used interchangeably with the terms "biological half-life" or "terminal half-life". In some embodiments, the half-life of a substance is the time it takes for a substance, for example, a metabolite, drug, signalling molecule, radioactive nuclide, or other substance, to lose half of its pharmacologic, physiologic, or radiologic activity. In some embodiments, the term half-life can be used to refer to the body's cleansing through the function of kidneys and liver in addition to excretion functions to eliminate a substance from the body. In some embodiments, the term "half-life" can be used to refer to the time it takes for the blood plasma concentration of a substance to halve (plasma half-life) its steady-state. In some embodiments, the half-life of the activity of the active agent can range from about 30 minutes to about 30 days when administered to a subject with the delivery systems provided herein. For example, the half-life of the activity of the active agent can range from about 30 minutes to about 2 days when administered to a subject with a delivery system taught herein having a ligand that is highly selective for transthyretin, in some embodiments. Likewise, the half-life of the activity of the active agent can range from about 30 minutes to about 2 days when administered to a subject with a delivery system taught herein having a ligand that is highly selective for human serum albumin, in some embodiments. As such, in some embodiments the half-life of the activity of the active agent can be about 30 minutes, about 1 hour, about 2 hours, about 3 hours, about 4 hours, about 6 hours, about 8 hours, about 10 hours, about 12 hours, about 18 hours, about 24 hours, about 2 days, about 3 days, about 4 days, about 5 days, about 6 days, about 10 days, about 12 days, about 16 days, about 20 days, about 30 days, or any amount therein in increments of 1 hour, when administered to a subject with a delivery system taught herein. One of skill will appreciate that the half-life of the activity of an active agent that is administered to a subject using a delivery system taught herein can range from about 30 minutes to about 2 days, from about 1 hour to about 36 hours, from about 2 hours to about 20 hours, from about 2 hours to about 10 hours, from about 3 hours to about 30 hours, from about 3 hours to about 15 hours, from about 4 hours to about 40 hours, from about 4 hours to about 20 hours, from about 5 hours to about 50 hours, from about 5 hours to about 25 hours, or any range or any amount therein in increments of 1 hour.

The term "pharmaceutical agent" or "pharmaceutically active agent" can be used interchangeably and refer to any diagnostic and therapeutic substances for use, in vivo, in the diagnosis, cure, treatment, management or prevention of conditions and diseases. In some embodiments, the term "pharmaceutical agent" or "pharmaceutically active agent" can be used interchangeably with the term "drug". In some embodiments, the term "pharmaceutical agent" or "pharmaceutically active agent" can be used interchangeably with the term "imaging agent". And, in some embodiments, the term "pharmaceutical agent" or "pharmaceutically active agent" can be used interchangeably with the term "diagnostic agent".

Figure 3A:
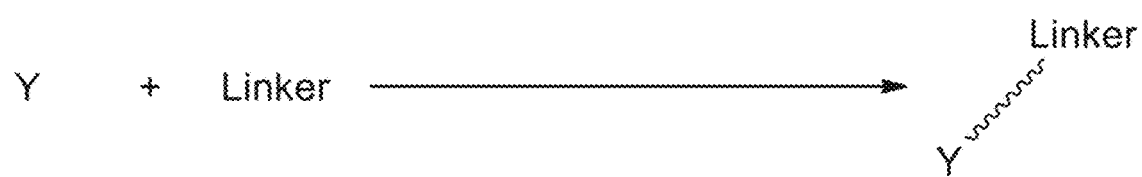
FIGS. 3A-3C illustrate linker-modified AG10 analogs that enhance in vitro and in vivo half-life of peptides, according to some embodiments.
Figure 3B:
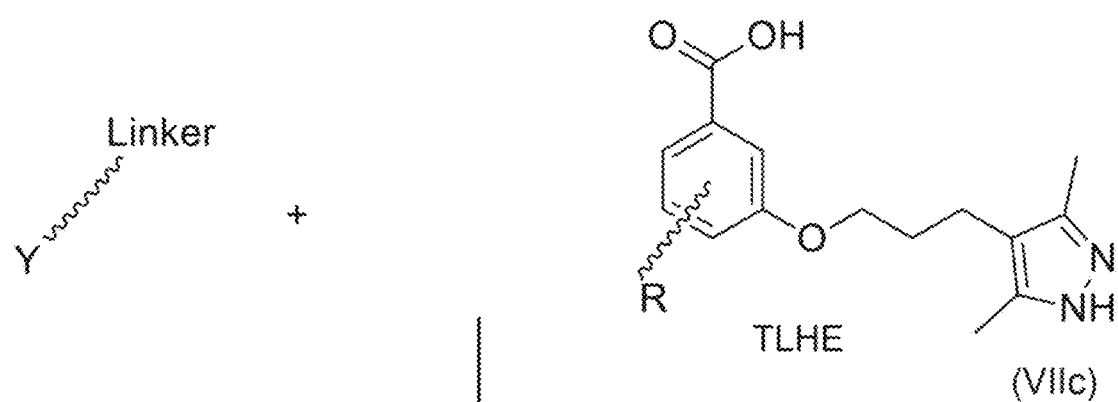
Figure 3C:
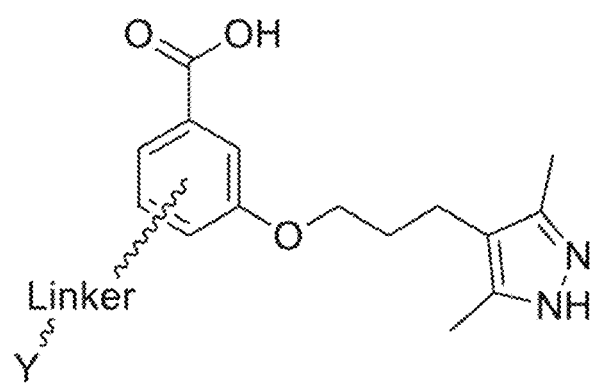

The term "active agent" includes pharmaceuticals agents and pharmaceutically active agents, and can also be used to refer to any substances, diagnostic, therapeutic, or otherwise, for use, in vitro or in silico, for assessing the activity of the agent in the diagnosis, cure, treatment, management or prevention of conditions and diseases. In many embodiments, the molecular weight of an active agent should be at or below about 40,000 Daltons to ensure elimination of the agent from a subject. In some embodiments, the molecular weight of the active agent ranges from about 200 Daltons to about 40,000 Daltons, from about 8,000 Daltons to about 30,000 Daltons, from about 10,000 Daltons to about 20,000 Daltons, or any range therein. In some embodiments, the methods taught herein can further include the administration of an effective amount of an additional active agent or therapeutic treatment, such as the administration of an effective amount of an antiproliferative and/or an effective amount of radiation therapy, for example. In some embodiments, the terms "agent", "bioactive agent", "active agent", and "therapy" can be interchangeable. For example, the administration of radiation can be considered the administration of a second agent, in some embodiments. A bioactive agent can be any moiety capable of contributing to a therapeutic effect, a prophylactic effect, both a therapeutic and prophylactic effect, or other biologically active effect in a subject. A bioactive agent can also have diagnostic properties. The general concept of the delivery system design Generally speaking, the delivery systems taught herein, and conjugated active agents that are delivered by the delivery systems, can be made using any synthesis technique known to one of skill. For example, one can select an active agent, a ligand for a plasma protein, and a linker for attaching the ligand to the active agent. As taught herein, the ligand selected can be specific for TTR, and the linker can be configured to attach the TTR ligand to the active agent. FIGS. 3A-3C illustrate a simplified construction of a delivery systems taught herein, according to some embodiments. As shown in FIG. 3A, a linker is attached to the active agent, Y. In FIG. 3B, a TTR ligand, referred to herein as Compound (VIIIc), is attached to the linker to create the conjugated active agent in FIG. 3C. One of skill will appreciate that the Y group can be any active agent, for example, a peptide, a protein, an oligonucleotide, an oligosaccharide, a virus-like particle, an imaging agent, or a small molecule drug. And, one of skill will appreciate that the linker can be any chemical moiety of the desired length and functionality to position the active agent at a desired location relative to the plasma protein.

Figure 4:
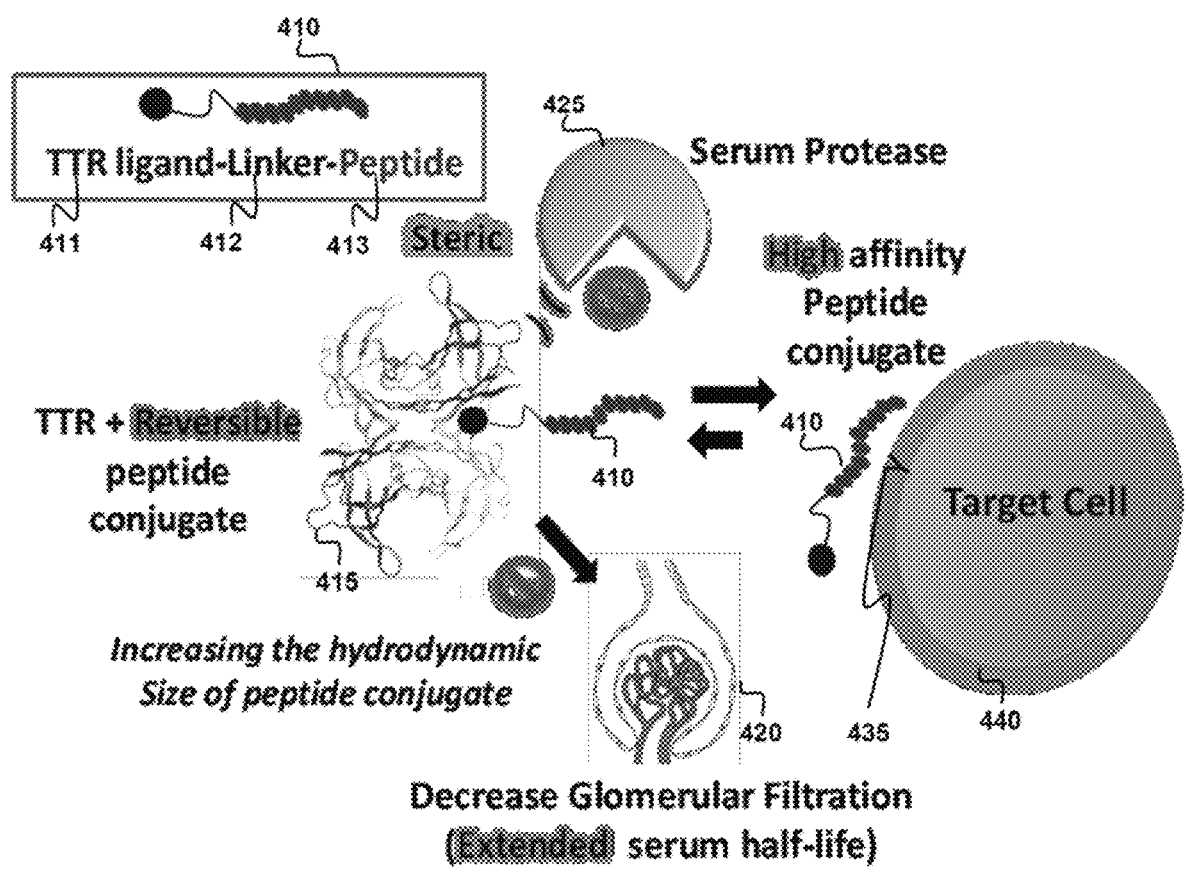
FIG. 4 illustrates a reversible relationship between the conjugated active agent and a plasma protein, according to some embodiments.

FIG. 4 illustrates a reversible relationship between the conjugated active agent and a plasma protein, according to some embodiments. FIG. 4 shows a delivery system 410 taught herein in a reversible relationship with TTR, the delivery system 410 having a conjugated active agent 411, 412,413 with a TTR ligand 411 attached to a linker 412 which is attached to a peptide 413 as the active agent. The association between the plasma protein TTR 415 and the delivery system 410 increases in vivo half-life of the peptide 413 by reducing filtration 420 by the kidneys, for example. In addition, the steric bulk of TTR 415 increases in vivo half-life of the peptide 413 by protecting it against degradation by serum proteases 425. Ideally, the delivery system 410 will preserve the binding affinity of the peptide 413 to its extra-cellular receptor 435 on a target cell 440.

The linker may be connected using any convenient chemical modification chemistries, and the process of selecting the linker chemistry can include the use of any convenient selection method, such as but not limited to, modeling a X-ray crystal structure of TTR (e.g., a co-crystal structure of TTR with a ligand) and selecting one or more appropriate positions which are not involved in contacts with the protein (e.g., solvent exposed positions) which may be readily chemically modified. Further methods include determining whether a modification of interest has an adverse effect of the binding of the recruitment moiety to TTR using an in vitro binding assay.

As used herein, the term "linker", "linkage" and "linking group" refers to a chemical linking moiety that connects two groups and has a backbone of 50 atoms or less in length. In some embodiments, the linker or linkage may be a covalent bond that connects two groups, or a chemical moiety having a chain of between 1 and 50 atoms in length, between 2 and 20 atoms in length, between 3 and 30 atoms in length, between 4 and 40 atoms in length, between 10 and 50 atoms in length, between 10 and 30 atoms in length, between 12 and 26 atoms in length, between 14 and 30 atoms in length, or any range therein in amounts of 1 atom in length. For example, a linker or a portion of a linker can have a length that is 1, 2, 3, 4, 5, 6, 8, 10, 12, 14, 16, 18, 20, 22, 24, 26, 28, 30, 32, 34, 36, 38, 40, 45, or 50 carbon atoms in length, where the linker may be linear, branched, cyclic, or a single atom. In some embodiments, the linker may be 10 angstroms, 11 angstroms, 12 angstroms, 13 angstroms, 14 angstroms, 15 angstroms, 16 angstroms, 17 angstroms, 18 angstroms, 19 angstroms, 20 angstroms, 22 angstroms, 23 angstroms, 24 angstroms, 25 angstroms, 26 angstroms, 27 angstroms, 28 angstroms, 29 angstroms, 30 angstroms, 32 angstroms, 34 angstroms, 36 angstroms, 38 angstroms, 40 angstroms, 45 angstroms, 50 angstroms, or any amount therein in increments of 1 angstrom, in length. In some embodiments, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The linking moiety may be conjugated to the TTR ligand and Y using any convenient functional groups (carboxylic acids, amines, alcohols, carbamates, esters, amide, ethers, thioethers, maleimides, and the like), and linking chemistries. For example, conjugation chemistry described by G. T. Hermanson ("Bioconjugate Techniques", Academic Press, Second Edition, 2008) may be readily adapted for use in preparing the subject heterobifunctional compounds and is hereby incorporated herein by reference in it's entirety.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable salts may also include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Other pharmaceutically acceptable salts include acid salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate; base salts including ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C=C(OR) where R is hydrogen, alkyl, alkenyl, alkynyl, or cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include fluoro, chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $_c4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$F, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The Structure of the Delivery Systems Provided Herein

A delivery system for an active agent can be configured to comprise a ligand with (i) a high selectivity for a plasma protein endogeneous to the subject, the molecular weight of the plasma protein ranging from about 30 kDa to about 80 kDa; (ii) a high binding affinity, Kd, of at least $10^{-6}$ M for the plasma protein; and, (iii) a molecular weight ranging from about 200 Da to about 2000 Da; and, a linker that ranges in length from about 10 angstroms to about 50 angstroms, or from 8 atoms to 50 atoms. The term "active agent" can be used, for example, to refer to a structure selected from the group consisting of a peptide, an oligopeptide, a polypeptide, a protein, an antibody, an oligonucleotide, a polynucleotide, a virus-like particle, a small molecule, an imaging agent, and combinations thereof. The term "plasma protein" can be used to refer to a blood serum protein selected from the group consisting of serum albumin, transferrin, Retinol binding protein, alpha-1 globulins, alpha-2 globulins, beta globulins, and gamma globulins, or a combination thereof. In some embodiments, the plasma protein is HSA. And, in some embodiments, the plasma protein is TTR.

Generally speaking, the delivery system are generally directed to a system comprising a ligand of particular interest which is selective for transthyretin in the serum of a subject; and, a linker configured for operatively attaching the ligand covalently to an active agent. In some embodiments, the linker ranges in length from 14 angstroms to 30 angstroms, or from 10 atoms to 22 atoms. The ligand can have the following structure of Compound (I)

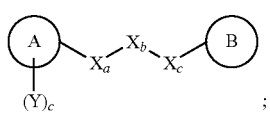
(I)

where $X_a$, $X_b$ and $X_c$ are independently selected from $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

a ring is a 4 to 12-membered ring, in certain embodiments the 4 to 12-membered ring is an aromatic or heteroaromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano;

c is an integer ranging from 0 to 5; and,

B ring is a heterocyclic ring selected from the following (h1-h30):

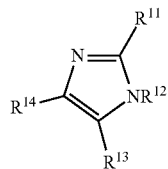
h1

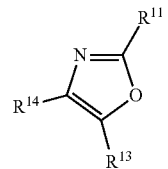
h2

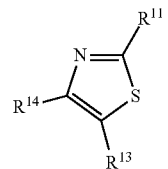
h3

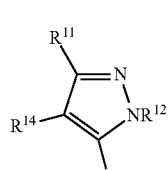
h4

-continued

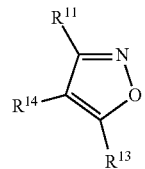
h5

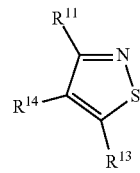
h6

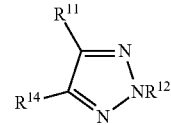
h7

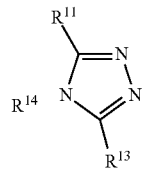
h8

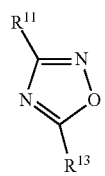
h9

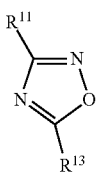
h10

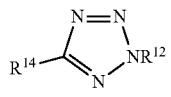
h11

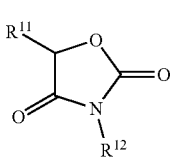
h12

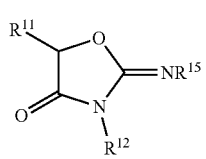
h13

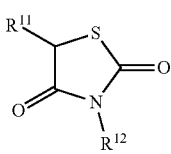
h14

-continued h15 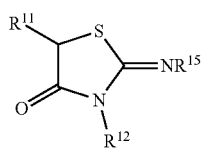

h16 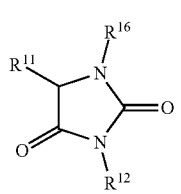

h17 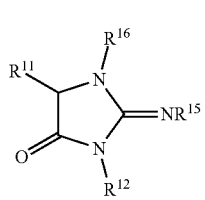

h18 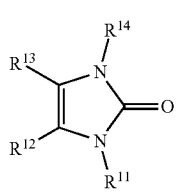

h19 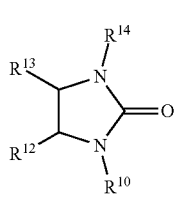

h20 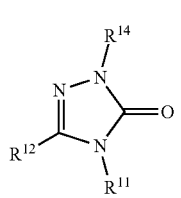

h21 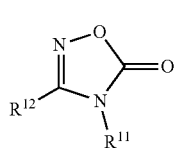

h22 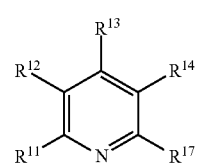

h23 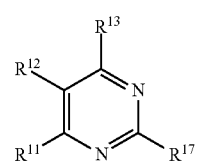

-continued h24 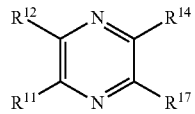

h25 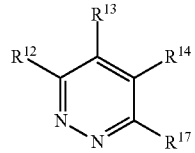

h26 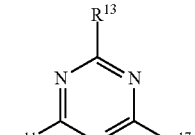

h27 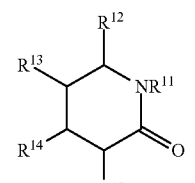

h28 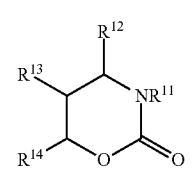

h29 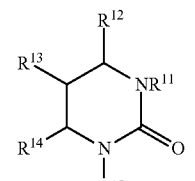

h30 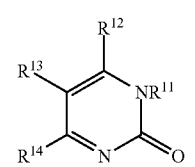

where $R^{11}$—$R^{16}$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano; $R^{17}$ is selected from a hydroxyl, alkyl, amino, and alkyl amino; and at least one of $R^{11}$—$R^{16}$ is the linking group to $X_c$;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand can have the following structure of Compound (II), comprising:

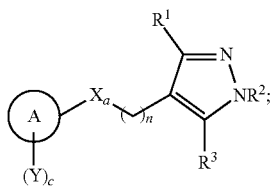

(II)

where, n is an integer ranging from 0 to 8;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

A is a 5 to 12-membered ring, in certain embodiments the 5 to 12-membered ring is an aromatic or heteroaromatic ring; each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and, c is a number from zero to 5;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand has the structure of Compound (III), comprising:

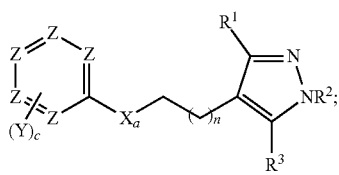

(III)

where, n is an integer ranging from 0 to 7;

Z is carbon and/or up to three of the five Z may be nitrogen;

R1, R2 and R3 are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R4)(R5)$, O, N—R5 or S; where R4 and R5 are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is an integer ranging from 0 to 5;

or, a pharmaceutically acceptable salt, ester, enol ether, enol ester, amide, acetal, ketal, orthoester, hemiacetal, hemiketal, hydrate, solvate or prodrug thereof.

In some embodiments, the ligand of Compound (III) is a structure in which n is 3; and, X is O.

In some embodiments, the ligand has the structure of Compound (IV), comprising:

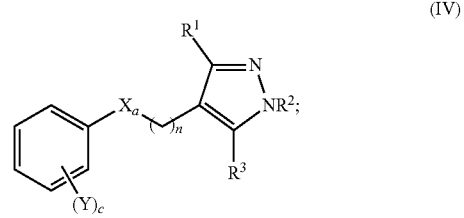

(IV)

where, n is an integer ranging from 1 to 4;

$R^1$ is a short chain alkyl having 1 to 4 carbon atoms;

$R^2$ is hydrogen;

$R^3$ is a short chain alkyl having 1 to 4 carbon atoms;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, halogen, acyl, substituted acyl, carboxyl, heterocyclic group, alkoxycarbonyl sulfonamide, sulfonyl fluoride, thioester and substituted alkoxycarbonyl; and c is 2;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand of Compound (IV) is a structure in which R1 is methyl and R3 is methyl; Xa is O; and, Y is fluoro or carboxyl.

In some embodiments, the ligand has structure of Compound (V), comprising:

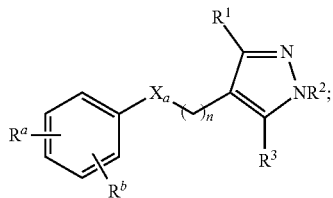

(V)

where,
n is 1 to 8;
R$^1$, R$^2$ and R$^3$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halo, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;
X$_a$ is C(R$^4$)(R$^5$), O, N—R$^5$ or S; where R$^4$ and R$^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;
R$^a$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, CF$_3$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;
R$^b$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, CF$_3$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;
R$^6$ is alkyl, haloalkyl, cycloalkyl, or heterocyclyl;
R$^7$ and R$^8$ are each independently hydrogen, alkyl, alkenyl, alkynyl, cycloalkyl, heterocyclyl, or heteroaryl; and, R$^9$ is the side chain of a naturally occurring α-amino carboxylic acid;
or, a pharmaceutically acceptable salt, ester, enol ether, enol ester, amide, acetal, ketal, orthoester, hemiacetal, hemiketal, hydrate, solvate or prodrug thereof.

In some embodiments, the ligand of Compound (V) is a structure in which R$^b$ is selected from bromo, chloro and fluoro.

In some embodiments, the ligand has the structure of Compound (VI), comprising:

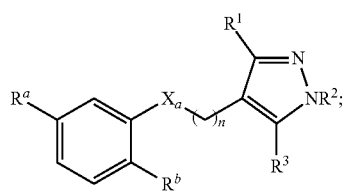

(VI)

where,
n is 3;
R$^1$ is a short chain alkyl having 1 to 4 carbon atoms;
R$^2$ is hydrogen;
R$^3$ is a short chain alkyl having 1 to 4 carbon atoms;
X$_a$ is C(R$^4$)(R$^5$), O, N—R$^5$ or S; where R$^4$ and R$^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;
R$^a$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, hydrogen, an acyl, substituted acyl, carboxyl, alkoxycarbonyl, heterocyclic group, sulfonamide, sulfonyl fluoride, thioester, or substituted alkoxycarbonyl;
R$^b$ is CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, a halogen or heterocyclic group;
R$^6$ is alkyl, haloalkyl, cycloalkyl, or heterocyclyl;
R$^7$ and R$^8$ are each independently hydrogen, alkyl, alkenyl, alkynyl, cycloalkyl, heterocyclyl, or heteroaryl; and
R$^9$ is the side chain of a naturally occurring α-amino carboxylic acid;
or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIc):

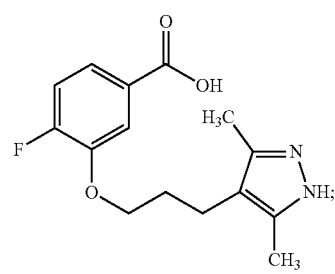

(VIIc)

or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIa), comprising:

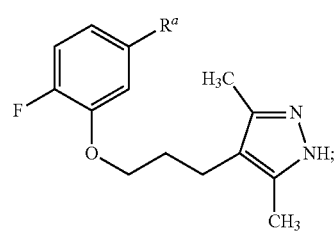

(VIIa)

where, $R^a$ is OH, CHO, COOH, $CONH_2$, CONH(OH), $COOR^6$, $CONHR^6$;

$R^6$ is straight of branched alkyl of 1-3 carbon atoms;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIb), comprising:

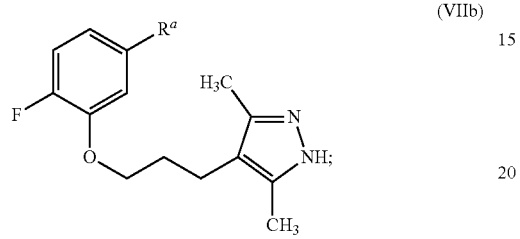

(VIIb)

where, $R^a$ is COOH, $CONH_2$, CONH(OH), $COOR^6$, $CONHR^6$;

$R^6$ is straight of branched alkyl of 1-3 carbon atoms;

or, a pharmaceutically acceptable salt, ester, enol ether, enol ester, acetal, amide, ketal, orthoester, hemiacetal, hemiketal, hydrate, solvate or prodrug thereof.

In some embodiments, the ligand is selected from the group consisting of:

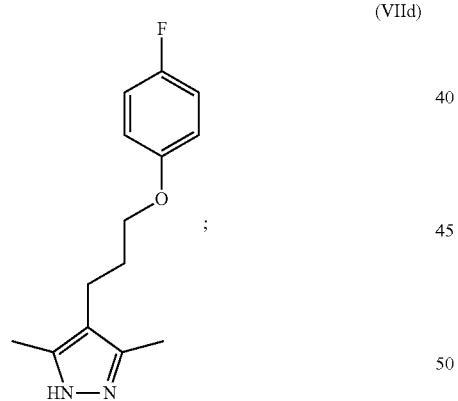

(VIId)

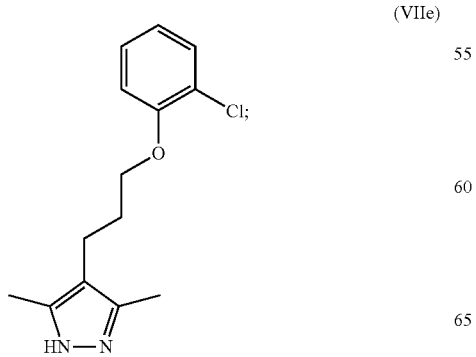

(VIIe)

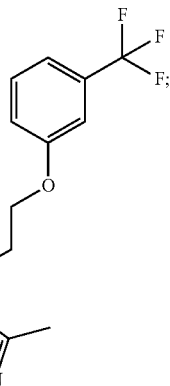

(VIIf)

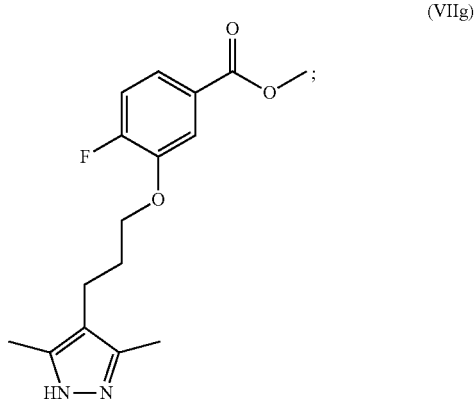

(VIIg)

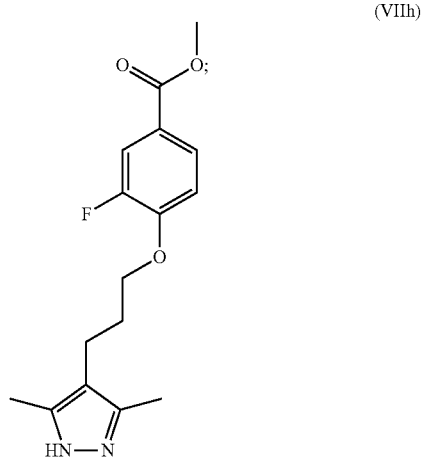

(VIIh)

(VIIi)
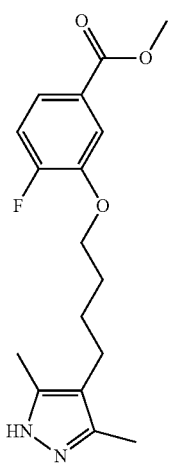
(VIIj)
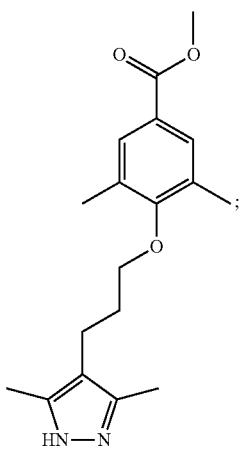
(VIIk)
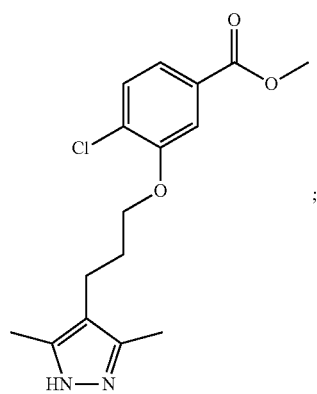
(VIII)
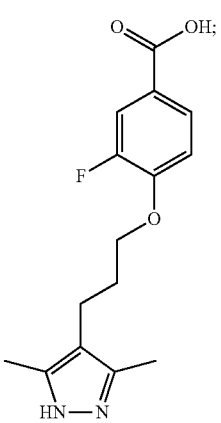
(VIIm)
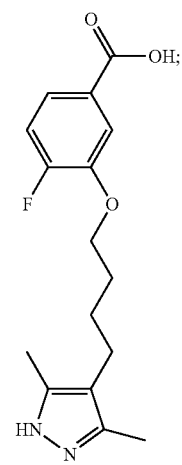
(VIIn)
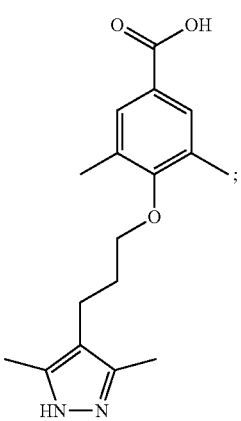

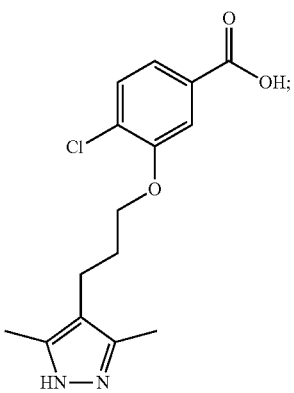
(VIIo)

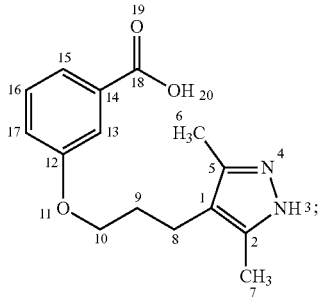
(VIIIc)

or, a pharmaceutically acceptable salt, ester, enol ether, enol ester, acetal, amide, ketal, orthoester, hemiacetal, hemiketal, hydrate, solvate or prodrug thereof; and, the linker is attached to the ligand ortho at C15 to the carboxyl group at C14.

In some embodiments, the ligand has the structure of Compound (VIIIc):

(VIIIa)

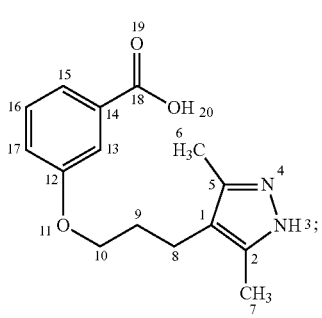
(VIIIc)

or, a pharmaceutically acceptable salt, ester, enol ether, enol ester, acetal, amide, ketal, orthoester, hemiacetal, hemiketal, hydrate, solvate or prodrug thereof; and, the linker is attached to the ligand meta at $C_{16}$ to the carboxy carbon at $C_{14}$.

Uses and Methods of Administration

The delivery systems provided herein can provide a therapeutic and/or prophylactic effect in the treatment of a disease, or ameliorization of one or more symptoms of a disease in a subject. The term "subject" and "patient" are used interchangeably and refer to an animal such as a mammal including, but not limited to, non-primates such as, for example, a cow, pig, horse, cat, dog, rabbit, rat and mouse; and primates such as, for example, a monkey or a human.

Methods of increasing the in vivo half-life of an active agent are provided, the methods comprising covalently attaching any of the delivery systems taught above to an active agent.

Method of administering an active agent to a subject are provided, the methods comprising covalently attaching any of the delivery systems taught above to an active agent to create a conjugated active agent; and, administering the conjugated active agent to the subject.

Methods of reducing the immunogenicity of an active agent in a subject are provided, the methods comprising obtaining a delivery system having a ligand with (i) a high selectivity for a plasma protein endogenous to the subject, the molecular weight of the plasma protein ranging from (VIIIb)

and, a pharmaceutically acceptable salt, ester, enol ether, enol ester, acetal, amide, ketal, orthoester, hemiacetal, hemiketal, hydrate, solvate or prodrug thereof.

In some embodiments, the ligand has the structure of Compound (VIIIc):

about 30 kDa to about 80 kDa; (ii) a high binding affinity, Kd, of at least $10^{-6}$ M for the plasma protein; and, (iii) a molecular weight ranging from about 200 Da to about 2000 Da; and, a linker that ranges in length from about 10 angstroms to about 50 angstroms, or from 10 atoms to 50 atoms. The method also includes covalently attaching the delivery system to an active agent to create a conjugated active agent; and, administering the conjugated active agent to the subject; wherein, the plasma protein shields the active agent from antibody generation in the subject after the administering.

In some embodiments, the delivery system can be any of the delivery systems taught above. In some embodiments, the plasma protein can be selected from the group consisting of serum albumin, transferrin, Retinol binding protein, alpha-1 globulins, alpha-2 globulins, beta globulins, and gamma globulins, or a combination thereof. In some embodiments, the plasma protein is HSA. And, in some embodiments, the plasma protein is TTR.

Moreover, it should be appreciated that the active agent can be any active agent known to one of skill that can benefit from the delivery systems taught herein. In some embodiments, the active agent comprises a structure selected from the group consisting of a peptide, an oligopeptide, a polypeptide, a protein, an antibody, an oligonucleotide, a polynucleotide, a virus-like particle, a small molecule, an oligosaccharide, an imaging agent, and combinations thereof.

Formulations

The delivery systems disclosed herein can be formulated into pharmaceutical compositions by combining them with appropriate, pharmaceutically acceptable carriers, diluents, excipients, and/or adjuvants. The formulations can be administered by any route known to one of skill including, but not limited to, oral, parenteral, transdermal, intrathecal, ophthalmic, topical, pulmonary, nasal, rectal, or depot administration.

The delivery systems, for example, can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Generally speaking, the compounds described above can be formulated into pharmaceutical compositions using techniques and procedures well known in the art (see, e.g., Ansel Introduction to Pharmaceutical Dosage Forms, Fourth Edition 1985, 126). In some embodiments, the compounds are formulated into suitable pharmaceutical preparations for oral administration to a subject.

In some embodiments, the delivery systems are mixed with a suitable pharmaceutical carrier. And, any component of the delivery systems can be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the conjugated active agents that are administered with the delivery systems are delivered in an effective amount that treats, prevents, or ameliorates one or more of the symptoms of diseases or disorders treated.

The bioactive agents include, but are not limited to, small molecules, nucleotides, oligonucleotides, polynucleotides, amino acids, oligopeptides, polypeptides, and proteins. Bioactive agents can include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin 11, actinomycin X1, actinomycin C1, and dactinomycin (Cosmegen®, Merck & Co., Inc.). Antineoplastics or antimitotics include, for example, paclitaxel (TAXOL, Bristol-Myers Squibb Co.), docetaxel (TAXOTERE, Aventis S.A.), methotrexate, irinotecan, SN-38, azathioprine, vincristine, vinblastine, fluorouracil, doxorubicin hydrochloride (ADRIAMYCIN, Pfizer, Inc.) and mitomycin (MUTAMYCIN, Bristol-Myers Squibb Co.), and any prodrugs, codrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX, Biogen, Inc.), and any prodrugs, codrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINVIL and PRINZIDE, Merck & Co., Inc.); calcium channel blockers such as nifedipine; colchicines; fibroblast growth factor (FGF) antagonists, fish oil (omega 3-fatty acid); histamine antagonists; lovastatin (MEVACOR, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, codrugs, metabolites, analogs, homologues, congeners, derivatives, salts and combinations thereof. Antiallergic agents include, but are not limited to, pemirolast potassium (ALAMAST, Santen, Inc.), and any prodrugs, codrugs, metabolites, analogs, homologues, congeners, derivatives, salts and combinations thereof.

Antibody therapy provides additional bioactive agents that may be useful when administered in combination with the methods taught herein. AVASTATIN, for example, is a human monoclonal antibody to VEGF, has provided beneficial results in colorectal cancer, increasing survival time by more than 30% when used in combination with the standard Saltz regime of irinotecan, 5-fluorouracil, and leucovorin. One of skill will appreciate that several monoclonal antibodies would be useful, the following providing further examples:

TABLE

| mAb name | Trade name | Cancer treated: |
|---|---|---|
| rituximab | RITUXAN | non-Hodgkin lymphoma |
| trastuzumab | HERCEPTIN | breast cancer |
| gemtuzumab ozogamicin* | MYLOTARG | acute myelogenous leukemia (AML) |

TABLE-continued

| mAb name | Trade name | Cancer treated: |
|---|---|---|
| alemtuzumab | CAMPATH | chronic lymphocytic leukemia (CLL) |
| ibritumomab tiuxetan* | ZEVALIN | non-Hodgkin lymphoma |
| tositumomab* | BEXXAR | non-Hodgkin lymphoma |
| cetuximab | ERBITUX | colorectal cancer; head & neck cancers |
| bevacizumab | AVASTIN | colorectal cancer; non-small cell lung cancer; breast cancer; glioblastoma; kidney cancer |
| panitumumab | VECTIBIX | colorectal cancer |
| ofatumumab | ARZERRA | chronic lymphocytic leukemia (CLL) |

*refers to a conjugated monoclonal antibody

It should be appreciated that, a bioactive agent can be given alone or in combination with other bioactive agents, with the compositions and methods taught herein. Chemotherapy drugs, for example, are sometimes most effective when given in combination, as a combination chemotherapy regime. The rationale for combination chemotherapy is to use drugs that work by different mechanisms of action, thereby decreasing the likelihood that resistant cancer cells will develop. When drugs having different effects are combined, each drug can be used at its optimal dose, sometimes without, and sometimes reducing, intolerable side effects.

The active agent can be included, for example, in a pharmaceutically acceptable carrier, the active agent conjugated with the delivery system in an amount sufficient to exert a therapeutically useful effect in the absence of undesirable side effects on the patient treated. The therapeutically effective concentration may be determined empirically by testing the compounds in in vitro and in vivo systems described and then extrapolated therefrom for dosages for humans.

Consistent with the purpose of the delivery systems, e.g., increasing half-life of the active agent, the concentration of active agent administered will depend on absorption, inactivation and excretion rates of the active compound, the physicochemical characteristics of the compound, the dosage schedule, and amount administered as well as other factors known to those of skill in the art.

The delivery systems provided herein can be administered to a subject using any manner of administration known to one of skill. For example, in some embodiments, a localized administration is used and, in some embodiments a systemic administration is used. In some embodiments, a combination of system and local administration is used. One of skill will appreciate that the therapeutic program selected, the agents administered, the condition of the subject, and the effects desired, can affect the administration schedule and program used.

One of skill understands that the amount of the agents administered can vary according to factors such as, for example, the type of disease, age, sex, and weight of the subject, as well as the method of administration. For example, local and systemic administration can call for substantially different amounts to be effective. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" refer to a method of incorporating a composition into the cells or tissues of a subject, either in vivo or ex vivo to diagnose, prevent, treat, or ameliorate a symptom of a disease. In one example, a compound can be administered to a subject in vivo parenterally. In another example, a compound can be administered to a subject by combining the compound with cell tissue from the subject ex vivo for purposes that include, but are not limited to, assays for determining utility and efficacy of a composition. When the compound is incorporated in the subject in combination with one or active agents, the terms "administration" or "administering" can include sequential or concurrent incorporation of the compound with the other agents such as, for example, any agent described above. A pharmaceutical composition of the invention is formulated to be compatible with its intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

An "effective amount" of a compound of the invention can be used to describe a therapeutically effective amount or a prophylactically effective amount. An effective amount can also be an amount that ameliorates the symptoms of a disease. A "therapeutically effective amount" refers to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount may need to be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition. The term "treating" refers to the administering one or more therapeutic or prophylactic agents taught herein.

A "prophylactically effective amount" refers to an amount that is effective at the dosages and periods of time necessary to achieve a desired prophylactic result such as, preventing, inhibiting, or reversing angiogenesis, tumor growth, or tumor invasion. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

The administration can be local or systemic. In some embodiments, the administration can be oral. In other embodiments, the administration can be subcutaneous injection. In other embodiments, the administration can be intravenous injection using a sterile isotonic aqueous buffer. In another embodiment, the administration can include a solubilizing agent and a local anesthetic such as lignocaine to ease discomfort at the site of injection. In other embodiments, the administrations may be parenteral to obtain, for example, ease and uniformity of administration.

The compounds can be administered in dosage units. The term "dosage unit" refers to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects.

The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, the carrier is suitable for parenteral administration. In other embodiments, the carrier can be suitable for intravenous, intraperitoneal, intramuscular, sublingual or oral administration. In other embodiments, the pharmaceutically acceptable carrier may comprise pharmaceutically acceptable salts.

Pharmaceutical formulations for parenteral administration may include liposomes. Liposomes and emulsions are delivery vehicles or carriers that are especially useful for hydrophobic drugs. Depending on biological stability of the therapeutic reagent, additional strategies for protein stabilization may be employed. Furthermore, one may administer the drug in a targeted drug delivery system such as, for example, in a liposome coated with target-specific antibody. The liposomes can be designed, for example, to bind to a target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a high drug concentration. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect active compounds against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer (PLG), and the like. Such formulations can generally be prepared using methods known to one of skill in the art.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, a sterile and injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, the extract may be prepared in combination with one or more additional compounds that enhance the solubility of the extract.

In some embodiments, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In some embodiments, a therapeutically or prophylactically effective amount of a composition may range in concentration from about 0.001 nM to about 0.10 M; from about 0.001 nM to about 0.5 M; from about 0.01 nM to about 150 nM; from about 0.01 nM to about 500 µM; from about 0.01 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is assumed to average about 70 kg.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

The teachings herein encompass sustained release formulations for the administration of one or more agents. In some embodiments, the sustained release formulations can reduce the dosage and/or frequency of the administrations of such agents to a subject.

The compositions can be administered as a pharmaceutical formulation by injection. In some embodiments, the formulation can comprise the extract in combination with an aqueous injectable excipient. Examples of suitable aqueous injectable excipients are well known to persons of ordinary skill in the art, and they, and the methods of formulating the formulations, may be found in such standard references as Alfonso A R: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as solution of mannitol or other sugars, or a solution of glycine or other amino acids.

Typically, a composition taught herein can be administered by subcutaneously, intramuscularly, intraperitoneally, or intravenously, injecting. A localized administration can, in some embodiments, include direct injection of an agent into the region of the tissue to be treated such as, for example, a solid tumor. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.0001% to about 10% (w/w), from about 0.01% to about 1%, from about 0.1% to about 0.8%, or any range therein, with the remainder comprising the excipient or excipients.

In some embodiments, the composition can be administered in conjunction with at least one other therapeutic agent for the disease state being treated, especially another agent capable of treating cancer such as, for example, a chemotherapeutic agent. The amounts of the agents needed can be reduced, even substantially, such that the amount of the agent or agents required is reduced to the extent that a significant response is observed from the subject. A significant response can include, but is not limited to, a reduction or elimination of nausea, a visible increase in tolerance, a faster response to the treatment, a more selective response to the treatment, or a combination thereof.

The methods can further comprise the administration of an effective amount of an antiproliferative, an effective amount of radiation therapy, surgical therapy, or a combination thereof. The teachings are also directed to a method of treating a cancer. In some embodiments, the method comprises administering an agent to a subject in need of a cancer treatment, wherein the dose of the agent is selected to reduce or eliminate an immunosuppression that would otherwise occur when administering a substantially higher dose of the agent in the subject; and administering radiation therapy in combination with the agent, wherein the reduction or elimination of the immunosuppression enhances the efficacy of the radiation therapy when compared to the efficacy of the radiation therapy otherwise observed when administered in combination with the substantially higher dose of the agent in the subject. In some embodiments, the agent comprises one or more chemotherapeutic agents in combination with the agents provided herein. In these embodiments, the agent can be selected from the group consisting of dacarbazine, paclitaxel, doxorubicin, or a combination thereof.

In some embodiments, an effective amount can range, for example, from about 1 mg/day to about 1000 mg/day, from about 10 mg/day to about 500 mg/day, from about 50 mg/day to about 250 mg/day, or any range therein, for a human of average body mass. For treating a solid tumor, a similar amount will be therapeutically effective. A person of ordinary skill in the art will be able without undue experimentation, having regard to that skill and this disclosure, to determine a therapeutically effective amount of the compositions of this invention for a given disease.

In some embodiments, G-CSF is administered in combination with a composition taught herein using any amount, time, and method of administration known to be effective by one of skill. The G-CSF can be NEUPOGEN, for example, administered in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein.

In some embodiments, the radiation therapy can be administered in a single, localized high-dose ranging, for example, from about 20 Gy to about 100 Gy. In some embodiments, the radiation therapy can be administered in a total dose ranging from about 20 Gy to about 100 Gy using a modified hypofractionation regime of dosing comprising from about 2 doses to about 5 doses during a time frame of one week. In some embodiments, the radiation therapy can be administered in a total dose ranging from about 20 Gy to about 100 Gy using a modified hypofractionation regime of dosing comprising from 2 doses to 3 doses during a time frame ranging from about 2 days to about 3 days. The radiation therapy can also be administered in a total dose ranging from about 45 Gy to about 60 Gy using a modified hypofractionation regime of dosing comprising administering a single dose ranging from about 15 Gy to about 20 Gy for each day during a 3-day time frame.

The compositions and therapies taught herein can be administered in combination. For example, the combinations can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Articles of Manufacture

The present invention provides for articles of manufacture that encompass finished, packaged and labelled pharmaceutical products. The articles of manufacture include the appropriate unit dosage form in an appropriate vessel or container such as, for example, a glass vial or other container that is hermetically sealed. In the case of dosage forms suitable for parenteral administration, the active ingredient, e.g. one or more agents including an extract taught herein, is sterile and suitable for administration as a particulate-free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In other embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. In other embodiments, the articles of manufacture may also include instructions for using the composition as a prophylactic, therapeutic, or ameliorative treatment for the disease of concern.

In other embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising an extract as taught herein within the packaging material, along with a second composition comprising a second agent such as, for example, a glycosaminoglycan, phospholipid, poly(alkylene glycol), any other bioactive agent taught herein, or any prodrugs, codrugs, metabolites, analogs, homologues, congeners, derivatives, salts and combinations thereof. In other embodiments, the articles of manufacture may also include instructions for using the composition as a diagnostic, prophylactic, therapeutic, or ameliorative treatment for the disease of concern.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

EXAMPLES

Example 1. Binding to TTR Prolongs the In Vitro and In Vivo Half-Life of AG10 (VIIc)

Figure 5A:
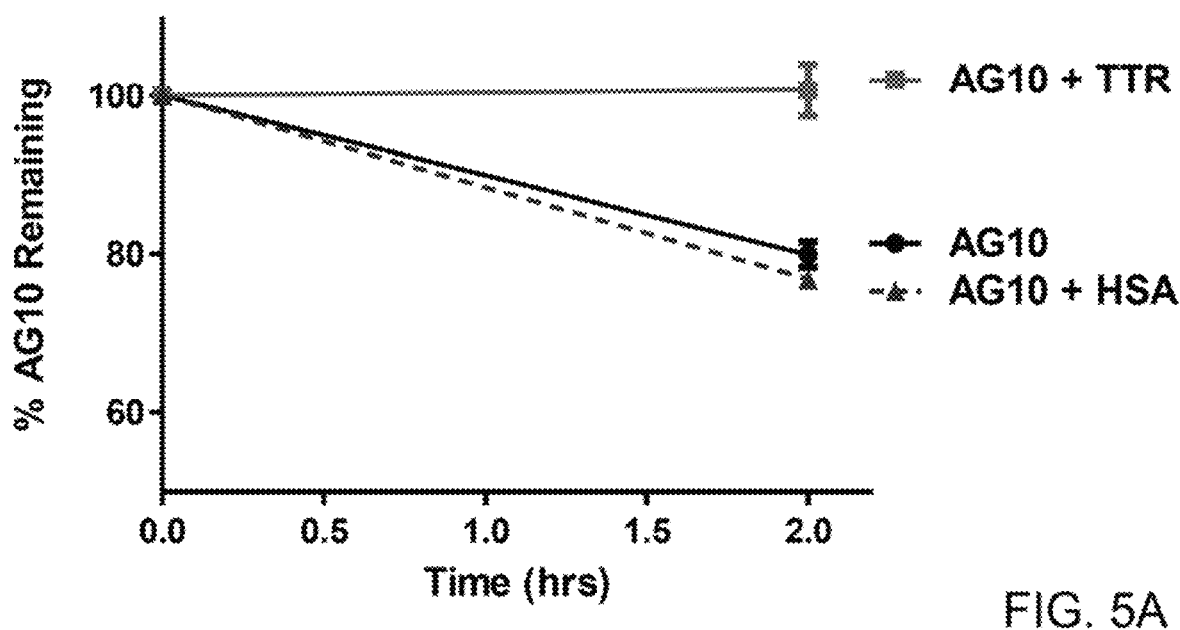
FIGS. 5A and 5B show that (i) incubation of AG10 with hTTR enhances stability against metabolism by human liver microsomes, and (ii) intravenous administration of increasing doses of AG10 to rats (5, 20, and 50 mg/kg) results in increasing concentration of AG10 in rat plasma after 5 min, according to some embodiments.
Figure 5B:
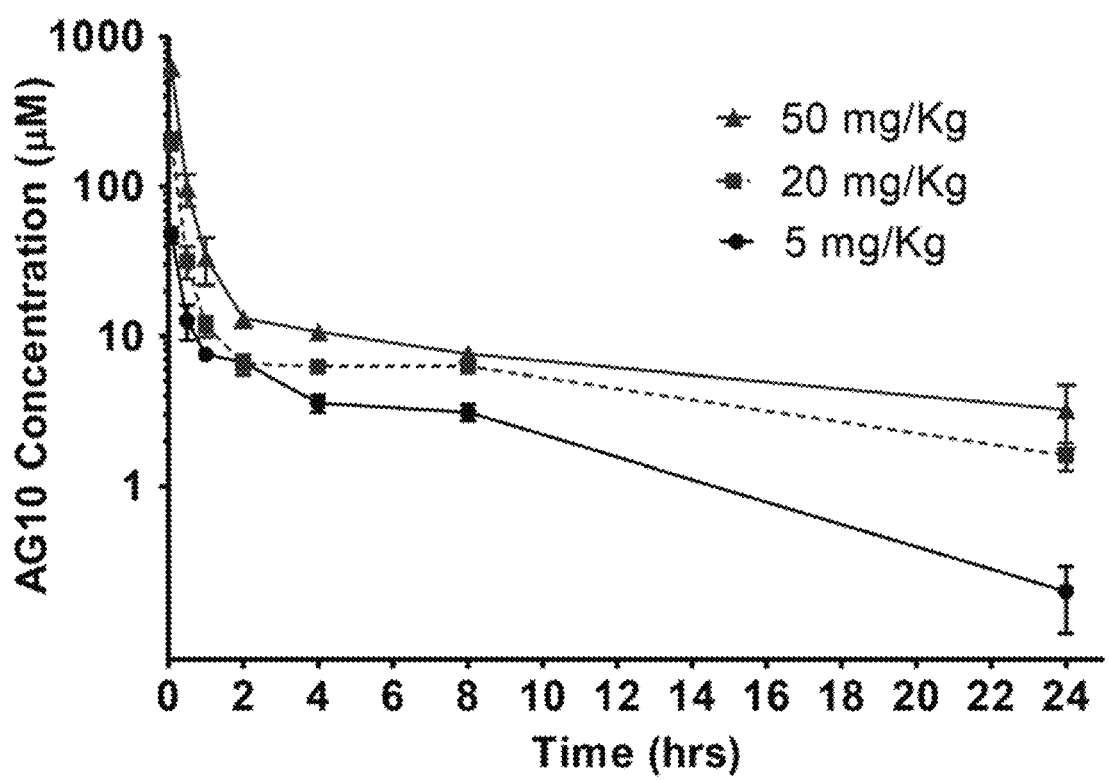

FIGS. 5A and 5B show that (i) incubation of AG10 with hTTR enhances stability against metabolism by human liver microsomes, and (ii) intravenous administration of increasing doses of AG10 to rats (5, 20, and 50 mg/kg) results in increasing concentration of AG10 in rat plasma after 5 min, according to some embodiments.

A. In Vitro Experiment:

We found that the in vitro microsomal half-life of AG10 is significantly enhanced in the presence of hTTR. As shown in FIG. 5A, the % AG10 remaining after 2 hrs was as follows: AG10 pre-incubated with TTR was 96%; AG10 alone was 79%, and AG10 pre-incubated with human serum albumin (HSA) was 77%.

B. In Vivo Experiment:

Intravenous administration of increasing doses of AG10 to rats (5, 20, and 50 mg/kg) resulted in increasing plasma concentration of AG10 (concentrations at 5 min are 47±6 μM, 200±30 μM, and 620±80 μM, respectively). As shown in FIG. 5B, at concentrations>10 μM, AG10 saturates rTTR binding sites with the remaining free AG10 available for distribution into tissue. This is illustrated by initial rapid decline in AG10 total plasma concentration (initial half-life=5-20 min). When the concentration of AG10 reached ~10 μM (similar to serum rTTR concentration), there was a major decrease in AG10 elimination. The terminal elimination phase (the second phase of the biphasic profile) has a much shallower slope and therefore longer elimination half-life (terminal half-life=550 min). The biphasic pharmacokinetic profiles for AG10, in addition to knowledge about the high selectivity of AG10 to TTR (~1:1 binding), are characteristic of target-mediated drug disposition (TMDD). These experiments indicate that the extended in vivo half-life of AG10 is mainly due to its binding to rTTR in rat plasma. As shown in FIG. 5B, intravenous administration of increasing doses of AG10 to rats (5, 20, and 50 mg/kg) resulted in increasing concentration of AG10 in rat plasma after 5 min. Interestingly, the concentration of AG10 after 24 hours was similar for all the doses (~5 μM). These two experiments show that the extended half-life of AG10 is due to its binding to rTTR in rats' plasma (plasma concentration of TTR in rat is similar to human (~5 μM).

Example 2. Development of (AG10)-(Linkers) (Also Referred to as "TTR Ligands for Half-Life Extension "TLHEs")

Figures 2A, 2B:
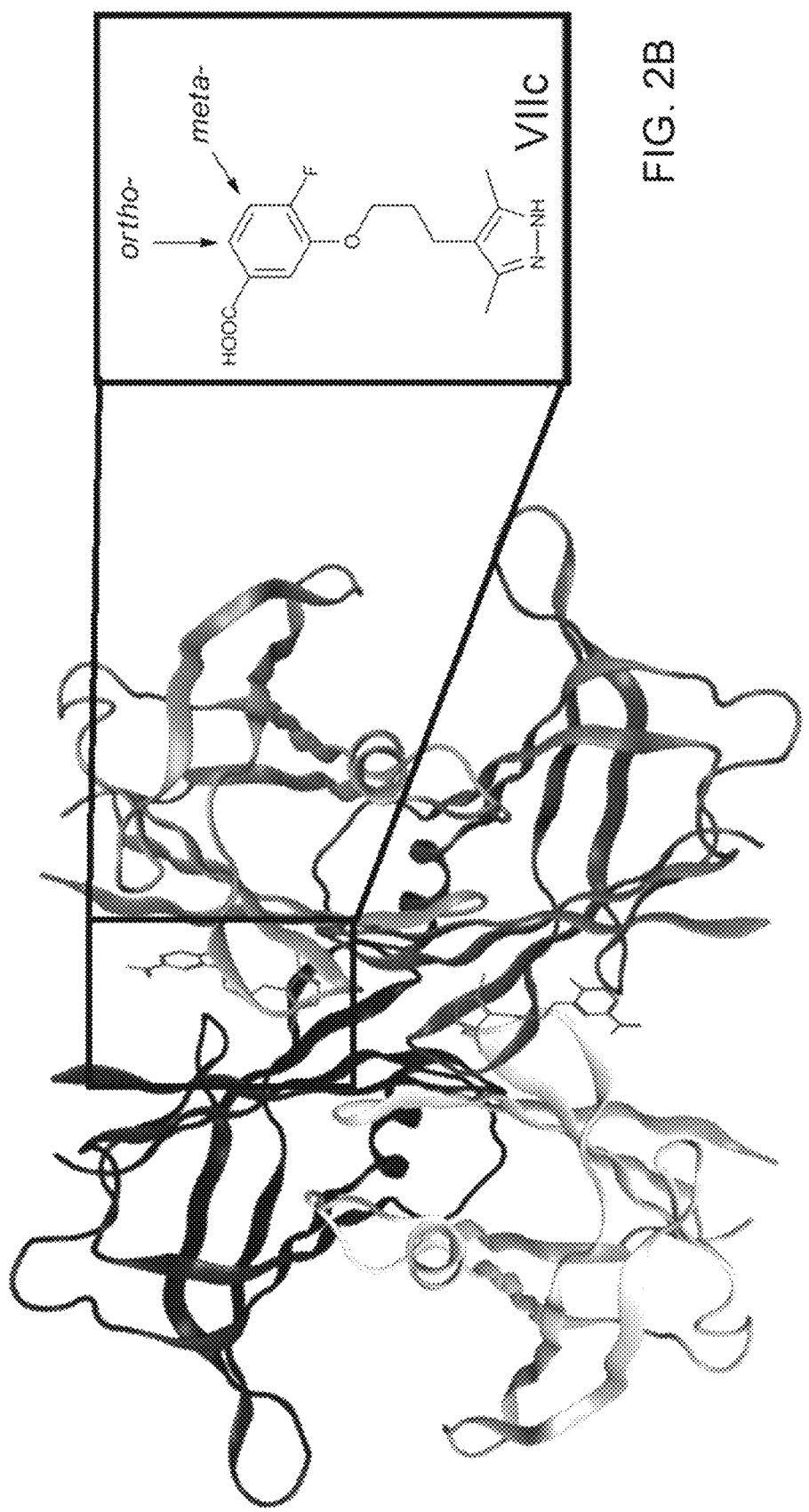
FIGS. 2A and 2B illustrate the structure of hTTR bound to AG10 (Compound VIIc) and the structure of AG10 with potential sites for linker attachment are labeled as ortho & meta, according to some embodiments.

The fluorine atom of AG10 (VIIc) does not make major interaction with TTR. Therefore, we removed the fluorine atom from AG10 to give compound VIIIc. Compound VIIIc displayed a very good binding affinity to hTTR in buffer ($K_d$=22 nM) and selectivity to hTTR in human serum (95±0.2% hTTR binding). Based on the AG10-hTTR crystal structure (FIG. 2A), there are two positions on the phenyl ring that could potentially be utilized for this purpose (i.e. ortho- and meta-positions-relative to the carboxyl group, FIG. 2B). These two positions are not involved in any significant interactions within the hTTR $T_4$ pocket. Importantly, the two positions are pointing out towards the solvent and therefore attaching a linker will project it outside of the $T_4$ binding pocket without major steric clashes with residues at the periphery of the $T_4$ pocket. We successfully developed linker-modified AG10 analogs that we term TTR ligands for half-life extension, TLHEs (FIG. 3).

Example 3. Determine the Optimal Linker Length that Will Preserve the Maximum Binding Affinity and Selectivity of (AG10)-(Linker)-(Active Agent) Conjugates to TTR in Serum The linker length is also very important. If the linker is too short, the peptide will sterically hinder the binding of the AG10 part of the conjugate to hTTR. Our in silico modeling studies indicate that a linker length of ~20 Å (the distance from the phenyl ring carbon of AG10 to residues at the outermost of the binding pockets) is sufficient to clear the $T_4$ binding site and allow the terminal end of the linker to be modified with the desired peptide without affecting the conjugate binding to hTTR. We also synthesized linkers that are shorter (10-18 Å) and also longer (22 and 30 Å) than the 20 Å length predicted by modeling.

Figure 6A:
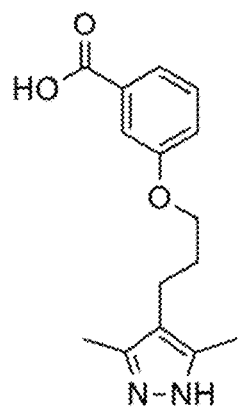
FIGS. 6A-6D illustrate chemical structures of compound VIIIc and designed hTTR ligands for half-life extension (TLHEs): TLHE1, TLHE2, and TLHE3, according to some embodiments.
Figure 6B:
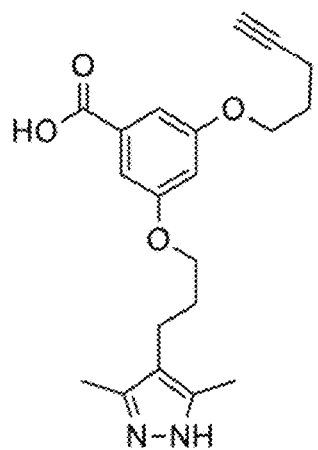
Figure 6C:
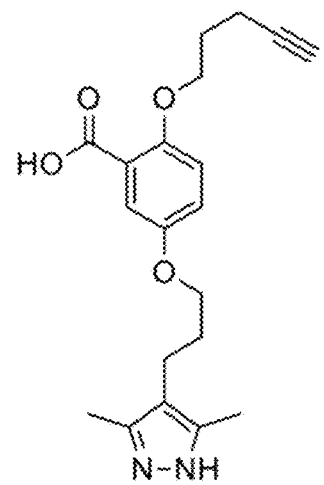
Figure 6D:
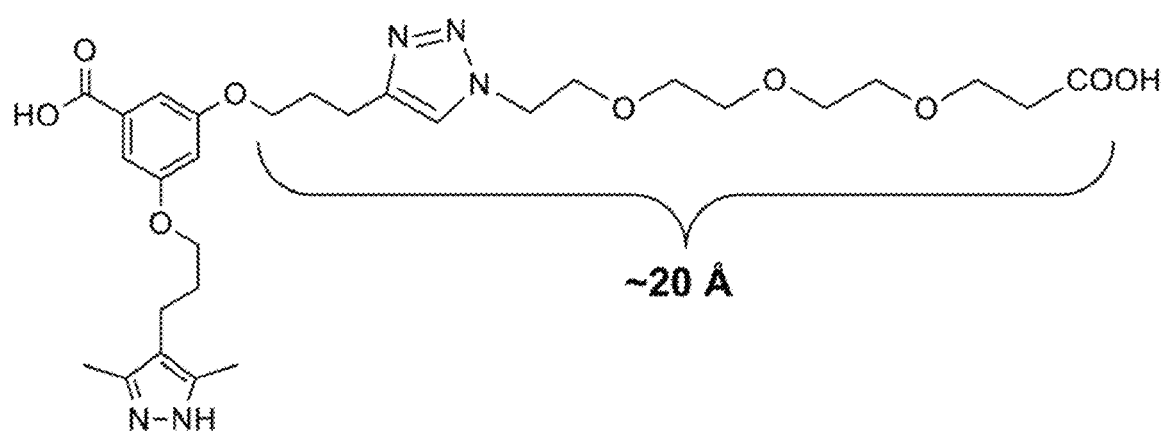

FIGS. 6A-6D illustrate chemical structures of compound VIIIc and designed hTTR ligands for half-life extension (TLHEs): TLHE1, TLHE2, and TLHE3, according to some embodiments. FIG. 6A shows compound VIIIc. FIG. 6B illustrates an alkyne functionalized short linker attached to the meta-position (TLHE1). The terminal end of the linker on TLHE1 can be functionalized with an alkyne group that would be coupled through "click" reaction to an azide modified peptide). FIG. 6C illustrates an alkyne functionalized short linker attached to the ortho-position (TLHE2) of VIIIc. FIG. 6D illustrates a linker length of ~20 Å which should be sufficient to clear out of the hTTR T4 binding sites and potentially be functionalized with peptides (TLHE3).

Figure 7:
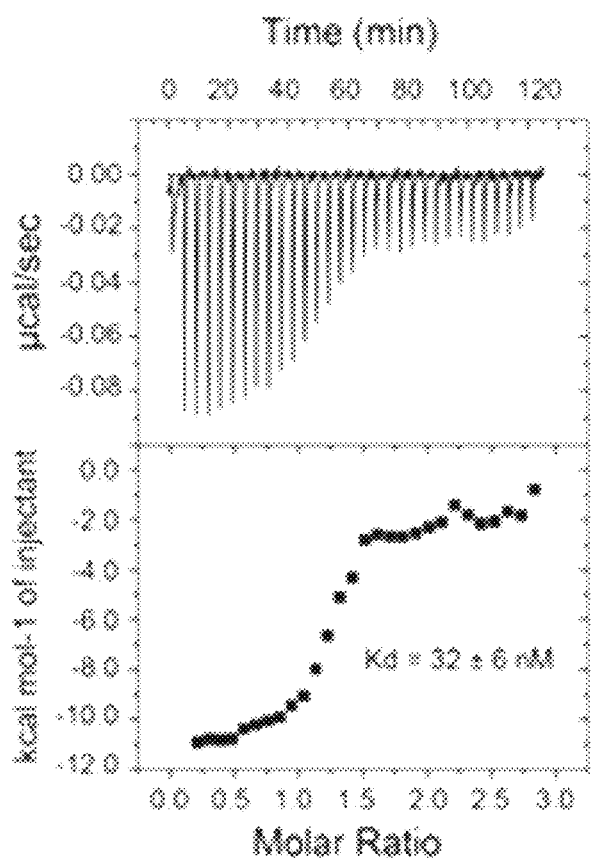
FIG. 7 shows the binding affinity of TLHE1 to TTR, according to some embodiments.

FIG. 7 shows the binding affinity of TLHE1 to TTR, according to some embodiments. Calorimetric titration (ITC) of TLHE1 against hTTR ($K_d$=32±6 nM). Raw data (Upper) and integrated heats (Lower) from the titration of hTTR (2 μM) with TLHE1 (25 μM). One of skill will appreciate that TLHE1 shows a very good binding affinity in FIG. 7.

Figure 8:
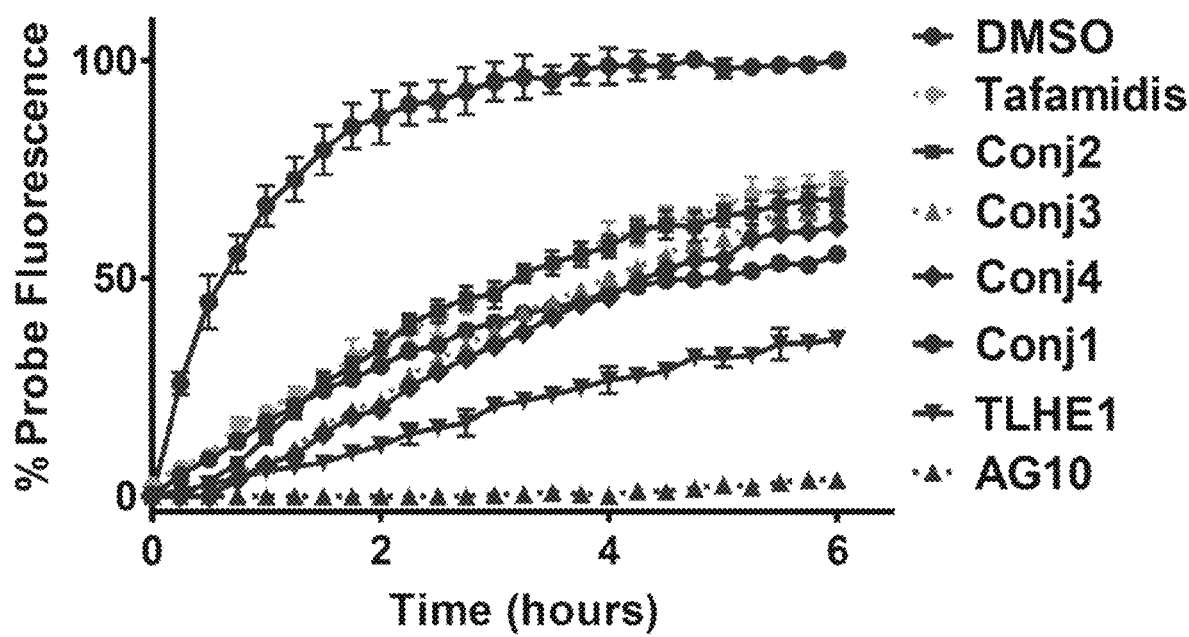
FIG. 8 illustrates the change in fluorescence caused by modification of hTTR in human serum by covalent-probe in the presence of test compounds, according to some embodiments.

FIG. 8 illustrates the change in fluorescence caused by modification of hTTR in human serum by covalent-probe in the presence of test compounds, according to some embodiments. We have tested the selectivity of our ligands to TTR in human serum using this selectivity assay. Fluorescence change caused by modification of hTTR in human serum (hTTR conc. ~5 μM) by covalent-probe monitored for 6 h in the presence of covalent-probe alone (DMSO) or covalent-probe and hTTR ligands (10 μM). The lower the binding and fluorescence of covalent-probe, the higher binding selectivity of ligand to hTTR. Each bar shows the mean (±SD) of three replicates. One of skill will appreciate that TLHE1 shows a very good selectivity in FIG. 8.

Example 4. Chemical Synthesis of AG10-Alkyne Linkers

We have designed a general synthetic route for the AG10-alkyne linkers. The first step was attaching the alkyne linker (after activating the alcohol with p-TsCl) to one of the equivalent phenolic hydroxyl groups on methyl-3,5-dihydroxybenzoate (generating the building block for the linker at the meta-position). For the ortho-position, we used methyl-2,5-dihydroxybenzoate. Additional protection of the 5-OH group using MOM ether was needed before attaching the linker at the 2-(ortho)-position. The following steps in the synthesis are similar to what we reported recently for AG10 synthesis. The alkyne linker was used to control the length of the overall conjugate linker. The advantage of our synthetic strategy is that it will allow for inexpensive generation of various AG10-alkyne linkers in few synthetic steps. By following this approach, we have successfully synthesized compound TLHE1 (C5-alkyne linker conjugated to the meta-positions of VIIIc; n=3) and TLHE2 (C5-alkyne linker conjugated to the ortho-positions of VIIIc). All synthetic compounds were purified by chromatography and the chemical structures of TLHE1 and TLHE2 were confirmed by $^1$H NMR, $^{13}$C NMR and mass spectrometry and the purity (>95%) was confirmed by HPLC.

Example 5. Synthesis of TLHE-(Active Agent) Conjugates

We used a modular approach for the assembly of TLHE-(Active agent) conjugates using copper-catalyzed azide-alkyne cycloaddition "Click chemistry".

Figure 9:
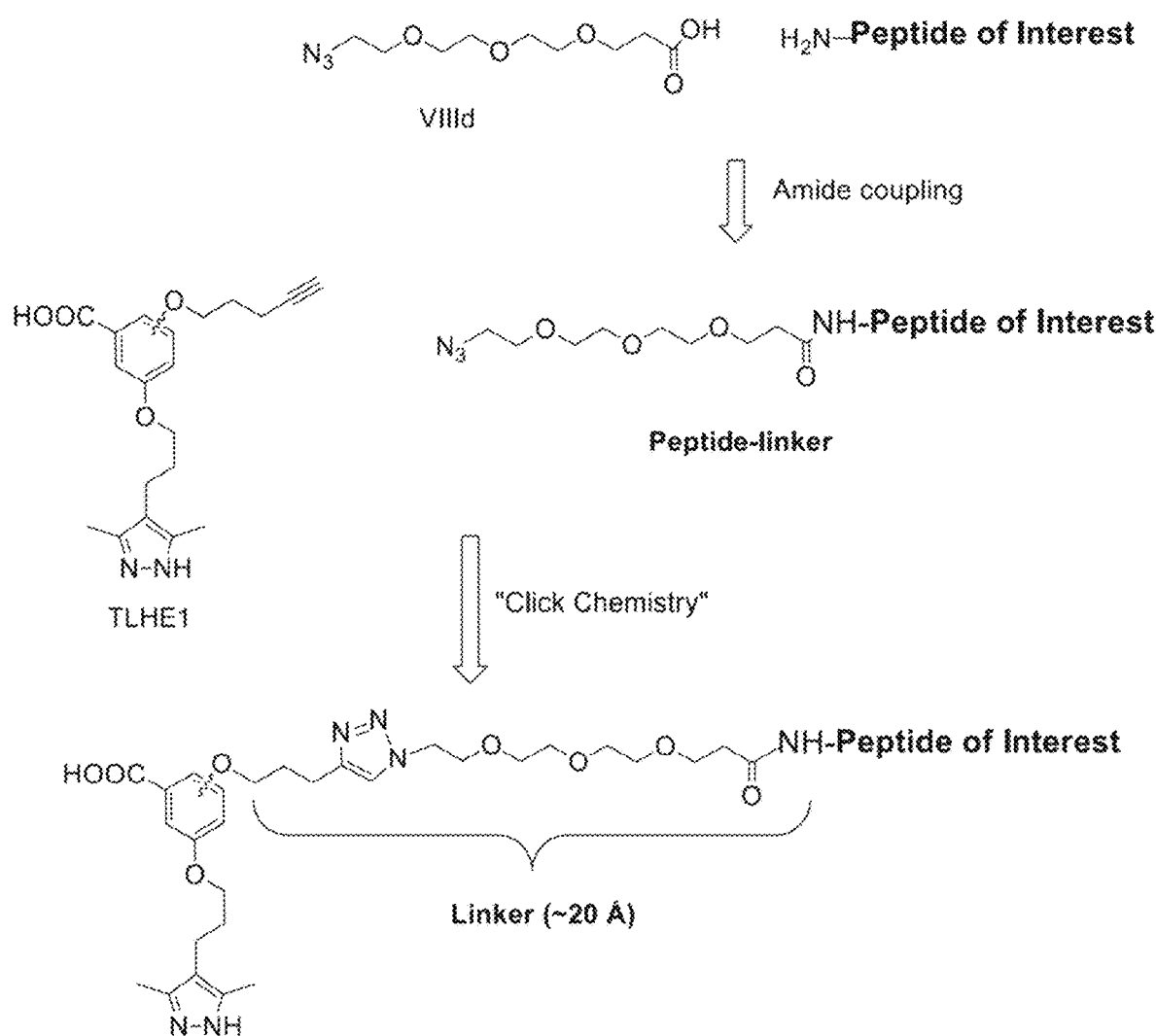
FIG. 9 illustrates a general synthetic scheme to conjugate TLHEs to peptides, according to some embodiments.

FIG. 9 illustrates a general synthetic scheme to conjugate TLHEs to peptides, according to some embodiments. First, a short azide linker VIIId will be attached to the peptide or active agent of interest through an amide bond to give Active agent-linker. This Active agent-linker will be coupled, by click reaction, to TLHE1 to give a linker that is ~20 Å (<350 Da). This assembled linker should be sufficient to clear the linker out of the TTR $T_4$ pocket.

Figure 10A:
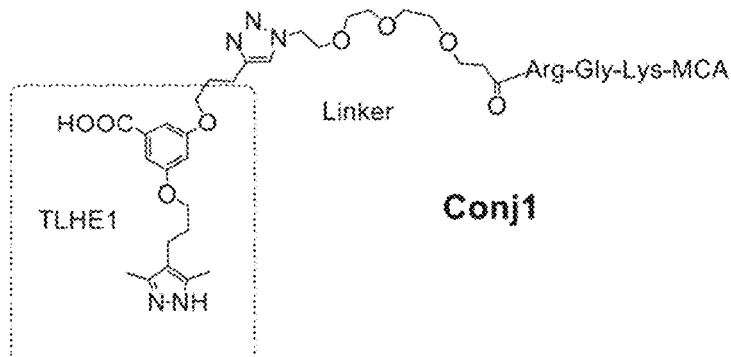
FIGS. 10A-10D illustrate the structure of four TLHE1-peptide conjugates, according to some embodiments.
Figure 10B:
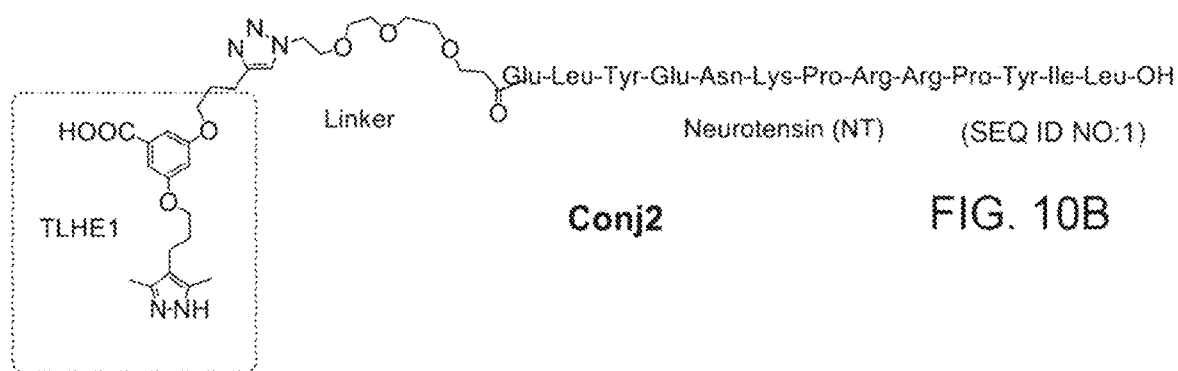
Figure 10C:
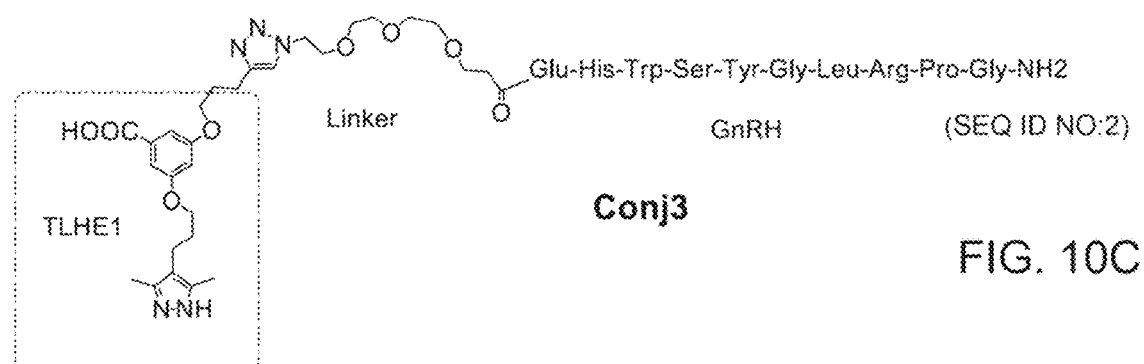
Figure 10D:
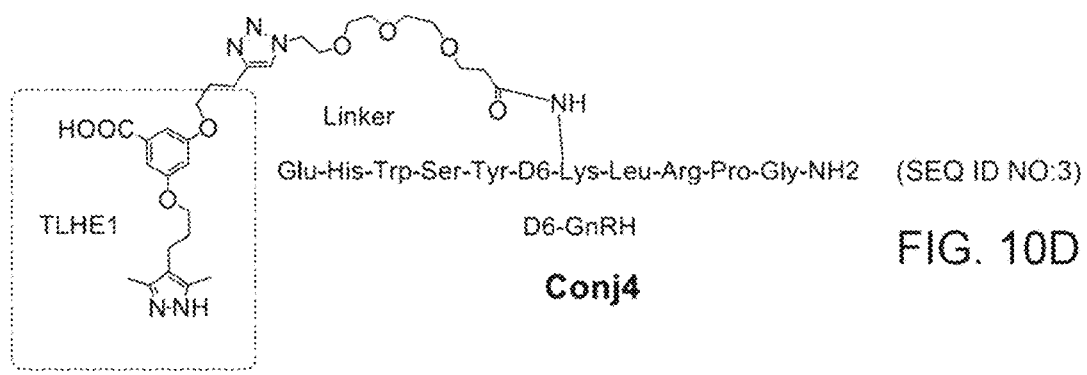
Figure 11A:
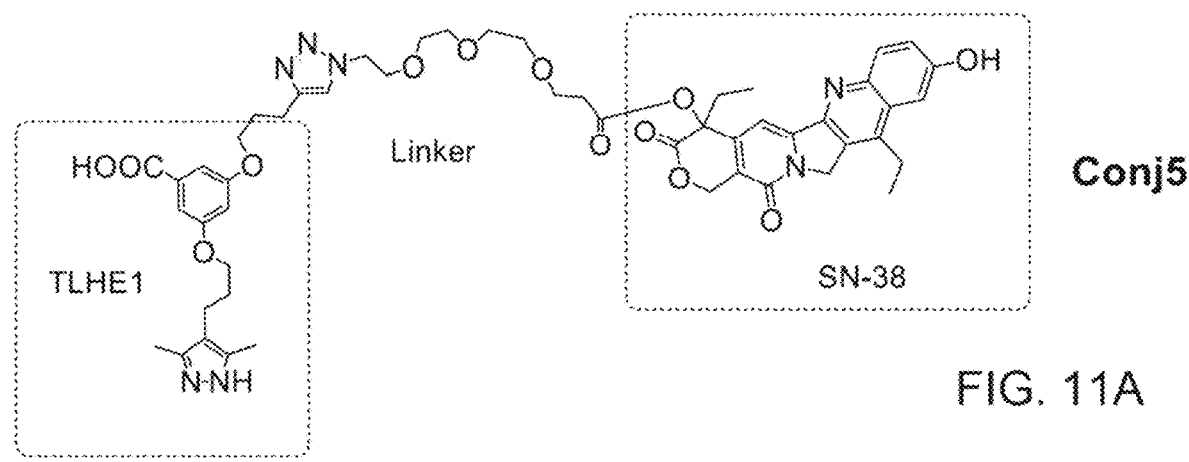
FIGS. 11A-11F illustrate the structure of a TLHE1-small molecule conjugate and five TLHE1-fluorescent dyes conjugates, according to some embodiments.
Figure 11B:
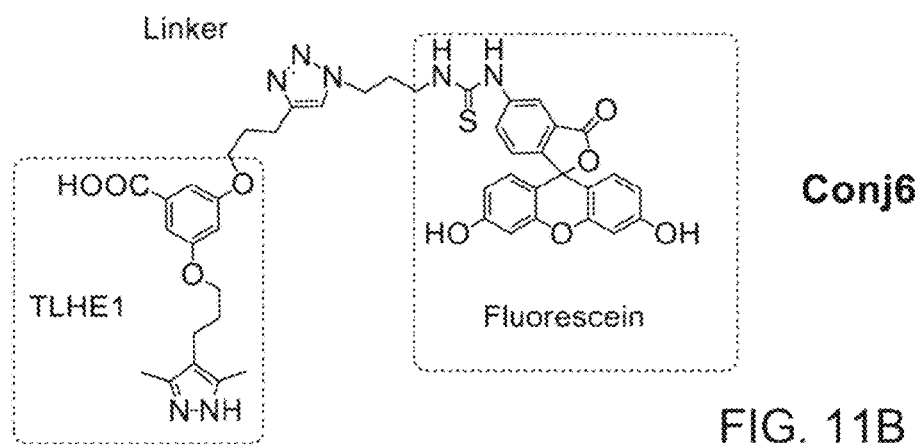
Figure 11C:
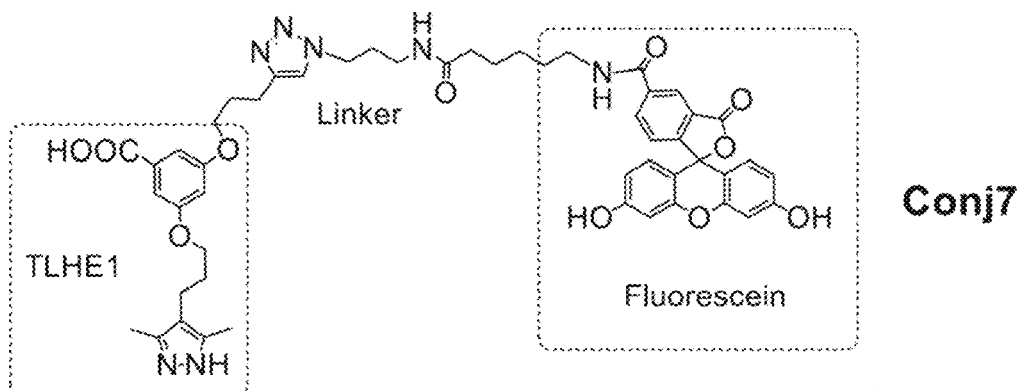
Figure 11D:
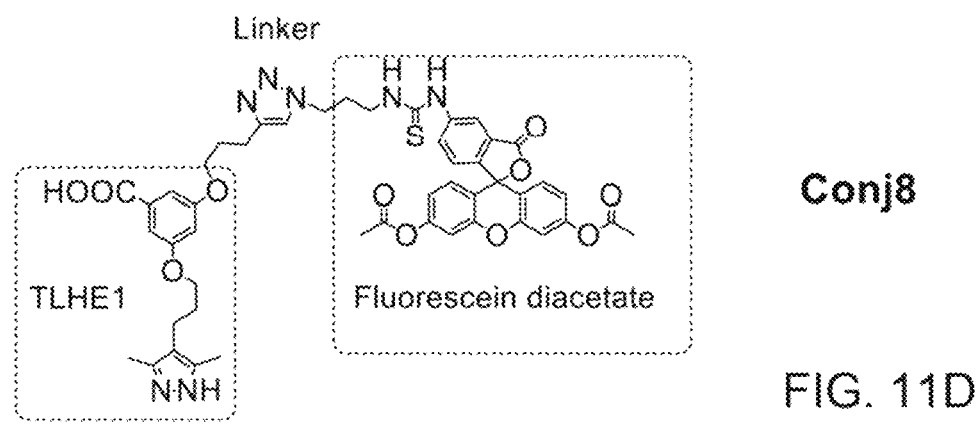
Figure 11E:
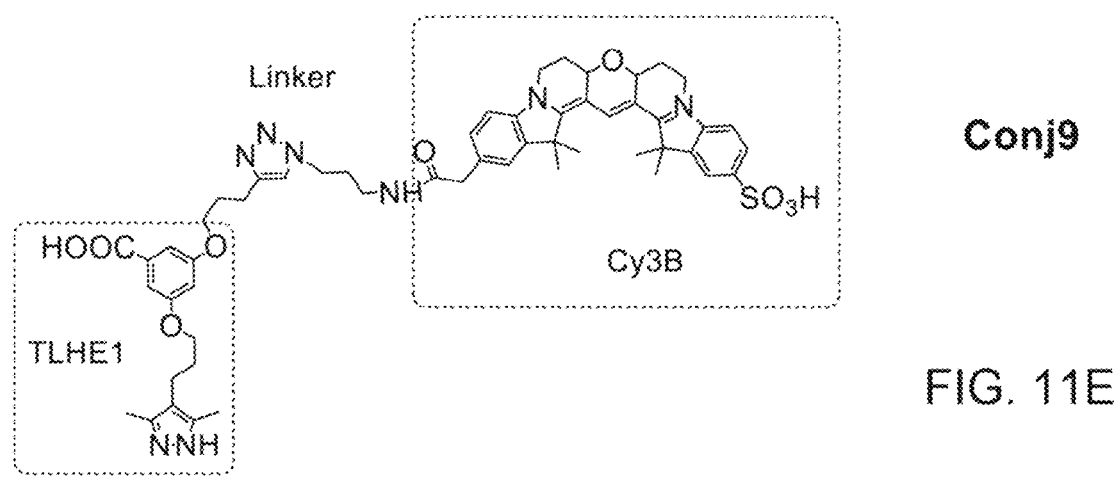
Figure 11F:
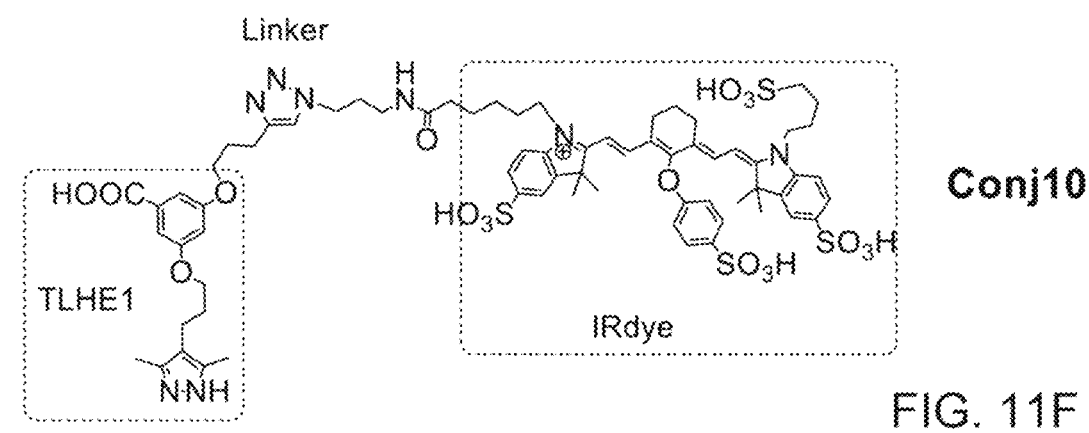

FIGS. 10A-10D illustrate the structure of four TLHE1¬-peptide conjugates, according to some embodiments. We conjugated TLHE1 to four different peptides to give four TLHE1-peptide conjugates: Conj1 to RGK-MCA (FIG. 10A), Conj2 to Neurotensin (NT) (FIG. 10B), Conj3 to GnRH (FIG. 10C), and Conj4 to D6-GnRH (FIG. 10D). All four conjugates displayed good binding affinity to hTTR in buffer ($K_d$ ranging from 200 to 400 nM as determined by SPR) and selectivity for hTTR in human serum (~46 to 57% binding to hTTR in human serum) (FIG. 8).

FIGS. 11A-11F illustrate the structure of a TLHE1¬-small molecule conjugate and five TLHE1¬-fluorescent dyes conjugates, according to some embodiments. We also conjugated TLHE1 to Conj5 to the anticancer agent SN-38, as well as to five fluorescent dyes that could be used for diagnostic purposes: Conj6 to Fluorescein, Conj7 to Fluorescein, Conj8 to Fluorescein diacetate, Conj9 to Cy3B, and Conj10 to IRdye.

Figure 12:
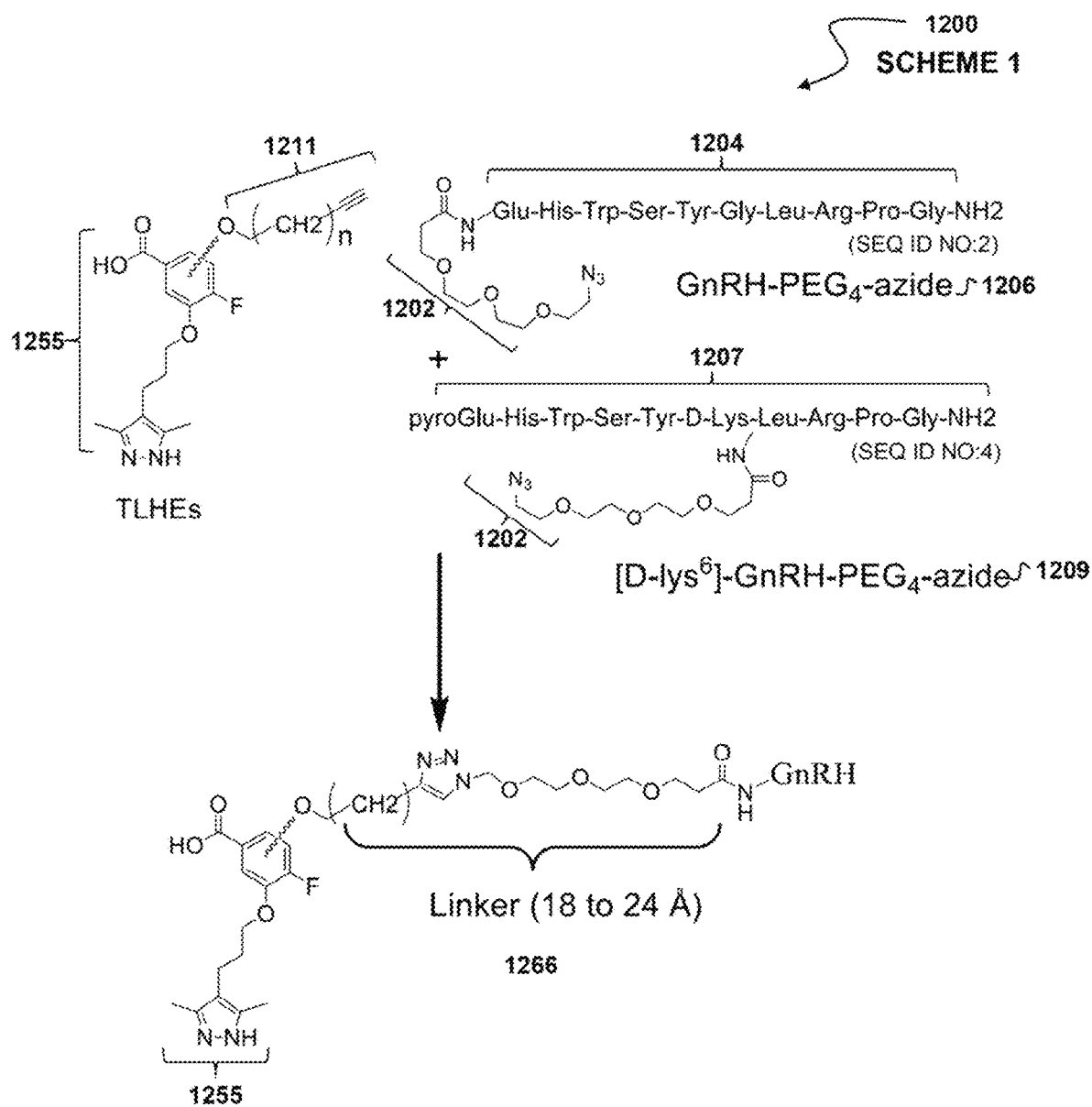
FIG. 12 illustrates "Scheme 1" 1200 as a method of generating a conjugated active agent, a modular approach for assembly of an AG10-GnRH peptide conjugate (Conj3), according to some embodiments.

FIG. 12 illustrates "Scheme 1" 1200 as a method of generating a conjugated active agent, a modular approach for assembly of an AG10-GnRH peptide conjugate (Conj3), according to some embodiments. We used VIIIc 1255 as the TTR ligand. First, a COOH-PEG$_4$-azide linker 1202 was attached to the N-terminus of GnRH 1204 through an amide linkage to give GnRH-PEG$_4$-azide 1206. The same linker 1202 was also attached to the ε-amino of lysine in [D-lys$^6$]-GnRH 507 to give [D-lys$^6$]-GnRH-PEG$_4$-azide 1209. These two GnRH-linker intermediates 1206,1209 were coupled to all the TLHEs we synthesized. The TTR binding pocket is relatively hydrophobic and, therefore, we will use alkyl chains 1211 of various lengths, n=1, 3, 5, 7, and 9 carbon atoms, for example; where, 5 carbons conjugated to PEG$_4$ will result in a linker that is ~20 Å in length. The length of the linker 1266 can be used as an adjustment to clear the linker 1266 out of the $T_4$ pocket of TTR. At the end of these short alkyl chains 1211 there will be a terminal alkyne which will be conjugated to the azide group of the GnRH linkers 1202 using our "click chemistry". These conjugates were synthesized using short alkyl/PEG-linker (<400 daltons), like the linker 566 shown in Scheme 1, which will be attached to the ortho- or meta-positions of VIIIc 1255 and to the N-terminus of GnRH or ε-amine of lysine in [D-lys$^6$]-GnRH as shown in FIG. 12.

Example 6. Chemical Synthesis of TLHE1-Peptide Conjugates (Conj1, Conj2, Conj3, and Conj4)

We have successfully accomplished the synthesis of four TLHE1-peptide conjugates (FIG. 10). Conj1 is TLHE1 conjugated to the fluorogenic tri-peptide Arg-Gly-Lys-MCA. Conj1 stability is evaluated in the in vitro trypsin assay in the presence of hTTR. Conj2 is TLHE1 conjugated to the N-terminus of neurotensin (NT). Conj2 stability is evaluated in the human serum protease assay. Conj3 is TLHE1 conjugated to the N-terminus of native GnRH. Conj3 stability is evaluated in the human serum protease assay and its pharmacokinetic properties are evaluated in vivo in rats. Conj4 is TLHE1 conjugated to the ε-amino group of Lys6 in the GnRH agonist, GnRH-A. Conj4 pharmacokinetic properties and efficacy are evaluated in vivo in rats. Click chemistry was used to directly couple TLHE1 to peptide-PEG4-azide linkers (Scheme 1).

Example 7. Chemical Synthesis of TLHE1-Small Molecule Drug Conjugate (Conj5)

Figure 13:
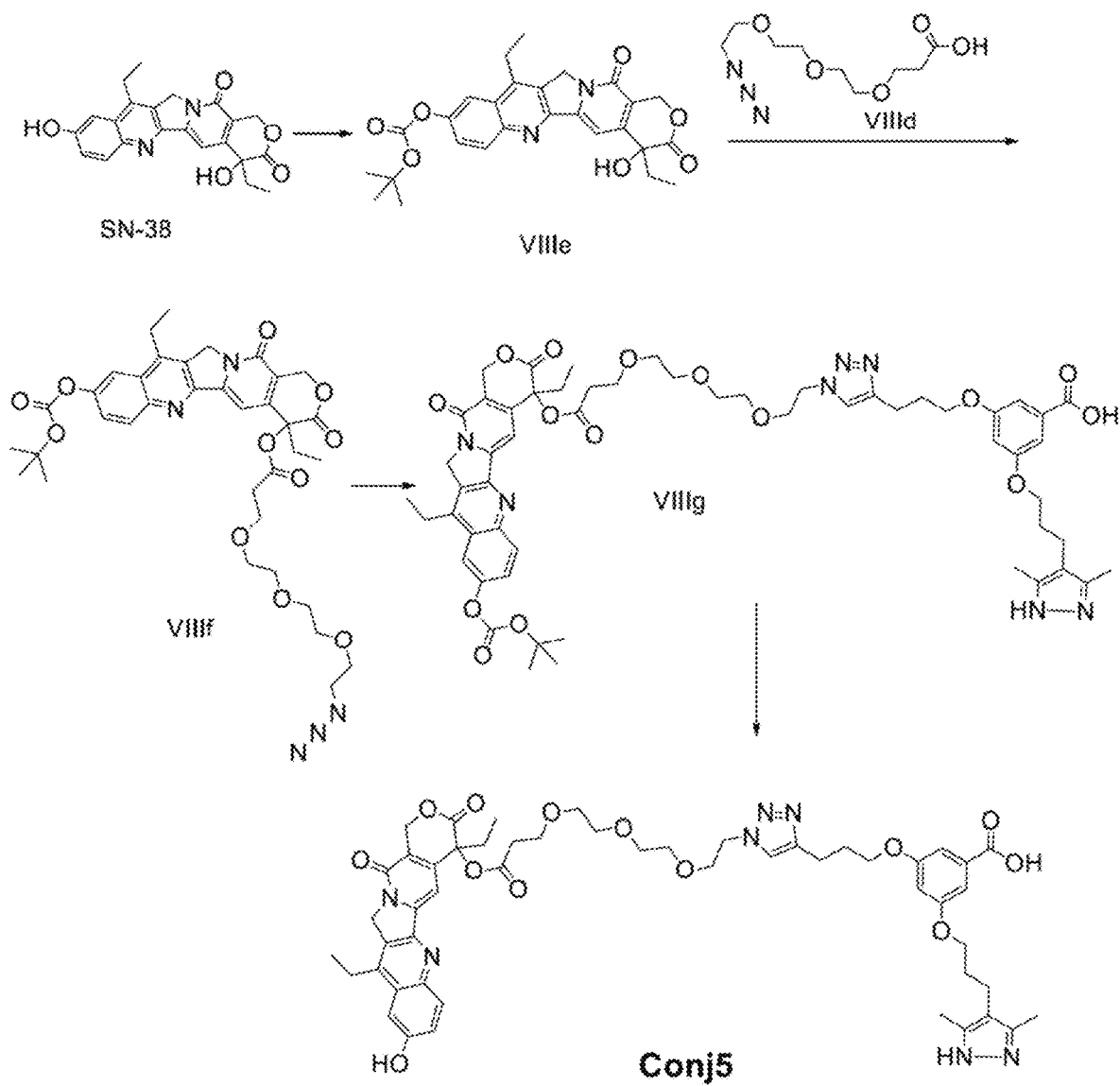
FIG. 13 illustrates synthetic scheme for making for conjugating the anticancer agent SM-38 to TLHE1 (i.e Conj 5), according to some embodiments.

FIG. 13 illustrates synthetic scheme for making for conjugating the anticancer agent SM-38 to TLHE1 (i.e Conj 5), according to some embodiments. As shown in FIG. 13, linker modified SN-38 was coupled to TLHE1.

Example 8. Chemical Synthesis of TLHE1-Imaging Agents Conjugates (Conj6 to Conj10)

The conjugates Conj6, Conj7, Conj8, Conj9, and Conj10 (FIG. 11) were synthesized using Click chemistry. Linker modified Fluoresent dyes were coupled to TLHE1 similar to what is described in Scheme 1 (FIG. 12).

Example 9. Evaluation of the Chemical Stability and Cytotoxicity of TLHE1

TLHE1 is stable in serum and simulated gastric acid for at least 48 h (<3% degradation) and has very low cytotoxicity (% cell viability at 100 μM=96±4%). Therefore, TLHE1 is a very good candidate for conjugation to peptides.

Example 10. hTTR Protects Conj1 Against Proteolysis in Buffer

Figure 14:
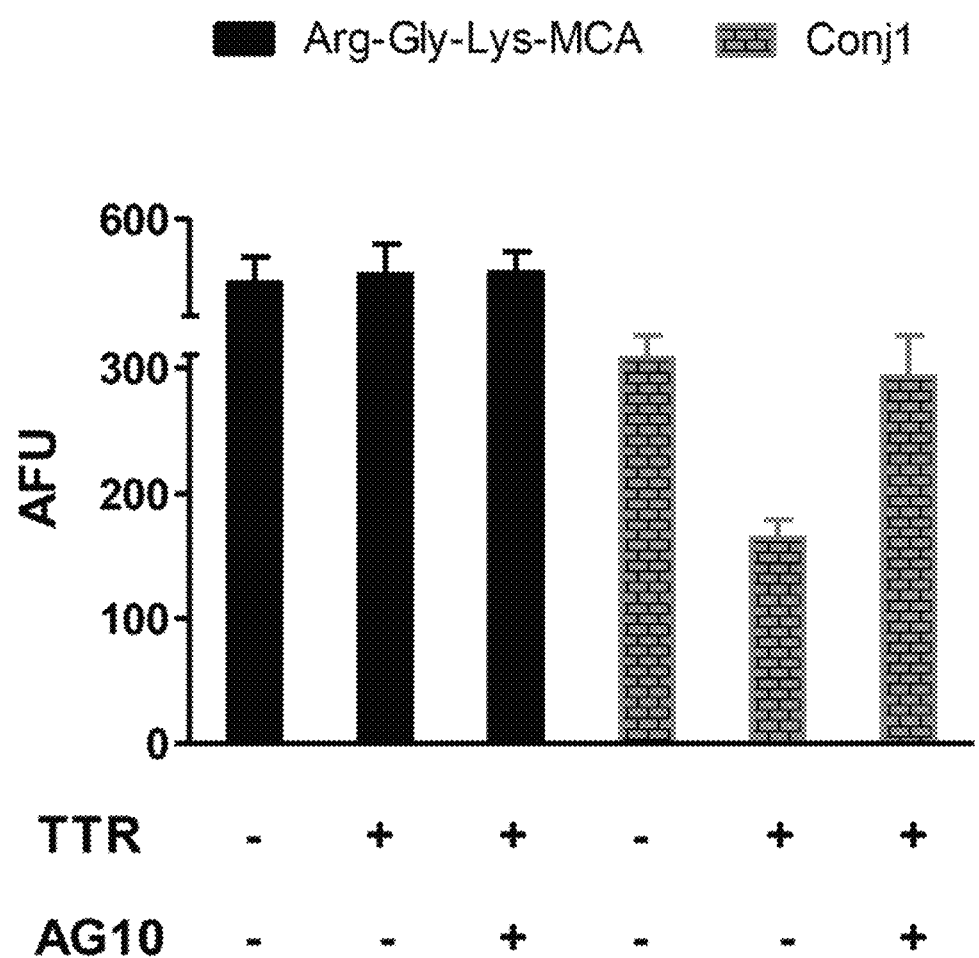
FIG. 14 illustrates the protection effect of binding to TTR on the stability of Conj1 in vitro. hTTR protects Conj1 against trypsin hydrolysis in buffer, according to some embodiments.

We used trypsin to test the ability of hTTR to protect TLHE1-peptide conjugate (Conj1) from proteolysis in buffer. FIG. 14 illustrates the protection effect of binding to TTR on the stability of Conj1 in vitro. hTTR protects Conj1 against trypsin hydrolysis in buffer, according to some embodiments. While there was no protection against proteolysis for Arg-Gly-Lys-MCA in the presence of hTTR, there was significant protection against proteolytic hydrolysis for Conj1 when hTTR is present (Conj1=310±5 AFU; Conj1+hTTR=160±15 AFU). The protective effect of hTTR was eliminated when the reaction mixture was incubated with AG10 (Conj1+hTTR+AG10=290±20 AFU). This shows that the protection effect was mainly due to binding of Conj1 to hTTR.

Proteolysis of Arg-Gly-Lys-MCA and Conj1 (10 μM) by trypsin in buffer in the presence and absence of hTTR (10 μM) or AG10 (20 μM). The mixture was incubated at 37° C. for 30 min and the proteolytic release of 7-amino-4-methylcoumarin (7-AMC) was evaluated by measuring the 7-AMC fluorescence ($\lambda$ex 345 nm and $\lambda$em 440 nm). AFU is arbitrary fluorescence units. Each bar shows the mean (±SD) of four replicates.

Example 11. hTTR Protects Conj2 and Conj3 Against Serum Proteases

To test the ability of hTTR to protect peptides against proteolytic hydrolysis in serum, we used two peptides, neurotensin (NT; 13 amino-acid neuropeptide) and gonadotropin-releasing hormone (GnRH; 10 amino-acid peptide hormone). We conjugated TLHE1, through a short linker (~230 Da), to the N-terminus of NT to give Conj2 and to the N-terminus of GnRH to give Conj3 (FIG. 10). For control, we synthesized Linker modified NT and GnRH (NT-Linker and GnRH-Linker) that does not have TLHE1.

Figure 15A:
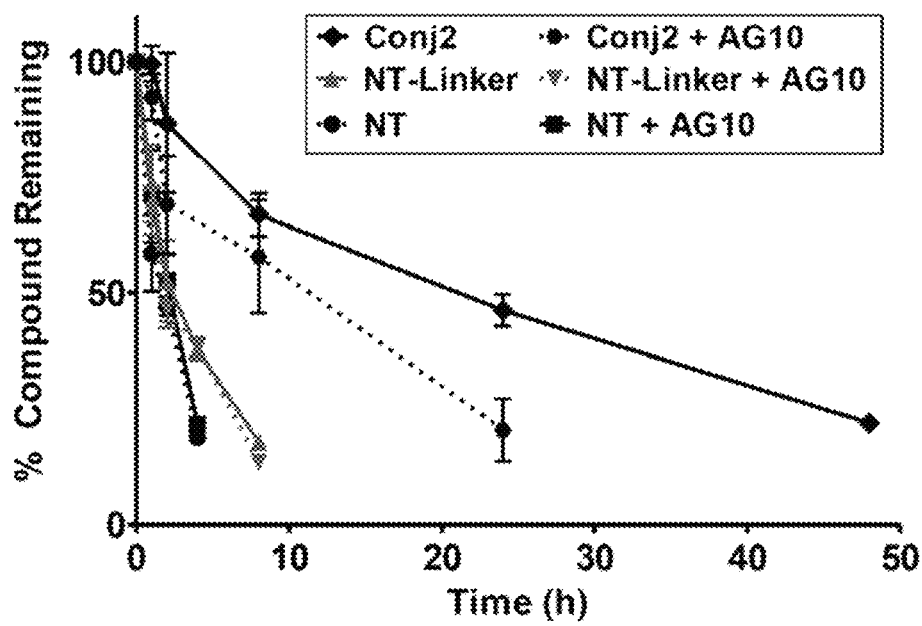
FIGS. 15A and 15B illustrate the protection effect of binding to TTR on the stability of (A) Conj2 and (B) Conj3 against proteolytic hydrolysis in human serum (hTTR conc. ~5 µM), according to some embodiments.
Figure 15B:
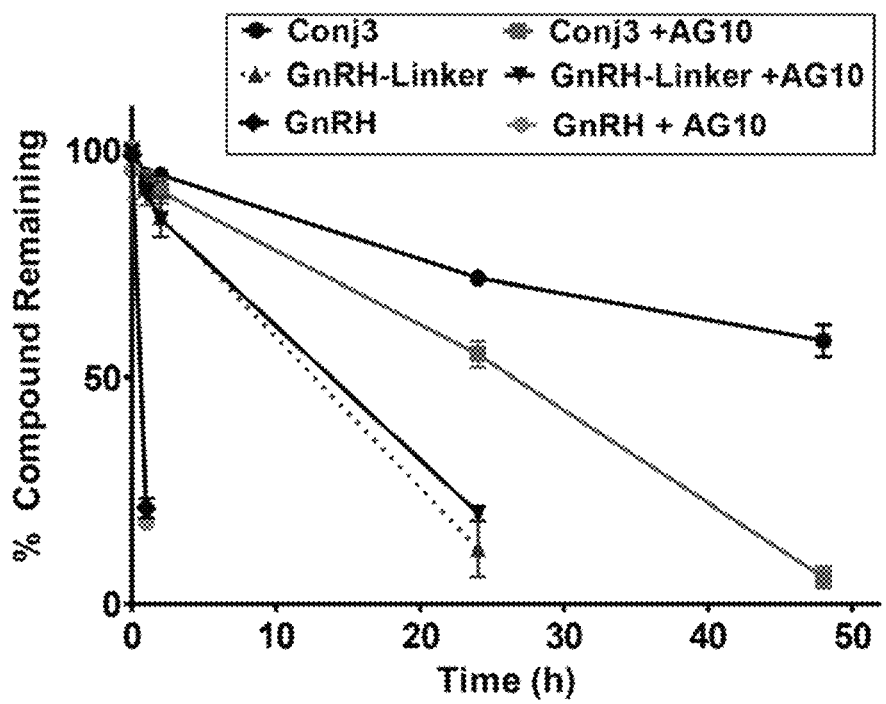

FIGS. 15A and 15B illustrate the effect of binding to TTR on the stability of (A) Conj2 and (B) Conj3 against proteolytic hydrolysis in human serum (hTTR conc. ~5 µM), according to some embodiments. Test compounds (5 µM) were added to serum and to serum pre-incubated with AG10 (10 µM). The amounts of compounds remaining in serum were quantitated at different time-points. Each point shows the mean (±SD) of three replicates.

The stability of Conj2 and Conj3 was evaluated in human serum (hTTR conc. ~5 µM) and in serum samples that are pre-incubated with AG10. NT and GnRH have the lowest stability in serum (no detectable amounts of NT and GnRH after 4 h and 2 h, respectively, FIGS. 15A and 15B). Attaching a short linker to NT (NT-Linker) and GnRH (GnRH-Linker) enhanced their stability (38±2% of NT-Linker remaining at 4 h and 85±4% of GnRH-Linker remaining at 2 h). In comparison, Conj2 (22±1% remaining at 48 h) and Conj3 (58±4% remaining at 48 h) have the most protection against serum proteases. There was no difference in NT-Linker and GnRH-Linker stability between normal serum and serum incubated with AG10. On the other hand, the stability of Conj2 and Conj3 in normal serum was higher than that in serum samples pre-incubated with AG10 (no detectable amount of Conj2 and Conj3 after 24 h and 48 h, respectively). Our data shows that the majority of conjugates protection is the the result of binding to >50% of hTTR (FIG. 8).

Example 12. TTR Extends the Circulation Half-Life of Conj3 in Rats

Figure 16:
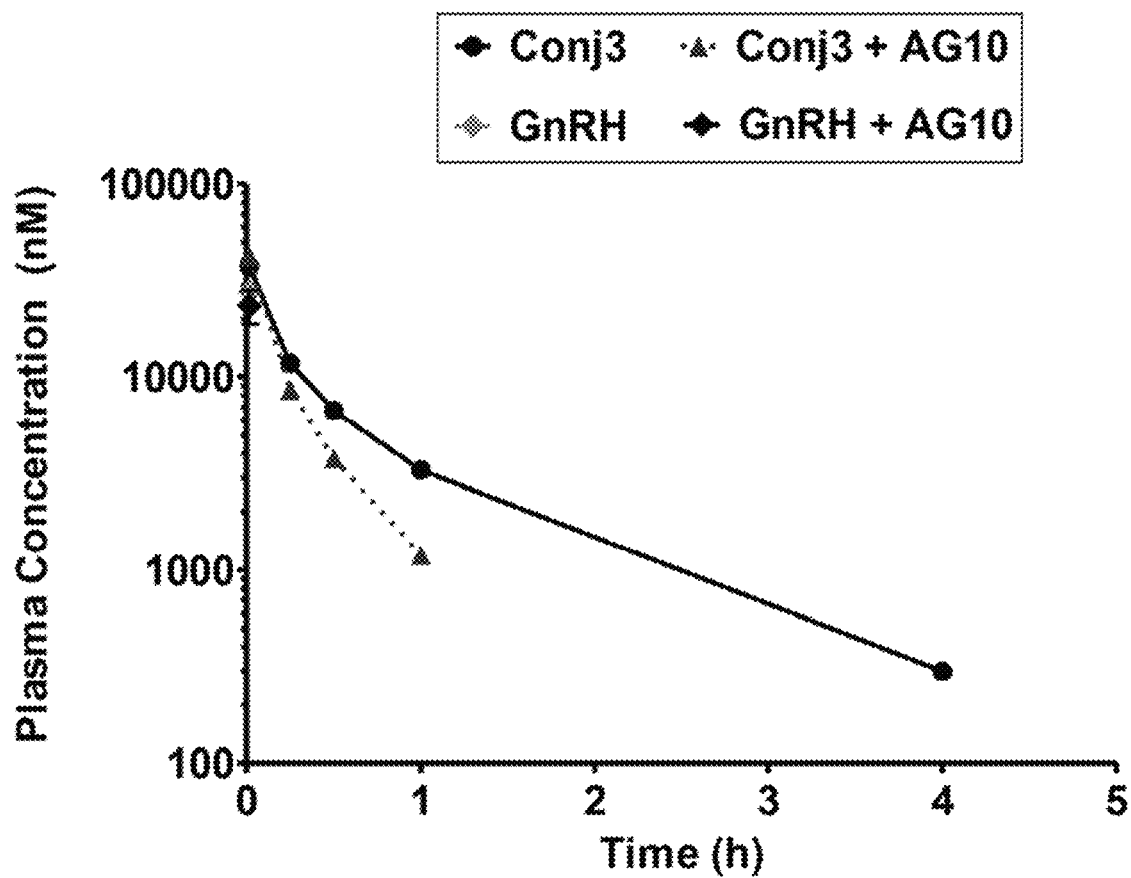
FIG. 16 illustrates the effect of binding to rTTR on extending the half-life of Conj3 in rats, according to some embodiments.

FIG. 16 illustrates the effect of binding to rTTR on extending the half-life of Conj3 in rats, according to some embodiments. Equivalent amounts of GnRH and Conj3 were administered at time 0 (single i.v. bolus; 3.3 µmole/kg of each compound) to two groups of male rats (N=4 for each group); one group was pretreated with vehicle (untreated) while the other group was pretreated with AG10 (AG10-treated group; 17.1 µmole/kg, i.v.). The concentration of test compounds in plasma was determined using validated HPLC method and plotted as a function of time after dosing. Concentrations are expressed as means (±SEM).

Equivalent amounts of GnRH, GnRH-Linker, and Conj3 were administered as a single i.v. bolus to a group of male rats and the plasma concentrations of test compounds were measured at different time points. For control, another set of rats were co-administered with same test compounds (GnRH, GnRH-Linker, and Conj3) but in the presence of AG10. Pharmacokinetic evaluation showed that there was no measurable amount of GnRH at 15 min after administration, which is consistent with the reported short in vivo half-life. The half-life of GnRH-Linker was similar in AG10-treated and untreated rats (half-life=4.2 min & 3.5 min, respectively). In contrast, Conj3 displayed initial rapid distribution phase (half-life=12 min) followed by a longer terminal half-life (46±3 min). The terminal half-life of Conj3 is at least 13-fold longer than that of GnRH or GnRH-Linker. The biphasic profile of Conj3 is similar to what we have observed for AG10 and indicates a TMDD. There was ~3-fold decrease in the half-life of Conj3 in the presence of AG10 (half-life=16±1 min.

Example 13. rTTR Extends the Circulation Half-Life of Conj4 in Rats

Figure 17:
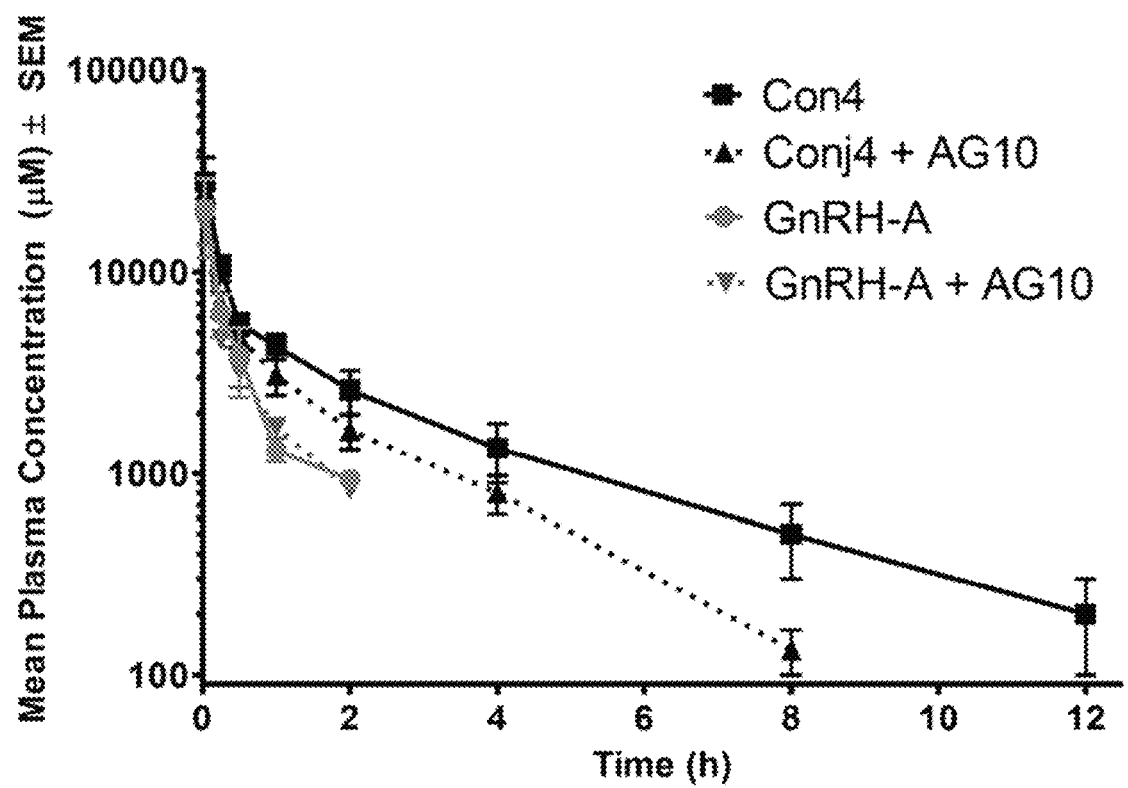
FIG. 17 illustrates that Conj4 displayed extended half-life in rats, according to some embodiments.

FIG. 17 illustrates that Conj4 displayed extended half-life in rats, according to some embodiments. Equivalent amounts of GnRH-A and Conj4 were administered at time 0 (single i.v. bolus; 3.3 µmole/kg of each compound) to two groups of male rats (N=3 for each group); one group was pretreated with vehicle (untreated) while the other group was pretreated with AG10 (AG10-treated group; 17.1 µmole/kg, i.v.). The concentration of test compounds in plasma was determined using validated HPLC method and plotted as a function of time after dosing. Concentrations are expressed as means (±SEM).

We used Conj4 (FIG. 10) to perform the in vivo efficacy and determine if the efficacy correlates with extended in vivo half-life. Conj4 is the product of conjugating TLHE1 to the ε-amino group of Lys6 in the GnRH analog, [D-Lys$^6$]-GnRH (GnRH-A). The pharmacokinetic properties of GnRH-A, GnRH-A-Linker, and Conj4 were evaluated in rats, in the absence and presence of AG10 (FIG. 17). The half-life of GnRH-A was 55±11 min and there was no detectable levels in plasma after 2 h of administration. Similar half-life for GnRH-A was observed in AG10-treated rats (half-life=49±4 min). The PK profile and half-life of GnRH-A-Linker (half-life=58±7 min) was comparable to that of GnRH-A, and there was no detectable levels of GnRH-A-Linker after 2 h in both AG10-treated and untreated rats. In comparison, Conj4 displayed initial rapid distribution phase (half-life=14 min) followed by a much longer terminal half-life (180±12 min) which is >3-fold longer than the half-life of GnRH-A. While there were no detectable plasma levels of GnRH-A after 2 h, Conj4 was present in circulation for at least 12 h (FIG. 19A). The half-life of Conj4 in AG10-treated rats (half-life=102±7 min) was significantly lower than that in AG10-untreated rats. These data strongly support and validate our novel approach that TTR recruitment can indeed enhance the half-life of peptides in vivo.

Example 14. Conj4 Maintains its GnRH-R Efficacy in Rats Over a Prolonged Period

Figure 18:
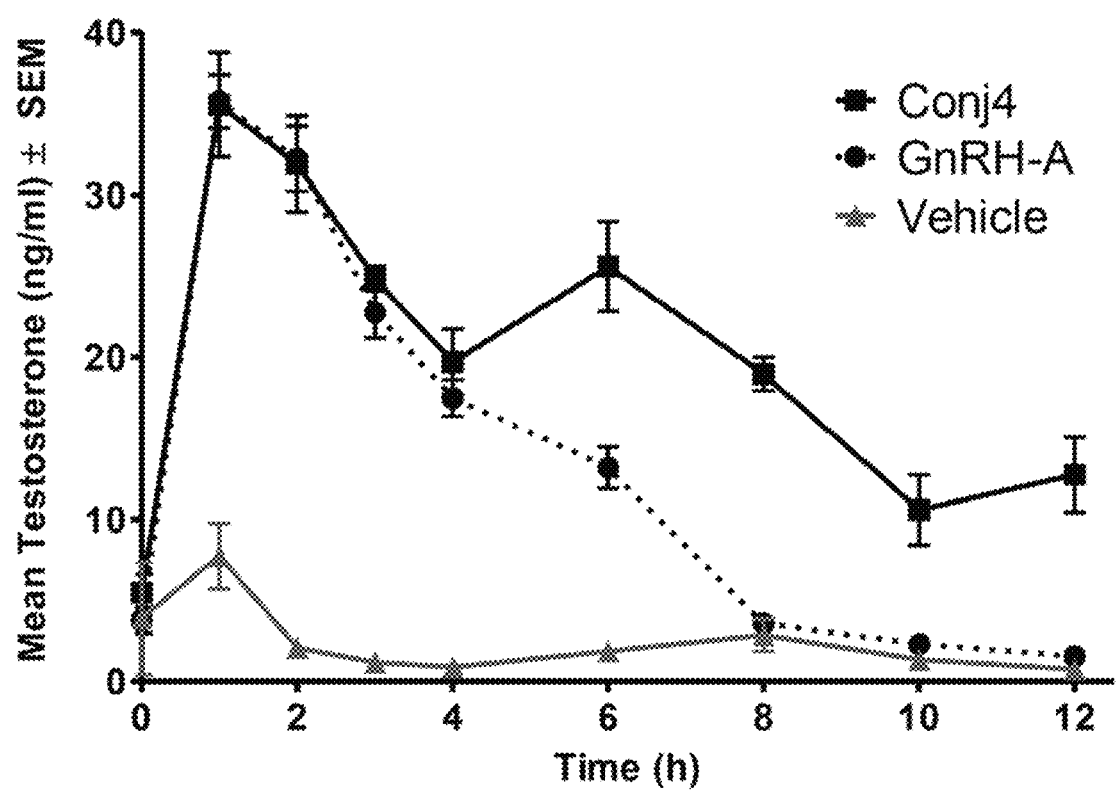
FIG. 18 illustrates that Conj4 displayed extended and superior efficacy in rats by measuring the increase in serm testosterone levels, according to some embodiments.

FIG. 18 illustrates that Conj4 displayed extended and superior efficacy in rats by measuring the increase in serm testosterone levels, according to some embodiments. Administration of Conj4 (single i.v. bolus; 225 ng/kg, 120 picomoles/kg) to gonad-intact male rats (N=4) stimulated the release of testosterone and maintains higher levels of testosterone in circulation compared to administration of equivalent dose of GnRH-A (single i.v. dose; 150 ng/kg, 120 picomoles/kg) to a second group of rats (N=4). For control, a third group (N=3) of rats was administered only vehicle. Testosterone levels in serum were determined using ELISA and concentrations were expressed as means (±SEM).

GnRH agonists interact with GnRH-R in the pituitary gland. Acute dosing of exogenous GnRH agonists is known to cause prompt increase in testosterone levels in male rats. Therefore, the in vivo efficacy of Conj4 on circulating levels of testosterone was evaluated in male rats. Conj4, GnRH-A, or vehicle were administered to three groups of rats, and the serum concentration of testosterone was determined at various time points. In vehicle treated rats, a normal circadian rhythm of testosterone was observed (normal range of serum testosterone in rat is 0.7-5 ng/ml).

Administration of equivalent doses of GnRH-A or Conj4 resulted in significant increase of testosterone levels within 1 h after injection (35.8±1.7 ng/ml and 35.6±3.2 ng/ml, respectively FIG. 18). The comparable efficacy at 1 h for both compounds is consistent with the similar in vitro GnRH-R binding affinity for GnRH-A ($K_d$=1.8 nM) and Conj4 ($K_d$=4.9 nM). While testosterone levels in both treated groups started decreasing after 1 h, the decline in GnRH-A treated rats was significantly faster than that for Conj4 treated rats. At 6 h, there was a significant difference in testosterone levels between GnRH-A (13.2±1.3 ng/ml) and Conj4 (25.6±2.8 ng/ml) treated rats. For GnRH-A, the circulating testosterone levels returned to vehicle treated levels (3.6±0.6 ng/ml) within 8 h after dosing. In contrast, the testosterone levels in Conj4 treated rats at 8 h (18.9±1.0 ng/ml) were significantly higher compared to that of GnRH-A or vehicle treated rats. Importantly, the testosterone level for Conj4 treated rats was still elevated at 12 h post dosing (12.7±2.3 ng/ml) compared to vehicle treated rats (0.8±0.3 ng/ml) (increase of ~16 fold above basal levels). The circulating testosterone levels of Conj4 treated rats returned to the pretreatment range within 24 h. This efficacy data correlates well with our pharmacokinetic data (FIG. 18) and strongly shows that the enhanced efficacy of Conj4 is a result of extended circulating half-life, mainly due to its binding to rTTR.

Example 15. AG10-Bifunctional Conjugates Capable of Forming Irreversible Covalent Adducts with TTR in Serum TTR ligands bearing a carboxylic acid moiety at the appropriate position (such as AG10) bind to TTR and, through the carboxylic acid moiety, form electrostatic interaction with Lysine 15 (K15) in the TTR $T_4$ pocket. See Choi S., et al. Nat Chem Biol. 6:133-9 (2010); and, Penchala S., et al. Proc Natl Acad Sci USA. 11:9992-7 (2013); each of which is incorporated by reference herein in its entirety. It has been shown that some of these small molecules can be converted to irreversible TTR ligand by converting the carboxylic acid into a reactive moiety (X) capable of covalently modifying K15 through an amide bond. When these TTR ligand are administered by oral or parenteral routes, they would bind to TTR and form covalent adduct with TTR in serum. The same principle could be applied to the bifunctional TTR-therapeutic agents by converting the carboxylic acid moiety of the AG10 part of the bifunctional molecule to a reactive group (X) capable of covalently binding to TTR through K15. Upon formation of the bifunctional molecule-TTR conjugate in serum, the bifunctional molecule-TTR conjugate would have similar pharmacokinetic properties to that of the protein carrier, TTR (i.e. maximal in vivo serum half-life of 24 hours and drug concentration of 10 µM). The covalent conjugate would still have some activity since the therapeutic agents (Y) (e.g. peptides, proteins, oligonucleotides, oligosaccharides, virus like particle, imaging agents, and other small molecule drugs) would still be extended, through appropriate linkers, beyond the surface of TTR. However, due to the steric bulk of TTR (56 KDa), it is anticipated that the activity of these covalent conjugates to be less than that of their non-covalent (reversible) counterparts.

The following structure of Compound (IX), is an example of a ligand type that may covalently bond to TTR:

IX wherein, $R^b$ can be any one or any combination of CHO, COOH, COOCH$_3$, COOR$^6$, CONR$^7$R$^8$, tetrazolyl, CONHOH, B(OH)$_2$, CONHSO$_2$Ar, CONHCH(R$^9$)COOH, CF$_3$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

X can be any one or any combination of reactive substituents, such as CHO, CONHOH, B(OH)$_2$, CONHSO$_2$Ar, carboxylic acid ester, carboxylic acid thioester, N-hydroxysuccinimido group, N-hydroxymaleimido group, 2-hydroxypropylene, 1-, 3- or 4-azetidine group, and an a-halomethylcarbonyl (a-haloacetyl) group, where the halo group is preferably bromo or chloro; a Michael acceptor group, such as a substituent that reacts with K15 amine nitrogen in a Michael addition reaction, including a —C(O)CH═CH2 (acryloyl) group, a —S(0)2CH═CH2 (vinylsulfonyl) group, —NHC(O)CH═CH2 (acrylamido) group and —NHS(0)2CH═CH2 (vinylsulfonamido) group;

$X_a$ is C(R$^4$)(R$^5$), O, N—R$^5$ or S; where R$^4$ and R$^5$ are independently selected from hydrogen, alkyl, substituted alkyl, alkenyl, substituted alkenyl, alkynyl, substituted alkynyl, aryl, substituted aryl, alkoxy, aryloxy, hydroxyl, heterocyclic group, halogen, nitro, acyl, substituted acyl, carboxyl, alkoxycarbonyl, substituted alkoxycarbonyl, aminoacyl, substituted aminoacyl, amino, substituted amino, acylamino, substituted acylamino, and cyano;

n is an integer ranging from 0 to 8;

each of R$_1$, R$_2$, and R$_3$ group can be independently selected as any one or any combination of an epoxide, an aziridine or an episulfide group that are present in a glycidyl, aziridinylmethyl or thiiranylmethyl group, as well as a sulfonamide, a vinyl sulfonamide, a sulfonyl fluoride, an alkoxycarbonyl or a substituted alkoxycarbonyl;

Y can be any one or any combination of a peptide, a protein, an oligonucleotide, an oligosaccharide, a virus-like particle, an imaging agents, or a small molecule drug; and, the linker linking can be any moiety that connects two groups and has a backbone of 30 atoms or less in length.

Figure 19:
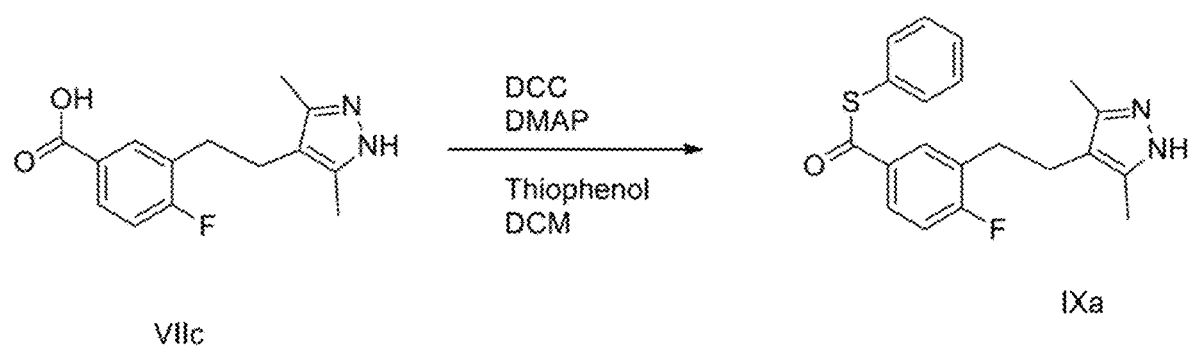
FIG. 19 illustrates the chemical synthesis of an AG10 analogue that can covalently bind to TTR, according to some embodiments.

FIG. 19 illustrates the chemical synthesis of an AG10 analogue (IXa) capable of forming covalent bond with the K15 of TTR, according to some embodiments.

Example 16. Reducing the Immunogenicity of an Active Agent by Binding to TTR

It should be appreciated that repeated dosing of therapeutic peptides of any origin might elicit an immune response. It has been shown that this immunogenicity can also reduce the efficacy of therapeutic agents, including peptides, by lowering the molecule's in vivo half-life due to rapid clearance by immune cells. Several strategies have been proposed to address immunogenicity of therapeutic peptides including PEGylation, humanization, exon shuffling, etc. Another approach is the covalent chemical conjugation of the peptide to a serum protein such as HSA. This increase in the bulk of peptides results in masking of the antigen epitope thereby reduces immune responses. For example, it has been shown that conjugating a HIV fusion inhibitor peptide to HSA increased its serum half-life and also lowered immunogenicity.

Therefore, the (TTR ligand)-(active agent) conjugates taught herein can be administered to lower immunogenicity in subjects by recruiting the bulk of TTR, and this is to be proven by administering a control of the active agent by itself (i.e. without conjugation to the TTR ligand) and comparing the results to the administration of the (TTR ligand)-(active agent) conjugates taught herein.

Example 17. Some Advantages of the Approaches Taught Herein Over Other Approaches Used for Half-Life Extension of Active Agents Besides maintaining potency, the approaches taught herein offer a number of advantages over traditional genetic fusion and PEGylation approaches, for example:

(i) Our approach involves a simple chemical conjugation of peptides to TLHE1, and the products are homogeneous and can be easily characterized and purified (purity>98%) using harsh conditions such as HPLC. The modular nature of the synthesis offers flexibility of attachment sites and incorporation of unnatural amino acids or non-peptidic functionality into the peptide backbone;

(ii) Unlike HSA peptide fusions, where the three-dimensional structure of the fusion partner needs to be maintained, conjugation to TLHE1 results in stable products that do not require refrigeration. This would decrease the cost of production and storage of peptide conjugates;

(iii) Because of the smaller size of our conjugates (<3% the size of HSA conjugates), we anticipate it to penetrate solid tumors efficiently;

(iv) Due to its non-peptidic nature and small size, it is unlikely that TLHE1 can cause immunogenic response; and, (v) The TLHE system would be preferred for certain applications where prolonged exposure to peptides is undesirable.

Example 17. General Experimental

Methods
Materials:
Human hTTR (purified from human plasma) was purchased from Sigma (# P1742). Human serum was purchased from Sigma (# H4522) [hTTR concentration is serum was measured using nephelometric analyzer (28 mg/dL or 5 µM)]. HSA was obtained from Sigma (# A3782; Albumin from human serum, >99%). Thyroxine ($T_4$) was purchased from Fisher Scientific. HPLC analysis of PK studies rat plasma was performed on an Agilent 1100 series HPLC system connected to a diode array detector operating between the UV ranges of 200-400 nm and quantified using Agilent Chemstation software. The mobile phase was composed of solvent A consisting methanol-water (5:95, v/v) containing 0.1% trifluoroacetic acid and solvent B consisting methanol-water (95:5, v/v) containing 0.1% trifluoroacetic acid. Protected amino acids and peptide coupling reagents were purchased from Chem-Impex International. The 2-chlorotrityl resin was purchased from Advanced Chem Tech (# SC5055, 1.6 mmol/g) and Rink amide MBHA resin was purchased from Novobiochem (#855003, 0.79 mmol/g).

Animal:
Adult jugular vein cannulated male Sprague-Dawley (SD) rats purchased from Charles River Laboratories (Hollister, Calif.). All animals were maintained in a temperature-controlled room (22.2° C.) with a photoperiod of 12-h light/12-h dark (lights on at 6:00 AM). Rat chow (Lab Diet™ #5001) and tap water were provided ad libitum. Animal supplies including catheter maintenance solutions were purchased from SAI infusion technologies. Sterile IV fluids were obtained from Patterson Veterinary. All animal protocols were approved by the Animal Care Committee of the University of the Pacific and complied with the Guide for the Care and Use of Laboratory Animals (Eighth Edition, 2011).

Metabolism Study of AG10 in Human Liver Microsomes (HLM):
Microsomal incubations were conducted for AG10 in the absence and presence of hTTR or human serum albumin (HSA). Incubation mixtures consisted of human liver microsomes (1 mg/mL), AG10 (5 µM), hTTR or HSA (5 µM), $MgCl_2$ (4 mM), and NADPH (1.6 mM) in a total volume of 500 µL potassium phosphate buffer (100 mM, pH 7.4). Incubation mixtures were preincubated at 37° C. for approximately 10-15 minutes then reaction was started by addition of NADPH (or buffer for negative control). At 0 h and 2 h, 80 µL aliquots were taken and added to equal volume of methanol. Samples were centrifuged at 16,000×g for 10 minutes and supernatants were stored at −20° C. until analysis by HPLC.

Dose Escalation of AG10 in Rats:
Adult male Wistar rats, body weight ranging 160-200 g, were used for the study. Escalating single i.v. doses of 5, 20, and 50 mg/kg of AG10 (sodium salt solution in water) were administered to three groups of rats (3 rats per group). Blood samples were collected at 0.08, 2, 4, 8, and 24 hour time intervals. The plasma samples were prepared by centrifugation at 15,000 RPM for 5 min. The resultant plasma was precipitated using 2× solvent B (95:5, Methanol-Water, 0.1% TFA). Samples were centrifuged at 15,000 RPM for 5 minutes and supernatants were stored at −20° C. until analysis by HPLC.

Stability of Conj2, and Conj3 in Serum:
The stability of Conj2 and Conj3 (5 µM) in serum was performed in the presence and absence of AG10 (10 µM). Conj2 and Con3 were incubated in 0.5 mL of human serum at 37° C. and samples (50 µL) were assayed at 0, 2, 4, 8 and 24 h time intervals. Samples were processed by adding 200 µL of Solvent B (95% Methanol and 0.1% TFA in Water) followed by centrifuging at 16,000×g for 5 min and analyzing the supernatant using the previously described validated HPLC method.

Trypsin Cleavage Experiment for Conj1:
In 96-well clear bottom plate, a solution of test compound (10 µM of Arg-Gly-Lys-MCA or Conj1) (with or without 20 µM AG10) in PBS (87.5 µL) was incubated with Trypsin (TrypLE™ Express, Gibco®, 12.5 µL, 1×) in the presence and absence of hTTR (10 µM). The mixture was incubated at 37° C. for 30 min. The release of 7-amino-4-methylcoumarin (7-AMC) was evaluated by measuring the fluorescence ($\lambda_{ex}$345 nm and $\lambda_{em}$=440 nm) using a microplate spectrophotometer reader (Molecular Devices SpectraMax M5). The fluorescence signals of 7-AMC were measured against a blank with buffer and substrates but without Trypsin. The experiment was performed in quadruplicate.

Evaluation of the Pharmacokinetic Profile of Conj3 and Conj4 in Rats:
Jugular vein cannulated Sprague-Dawley male rats (200-220 g, 49-52 days old) were used for this study. An extension catheter was attached to the indwelling jugular vein cannula to facilitate remote sampling. The animals were randomly divided into two groups (N=3 or 4): control group and treatment group. The treatment group was pretreated intravenously with AG10 (5.0 mg/kg body weight; 17.1 µmole/kg; in 200 µL sterile water) followed by a single combined intravenous dose of molar equivalent (as a single i.v. dose; 3.3 µmole/kg of each compound) of all test compounds: For Conj3 study [GnRH (3.87 mg/kg), GnRH-linker (4.68 mg/kg), Conj3 (8.83 mg/kg)] and for Conj4 study [GnRH-A (4.1 mg/kg), GnRH-A-linker (4.85 mg/kg), Conj4 (6.0 mg/kg)] (in 38% PEG-400, 5% DMSO in saline). Simultaneously, the control group was pretreated with vehicle (sterile water) followed by a single combined intravenous dose of molar equivalent of all test compounds as described above. Plasma was collected from each rat and precipitated using 2× solvent B (95:5, Methanol-Water, 0.1% TFA). Samples were centrifuged at 15,000 RPM for 5 minutes and Evaluation of the Efficacy of Conj4 in Rats:

Jugular vein cannulated Sprague-Dawley male rats (300-325 g, 68-73 days old) were used for this study. Group one (N=4) was a control group treated only vehicle (200 μL of 30% PEG in saline; i.v.); Group two (N=4) was treated with GnRH-A (150 ng/kg, 120 picomoles/kg); Group three (N=4) was treated with equivalent dose of Conj4 (225 ng/kg, 120 picomoles/kg; i.v.). The GnRH-A and Conj4 samples were also prepared in the same vehicle as the control (i.e. 200 μL of 30% PEG-400 in saline). Serum samples were collected, for each rat and stored in a −20° C. until assayed for testosterone. Serum testosterone levels were measured using an established rat ELISA assay (ALPCO Diagnostics, New Hampshire, cat #55-TESMS-E01). The testosterone ELISA assay is a competitive immunoassay for the quantitative measurement of testosterone in rat serum. The assay was performed according to the kit manufacturer's protocol. Known concentrations of testosterone were used to generate a standard curve. The sensitivity of the kit was 0.066 ng/ml. Testosterone levels were expressed as means (±SEM). Significant differences between groups of animals were determined by one way analysis of variance with post hoc Dunnett's multiple comparisons test at each particular time point (GraphPad Prism).

Chemical Synthesis 3-(3-(3,5-dimethyl-1H-pyrazol-4-yl)propoxy)benzoic Acid (VIIIc)

VIIIc was synthesized starting with 3-hydroxybenzoic acid using a similar approach as described for VIIc. VIIIc is a white solid; $^1$H NMR (CD$_3$OD, 600 MHz) δ 7.58-7.56 (m, 1H), 7.50-7.49 (m, 1H), 7.34-7.49 (t, 1H, J=7.8 Hz), 7.13-7.10 (m, 1H), 3.93 (t, 2H, J=6.0 Hz), 2.58 (t, 2H, J=7.2 Hz), 2.12 (s, 6H), 1.95-1.90 (m, 2H); HRMS m/z: calcd for C$_{15}$H$_{18}$N$_2$O$_3$+H$^+$ 275.1396; found 275.1390 (M+H$^+$).

SCHEME 2. Synthesis of TLHE1. a) K$_2$CO$_3$, KI, MeCN, reflux, 24 h; b) 1,3-dibromopropane, K$_2$CO$_3$, DMF, rt, 16 h; c) i. acetylacetone, DBU, benzene, rt 3 days; ii. hydrazine hydrate, ethanol, 90° C., 4 h; d) LiOH, THF, water, rt, 14 h.

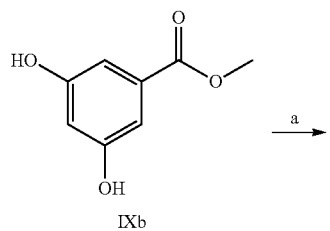

IXb

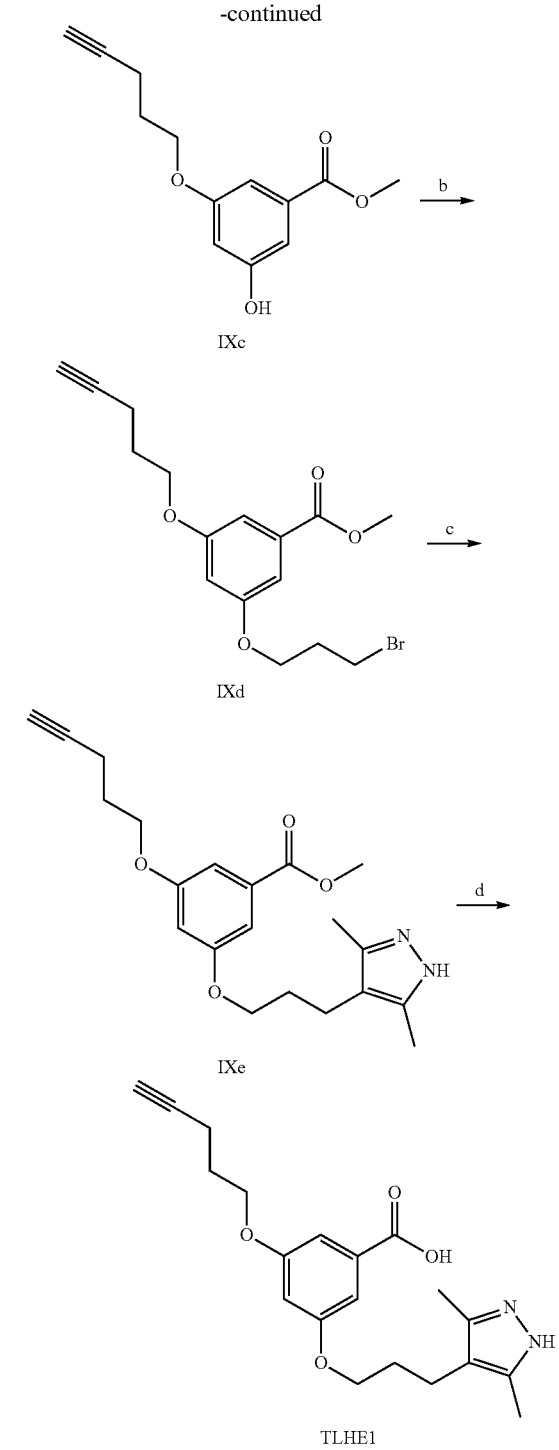

Methyl 3-hydroxy-5-(pent-4-yn-1-yloxy)benzoate (IXc)

To a solution of methyl 3,5-dihydroxybenzoate IXb (0.77 g, 4.58 mmol, 1 equiv) and 4-Pentynyl p-Tosylate (0.98 g, 4.12 mmol, 0.9 equiv) in anhydrous MeCN (30 ml) was added K$_2$CO$_3$ (1.267 g, 9.16 mmol, 2 equiv) and KI (0.153 g, 0.92 mmol, 0.2 equiv). The suspension was heated to reflux for 16 h, filtered, and the solid was rinsed with MeCN. The filtrate was concentrated under reduced pressure. Water was added to the residue and the aqueous phase was extracted with EtOAc, washed brine and dried with $Na_2SO_4$. Concentration and purification flash chromatography (silica gel, 1-10% EtOAc/hexanes) gave compound IXc (0.684 g, 71% yield); $^1$H NMR (CDCl$_3$, 600 MHz) δ 7.16-7.14 (m, 2H), 6.62 (t, 1H, J=2.4 Hz), 4.08 (t, 2H, J=6.0 Hz), 3.89 (s, 3H), 2.42-2.38 (m, 2H), 2.02-1.96 (m, 3H); (ESI$^+$) m/z: calcd for $C_{13}H_{14}O_4$+H$^+$ 235.0970; found 235.0961 (M+H$^+$).

Methyl 3-hydroxy-5-(pent-4-yn-1-yloxy)benzoate (IXd)

To a solution of IXc (360 mg, 1.54 mmol, 1 equiv) and 1,3-dibromopropane (0.78 ml, 7.7 mmol, 5 equiv) in DMF (5 ml) was added $K_2CO_3$ (256 mg, 1.85 mmol, 1.2 equiv). The reaction mixture was stirred at room temperature for 16 hours. The mixture was diluted with EtOAc (150 ml), washed with brine (3×50 ml) and dried with $Na_2SO_4$. Concentration and purification by flash column chromatography (silica gel, 1-10% EtOAc/hexanes) gave compound IXd (468 mg, 86% yield); $^1$H NMR (CDCl$_3$, 600 MHz) δ 7.19-7.17 (m, 2H), 6.64 (t, 1H, J=2.4 Hz), 4.12 (t, 2H, J=5.8 Hz), 4.08 (t, 2H, J=6.0 Hz), 3.89 (s, 3H), 3.59 (t, 2H, J=6.4 Hz), 2.42-2.38 (m, 2H), 2.33-2.29 (m, 2H), 2.02-1.96 (m, 3H); (ESI$^+$) m/z: calcd for $C_{16}H_{19}BrO_4$+H$^+$ 355.0545; found 355.0529 (M+H$^+$).

Methyl 3-(3-(3,5-dimethyl-1H-pyrazol-4-yl) propoxy)-5-(pent-4-yn-1-yloxy)benzoate (IXe)

A solution of IXc (450 mg, 1.27 mmol, 1 equiv) in benzene (3 ml) was added dropwise to a solution of acetyl acetone (0.26 ml, 2.54 mmol, 2 equiv) and DBU (0.38 ml, 2.54 mmol, 2 equiv) in benzene (7 ml). The reaction mixture was stirred at room temperature for 3 days. The mixture was filtered and passed through a pad of silica gel. The solvent were removed and the residue was dissolved in in ethanol (5 ml). Hydrazine hydrate (0.17 ml, 3.18 mmol, 2.5 equiv) was added and the reaction was heated under reflux for 4 hours. Concentration and purification by flash column chromatography (silica gel, 1-20% MeOH/CH$_2$Cl$_2$) gave compound IXe (150 mg, 32% yield) in two steps; $^1$H NMR (CD$_3$OD, 600 MHz) δ 7.13-7.08 (m, 2H), 6.67 (t, 1H, J=2.34 Hz), 4.07 (t, 2H, J=6.0 Hz), 3.90 (t, 2H, J=6.0 Hz), 3.86 (s, 3H), 2.56 (t, 2H, J=7.2 Hz), 2.38-2.34 (m, 2H), 2.23 (t, 1H, J=2.6 Hz), 2.11 (s, 6H), 1.97-1.88 (m, 4H); HRMS (DART) m/z: calcd for $C_{21}H_{26}N_2O_4$+H$^+$ 371.1971; found 371.1968 (M+H$^+$).

3-(3-(3,5-dimethyl-1H-pyrazol-4-yl)propoxy)-5-(pent-4-yn-1-yloxy)benzoic Acid (TLHE1)

To a suspension of IXe (85 mg, 0.23 mmol, 1 equiv) in a mixture of THF (3 ml) and water (3 ml) was added LiOH.H$_2$O (19 mg, 0.46 mmol, 2 equiv). The reaction mixture was stirred at room temperature for 14 hr after which it was cooled to 00° C. and carefully acidified to pH 2-3 with 1N aqueous HCl. The mixture was extracted with EtOAc (3×20 ml) and the combined organic extracts were dried over anhydrous sodium sulfate. Concentration and purification by flash column chromatography (silica gel, 10-50% MeOH/CH$_2$Cl$_2$) gave TLHE1 (59 mg, 73% yield) as a white solid; $^1$H NMR (CD$_3$OD, 600 MHz) δ 7.14-7.10 (m, 2H), 6.66 (t, 1H, J=2.4 Hz), 4.07 (t, 2H, J=6.0 Hz), 3.90 (t, 2H, J=6.0 Hz), 2.57 (t, 2H, J=7.2 Hz), 2.38-2.35 (m, 2H), 2.24 (t, 1H, J=2.4 Hz), 2.12 (s, 6H), 1.97-1.88 (m, 4H); HRMS (DART) m/z: calcd for $C_{20}H_{24}N_2O_4$+H$^+$ 357.1814; found 357.1818 (M+H$^+$).

SCHEME 3. Synthesis of TLHE2. a) $K_2CO_3$, KI, MeCN, reflux, 24 h; b) 6N HCl/THF, 50° C., 2 h; c) 1,3-dibromopropane, $K_2CO_3$, DMF, rt, 16 h; d) i. acetylacetone, DBU, benzene, rt, 3 days; ii. hydrazine hydrate, ethanol, 90° C., 4 h; d) LiOH, THF, water, rt, 14 h.

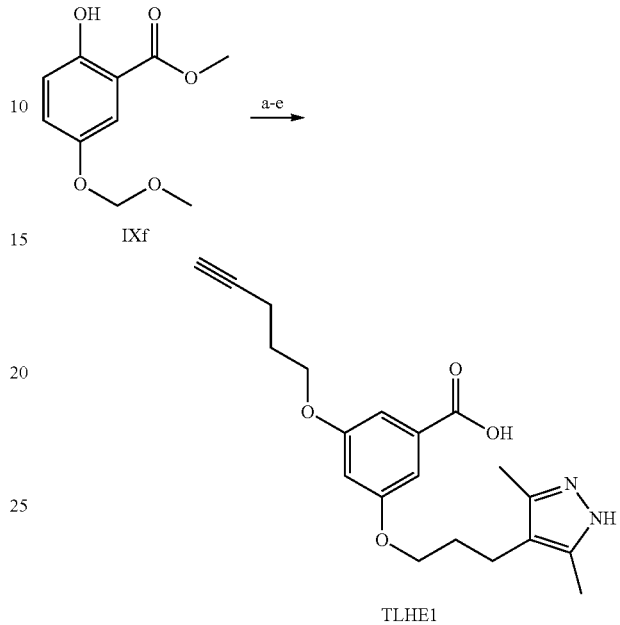

5-(3-(3,5-dimethyl-1H-pyrazol-4-yl)propoxy)-2-(pent-4-yn-1-yloxy)benzoic Acid (TLHE2)

TLHE2 was synthesized starting with IXf {using a similar approach as described for TLHE1 above. TLHE2 is a white solid; $^1$H NMR (CD$_3$OD, 600 MHz) δ 7.29-7.28 (m, 1H), 7.04-7.02 (m, 2H), 4.10 (t, 2H, J=6.0 Hz), 3.85 (t, 2H, J=6.0 Hz), 2.55 (t, 2H, J=7.2 Hz), 2.40-2.37 (m, 2H), 2.21 (t, 1H, J=2.7 Hz), 2.11 (s, 6H), 1.98-1.93 (m, 2H), 1.90-1.84 (m, 2H); HRMS (DART) m/z: calcd for $C_{20}H_{24}N_2O_4$+H$^+$ 357.1814; found 357.1817 (M+H$^+$).

Synthesis of TLHE3: 3-(3-(1-(2-(2-(2-(2-carboxyethoxy)ethoxy)ethoxy)ethyl)-1H-1,2,3-triazol-4-yl) propoxy)-5-(3-(3,5-dimethyl-1H-pyrazol-4-yl) propoxy)benzoic Acid (TLHE3)

The click (CuAAC) reaction was carried out by reacting TLHE1 (49 mg, 0.138 mmol) with azide linker 3-(2-(2-(2-azidoethoxy)ethoxy)ethoxy)propanoic acid (VIIId, 68 mg, 0.276 mmol) with, CuSO$_4$ (22 mg, 0.138 mmol), and sodium ascorbate (54 mg, 0.276 mmol) in a mixture of H$_2$O/THF (2:1) (5 ml). The reaction mixture was stirred at room temperature for 24 h. The crude product was purified by preparative HPLC to give of TLHE3 (53 mg, 64% yield); $^1$H NMR (CD$_3$OD, 600 MHz) δ 7.81 (1H, s), 7.10 (2H, d, J=2.4 Hz), 6.66 (1H, t, J=2.4 Hz), 4.51 (2H, t, J=4.8 Hz), 4.01 (2H, t, J=6.0 Hz), 3.90 (2H, t, J=6.0 Hz), 3.84 (2H, t, J=4.8 Hz), 3.68 (2H, t, J=6.6 Hz), 3.55-3.52 (8H, m), 2.88 (2H, t, J=7.8 Hz), 2.56 (2H, t, J=7.2 Hz), 2.49 (2H, t, J=6.6 Hz), 2.15-2.10 (m, 8H), 1.93-1.88 (2H, m); HRMS (DART) m/z: calcd for $C_{29}H_{41}N_5O_9$+H$^+$ 604.2982; found 604.2969 (M+H$^+$).

SCHEME 4. Synthesis of fluorogenic peptides Arg-Gly-Lys-MCA and Conj1.
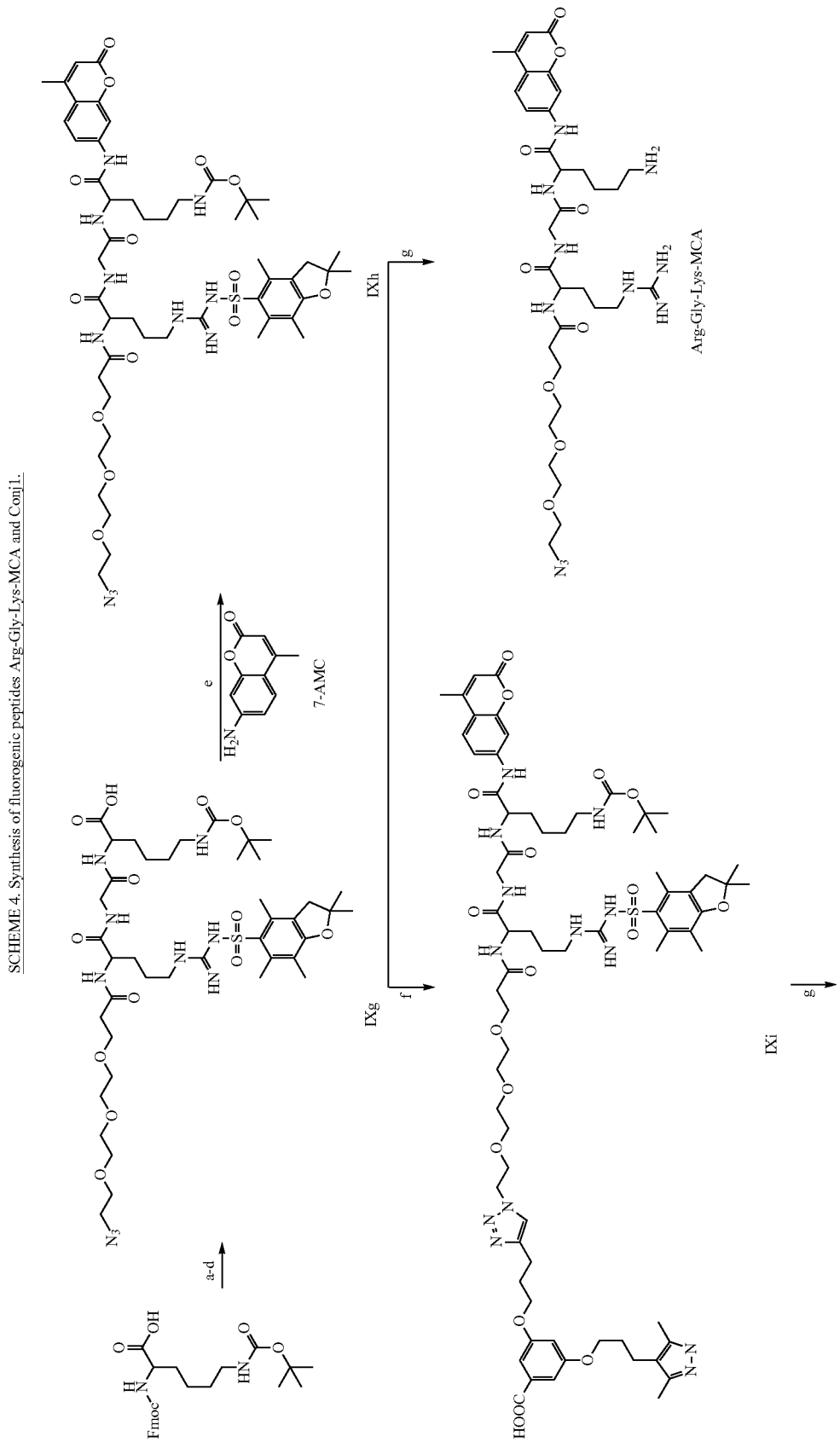

-continued
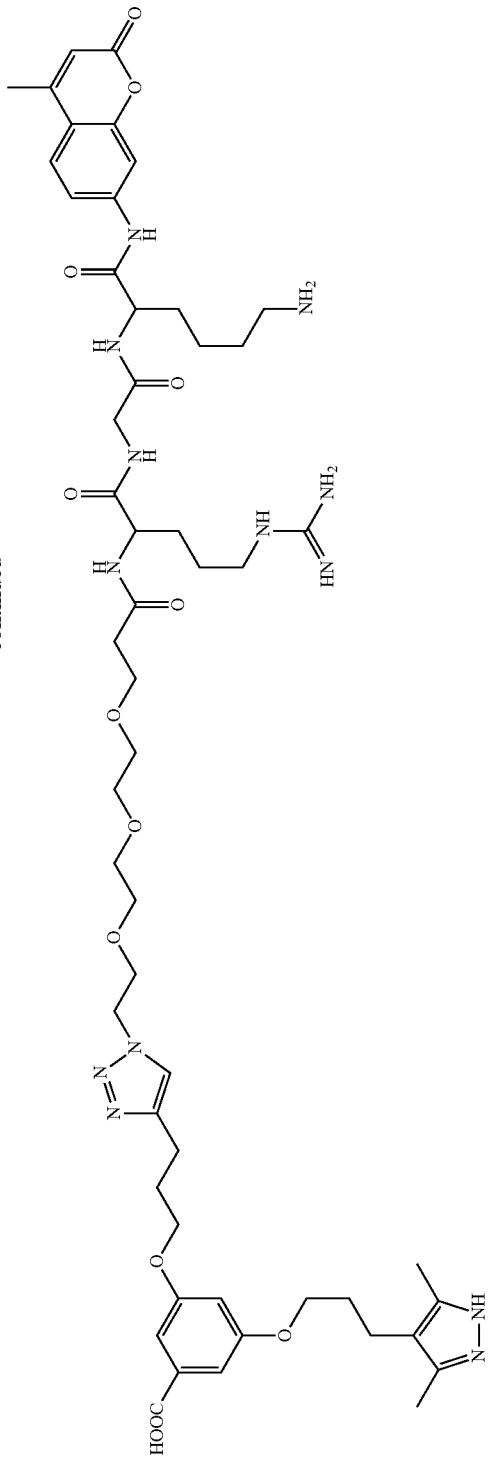
Conj1
Reagents and conditions: a) 2-Chlorotrityl chloride polystyrene resin, DIPEA, DCM, 16 h; b) Fmoc SPPS; c) Linker VIII d coupling; d) 1% TFA in DCM 10 min 4X; e) HATU, DIPEA, DMF, rt, 16 h; f) TLHEt, CuI, DIPEA, DMF, rt, 20 h; g) 95% TFA/water, 2 h.

Synthesis of Fluorogenic Compounds Arg-Gly-Lys-MCA and Conj1

The synthesis of Arg-Gly-Lys-MCA and Conj1 was carried out by employing standard Fmoc/Boc protocols using solid phase synthesis (SCHEME 4). The synthesis was carried out on a 2-chlorotrityl resin (resin loading, 1.6 mmol/g) which was swollen in dichloromethane (DCM) for ~30 min. For the resin loading step, the resin (312.5 mg, 0.5 mmol) was reacted with Fmoc-Lys(Boc)-OH (1171.5 mg, 2.5 mmol) in DCM (3 ml) and N,N-Diisopropylethylamine (DIPEA) (0.827 ml, 5 mmol). The reaction mixture was shaken overnight at room temperature. After the Lys amino acid is loaded to the resin, the un-reacted sites of the resin were end-capped with HPLC grade MeOH (0.6 ml) in a solution of DCM (5 ml) and DIPEA (0.4 ml) for 30 min. The resin was then washed to remove any remaining MeOH and DIPEA. The Fmoc group of Lys was deprotected using 2×3 ml 20% piperidine in DMF for 30 min. The loaded resin was reacted with Fmoc-Gly-OH (336.6 mg, 1.13 mmol) in DMF (3 ml) preactivated with 1-Hydroxybenzotriazole (HOBt; 153.2 mg, 1.13 mmol), 2-(1H-7-azabenzotriazol-1-yl)-1,1,3,3-tetramethyluronium hexafluorophosphate methan-aminium (HATU; 430.5 mg, 1.13 mmol) and DIPEA (0.375 ml, 2.26 mmol). The resin-bound dipeptide was Fmoc deprotected and then reacted for 2 h at rt with Fmoc-Arg (Pbf)-OH (735 mg, 1.13 mmol) in DMF (3 ml) preactivated with HOBt (153.2 mg, 1.13 mmol), HATU (430.5 mg, 1.13 mmol) and DIPEA (0.375 ml, 2.26 mmol). The coupling and deprotection reactions were monitored by performing the Kaiser test (i.e. deprotection of Fmoc group lead to a positive Kaiser test, indicated by the development of a purple color, while completion of coupling yielded a negative test, indicated by a yellow color). The resin-bound tripeptide was Fmoc deprotected followed by acetylation of the N-terminus with azide linker VIIId (343 mg, 1.13 mmol) in DMF (3 ml) preactivated with HOBt (153.2 mg, 1.13 mmol), HATU (430.5 mg, 1.13 mmol) and DIPEA (0.375 ml, 2.26 mmol). The protected tripeptide-linker was cleaved from the support resin by treating with 1% TFA in DCM (4 ml) for 10 min and draining the solution into an ice-cooled flask containing pyridine (1 ml). The deprotection step was repeated 4 times. The combined solutions were dried and the residue was washed with hexanes to give IXg (360 mg; 76.5% yield with respect to the 2-chlorotrityl resin) [IXg: ESI-MS: calculated for $C_{41}H_{68}N_{10}O_{13}S$ $[M+H]^+$ 941.5; $[M+Na]^+$ 963.5. Found: 941.7, 963.7]. IXg (180 mg, 0.19 mmol) was conjugated to 7-AMC (34 mg, 0.19 mmol) by activating the Lys COOH group in DMF (1.5 ml) using HATU (87 mg, 0.23 mmol) and DIPEA (0.2 ml, 1.2 mmol). The reaction was stirred at room temperature overnight. The DMF was removed under reduced pressure and the crude product was purified on silica gel column using 2-10% MeOH in DCM to give IXh (97 mg, 46% yield). [IXg: ESI-MS: calculated for $C_{51}H_{75}N_{11}O_{14}S$ $[M+H]^+$ 1098.5; $[M+Na]^+$ 1120.5. Found: 1098.7, 1120.7]. IXh (61 mg, 0.056 mmol) was reacted with TLHE1 (20 mg, 0.056 mmol), CuI (27 mg), DIPEA (0.076 ml, 0.46 mmol) and DMF (2 ml). The mixture was stirred overnight at room temperature (38 mg, 39% yield). [IXi: ESI-MS calculated for $C_{71}H_{99}N_{13}O_{18}S$ $[M-H]^-$ 1452.7. Found: 1452.8]. Deprotection of IXh and IXi was performed using 95% TFA for 2 h at room temperature to give Arg-Gly-Lys-MCA and Conj1, respectively (SCHEME 4).

Arg-Gly-Lys-MCA:
yield=21 mg, 22%; HPLC (0-100% solv. B [Solv. A: 95% Water 5% Methanol 0.1% TFA; Solv. B: 95% Methanol 5% Water 0.1% TFA], $t_R$ (column) (C18)=29.9 min; $t_R$ (C4)= 21.4 min; ESI-MS: Exact mass calcd for $C_{33}H_{51}N_{11}O_9$ $[M+H]^+$746.4; $[M+Na]^+$ 768.4. Found: 746.5, 768.7]. Conj1: yield=8 mg, 20%; HPLC (0-100% solv. B [Solv. A: 95% Water 5% Methanol 0.1% TFA; Solv. B: 95% Methanol 5% Water 0.1% TFA], $t_R$ (column) (C18)=32.8 min; $t_R$ (C4)=26.5 min; ESI-MS: Exact mass calcd for $C_{53}H_{75}N_{13}O_{13}$ $[M+H]^+$ 1102.6. Found: 1102.7].

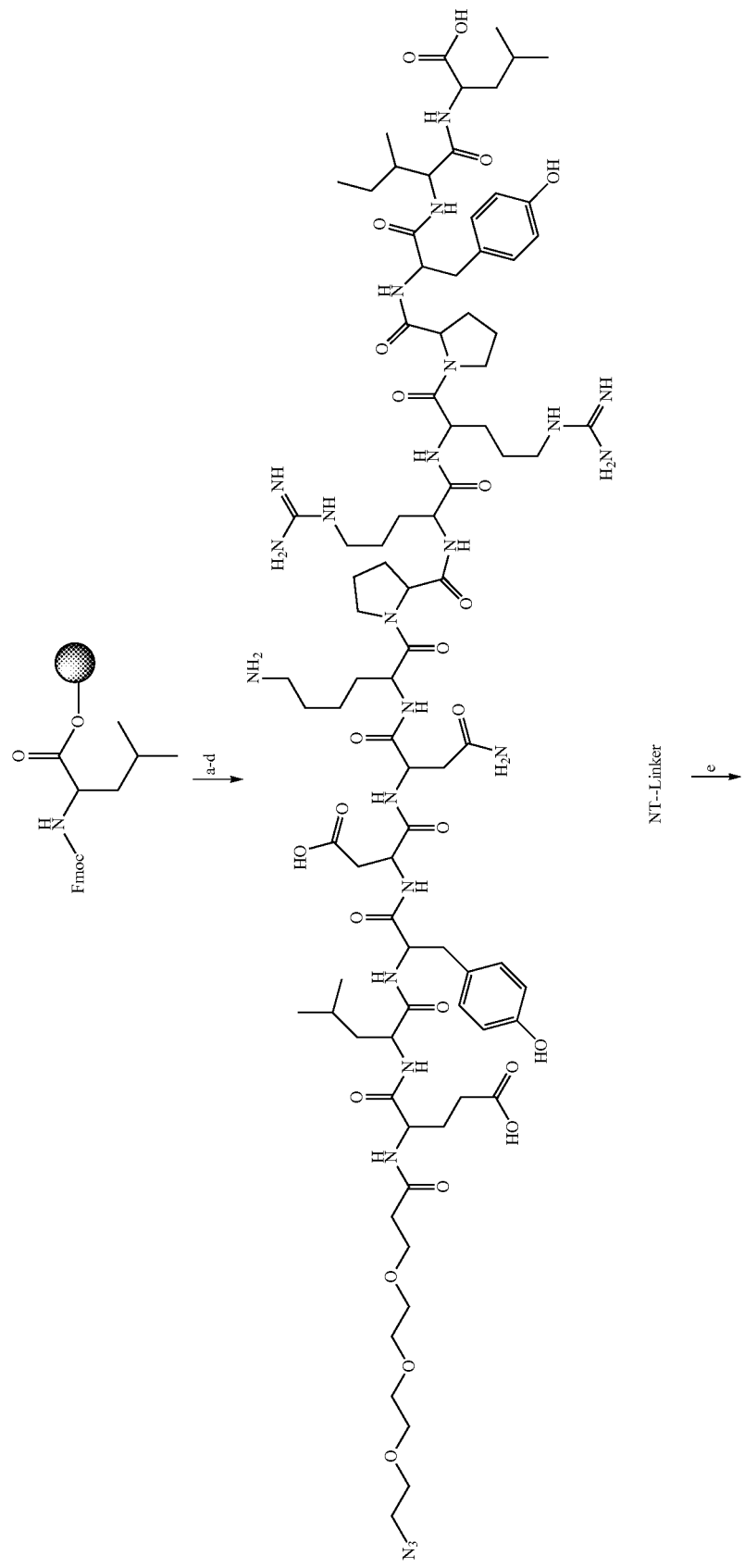
SCHEME 5. Synthesis of neurotensin (NT), NT-Linker, and Conj2.

-continued
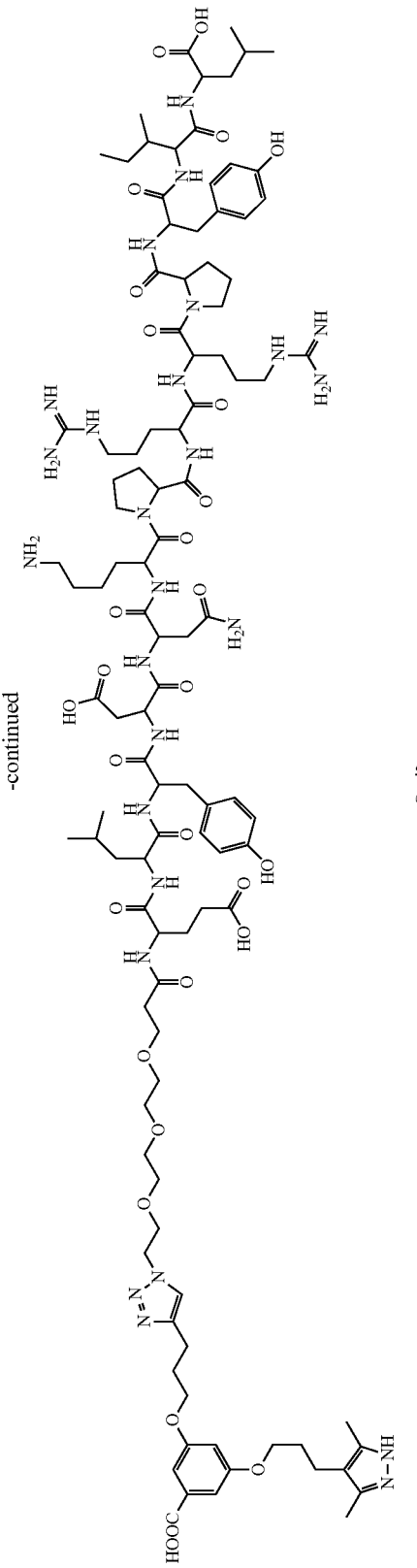
Conj2
Reagents and conditions: a) Fmoc-Leu-Wang resin; b) Fmoc SPPS (all -L-amino acids); c) Liner VIIId, HATU, HOBt, DIPEA, DMF, 24 h; d) TFA, phenol, H2O, and TIS (88:5:5:2 ratio) 3 h; e) TLHEl, CuI, sodium ascorbate, DMF/piperidine (4:1), 16 h

Synthesis of Neurotensin (NT)

The NT peptide was synthesized employing the standard Fmoc/tBu protocols using solid phase synthesis. Purification by preparative HPLC gave NT. NT: purified yield=92 mg, 58%; (97% purity by HPLC): $t_R$ (column) (C18)=21.8 min; $t_R$ (C4)=16.3 min; ESI-MS: Exact mass calcd for $C_{78}H_{122}N_{21}O_{20}$ [M+H]$^+$ 1672.9; [M+2H]$^{2+}$ 837.0; [M+3H]$^{3+}$ 558.3. Found: 1673.2, 837.5, 558.8.

Synthesis of NT-Linker

The NT peptide used was synthesized in a similar way to what is describe above for NT, expect using Glutamic acid instead of Pyroglutamic acid at the N-terminus. The azide PEG-linker (VIIId, 141 mg, 0.571 mmol) was activated with HATU (141 mg, 0.571 mmol), HOBt (77 mg, 0.571 mmol), and DIPEA (126 µL, 0.76 mmol) in DMF (3 ml) before adding to the NT-conjugated resin (0.19 mmol). The reaction mixture was shaken for 20 h. The product was then cleaved from the resin and deprotection of side chain groups was performed by treating with a cleavage cocktail, containing TFA, phenol, deionized water and TIS (88:5:5:2 ratio). Purification by preparative HPLC gave NT-Linker. NT-Linker: purified yield=170 mg, 47%; (99% purity by HPLC): $t_R$ (column) (C18)=23.2 min; $t_R$ (C4)=17.7 min; ESI-MS: Exact mass calcd for $C_{87}H_{139}N_{24}O_{25}$ [M+H]$^+$ 1920.0; [M+2H]$^{2+}$ 960.5; [M+3H]$^{3+}$ 640.7. Found: 1920.2, 961.0, 641.0.

Synthesis of Conj2

The click (CuAAC) reaction was carried out by reacting NT-Linker (17.3 mg, 0.009 mmol) with TLHE1 (10 mg, 0.028 mmol), CuI (8 mg, 0.042 mmol), and sodium ascorbate (8.4 mg, 0.042 mmol) DMF/piperidine (4:1) (0.5 ml). The mixture was shaken at room temperature for 16 h. The product (Conj2) was purified by preparative HPLC. Conj2: purified yield=4.5 mg, 22%; (99% purity by HPLC): $t_R$ (column) (C18)=26 min; $t_R$ (C4)=18.4 min; ESI-MS: Exact mass calcd for $C_{107}H_{163}N_{26}O_{29}$ [M+H]$^+$ 2276.2; [M+2H]$^{2+}$ 1139.1; [M+3H]$^{3+}$ 759.7. Found: 1139.7, 760.1.

SCHEME 6. Synthesis of GnRH-Linker, and Conj3. Reagents and conditions: a) Rink amide resin, DIPEA, DCM, 16 h; b) Fmoc SPPS (all L-amino acids); c) Linker VIIId, HATU, HOBt. DIPEA, DMF, 24 h; d) TLHE1, CuI. sodium ascorbate, DMF/piperidine (4:1), 16 h; e) TFA, phenol, H$_2$O, and TIS (88:5:5:2 ratio) 3 h.

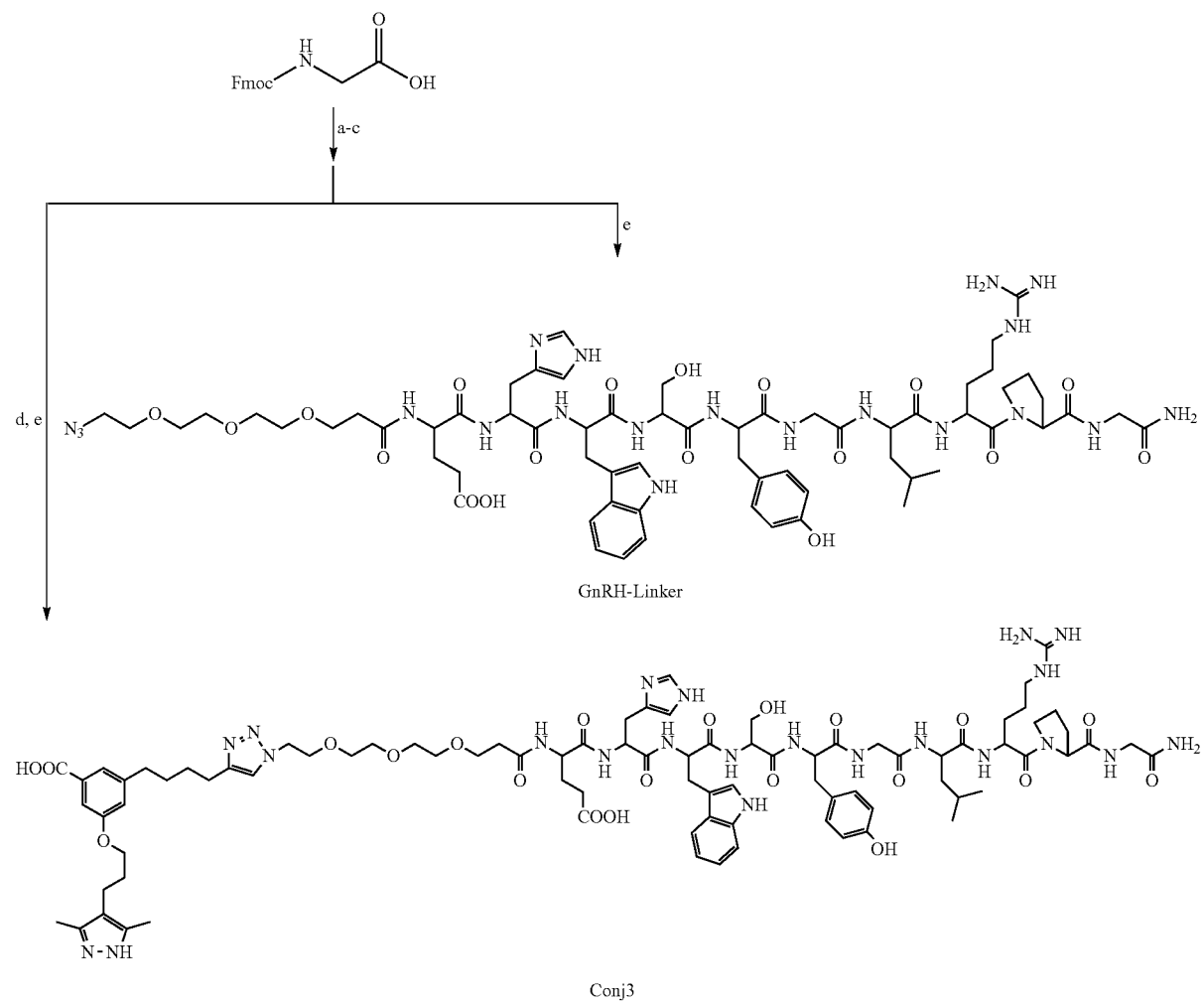

Synthesis of GnRH

The GnRH was synthesized employing the standard Fmoc/tBu protocols using solid phase synthesis. The synthesis was carried out on a Rink amide MBHA resin (Novobiochem #855003, 0.79 mmol/g). Once the GnRH decapeptide synthesis was completed, it was cleaved from the resin and deprotection of side chain groups was performed by treating with a cleavage cocktail, containing TFA, phenol, deionized water and TIS (88:5:5:2 ratio). After cleavage, the resulting peptide was precipitated by collecting onto cold ether and washed again with ether. Then, the precipitate was separated by centrifugation, dissolved in water, lyophilized. Purification by preparative HPLC gave GnRH. GnRH: (98% purity by HPLC): $t_R$ (column) (C18)=28.3 min; $t_R$ (C4)=20.2 min; ESI-MS: Exact mass calcd for $C_{55}H_{75}N_{17}O_{13}$ [M+H]$^+$ 1182.6; [M+2H]$^{2+}$ 591.8. Found: 1182.9, 592.2.

Synthesis of GnRH-Linker

The GnRH peptide used was synthesized in a similar way to what is describe above for GnRH, expect using Glutamic acid instead of Pyroglutamic acid at the N-terminus. The azide PEG-linker (2, 130 mg, 0.526 mmol) was activated with HATU (130 mg, 0.526 mmol), HOBt (71 mg, 0.526 mmol), and DIPEA (116 µL, 0.70 mmol) in DMF (2 ml) before adding to the GnRH-conjugated resin (0.175 mmol). The reaction mixture was shaken for 20 h. The product was then cleaved from the resin and deprotection of side chain groups was performed by treating with a cleavage cocktail, containing TFA, phenol, deionized water and TIS (88:5:5:2 ratio). After cleavage, the resulting peptide was precipitated by collecting onto cold ether and washed again with ether. Then, the precipitate was separated by centrifugation, dissolved in water, lyophilized. Purification by preparative HPLC gave GnRH-Linker. GnRH-Linker: purified yield=77 mg, 31%; (97% purity by HPLC): $t_R$ (column) (C18)=33.8 min; $t_R$ (C4)=26.2 min; ESI-MS: Exact mass calcd for $C_{64}H_{92}N_{20}O_{18}$ [M+H]$^+$ 1429.6; [M+2H]$^{2+}$ 715.3. Found: 1429.5, 715.6.

Synthesis of Conj3

The click (CuAAC) reaction was carried out by reacting resin bound GnRH-Linker (0.044 mmol) with TLHE1 (47 mg, 0.13 mmol), CuI (42 mg, 0.22 mmol), and sodium ascorbate (43.6 mg, 0.22 mmol) DMF/piperidine (4:1) (0.5 ml). The mixture was shaken at rt for 16 h. The product was then cleaved from the resin and deprotection of side chain groups was performed by treating with a cleavage cocktail, containing TFA, phenol, deionized water and TIS (88:5:5:2 ratio). After cleavage, the resulting peptide was precipitated by collecting onto cold ether and washed again with ether. Then, the precipitate was separated by centrifugation, dissolved in water, lyophilized. Purification by preparative HPLC gave Conj3. Conj3: purified yield=19.6 mg, 25%; (95.3% purity by HPLC): $t_R$ (column) (C18)=35.5 min; $t_R$ (C4)=29.3 min; ESI-MS: Exact mass calcd for $C_{84}H_{116}N_{22}O_{22}$ [M+H]$^+$ 1785.9; [M+2H]$^{2+}$ 893.4. Found: 1786.0, 893.7.

SCHEME 7. Synthesis of GnRH-A, GnRH-A-Linker, and Conj4. Reagents and conditions: a) Rink amide resin, DIPEA, DCM, 16 h; b) Fmoc SPPS (all L-amino acids except D-Lys); c) TFA, phenol, H$_2$O, and TIS (88:5:5:2 ratio) 3 h; d) Linker VIIId NHS, triethylamine, DMF, 24 h; e) GnRH-A-linker, TLHE1, CuI, sodium ascorbate, DMF/piperidine (4:1), 16 h.

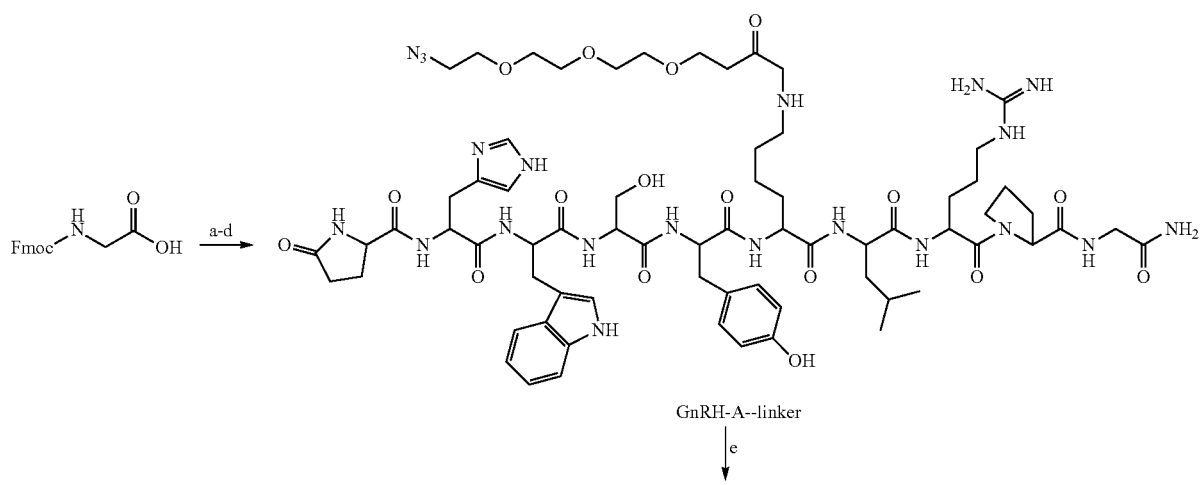

-continued

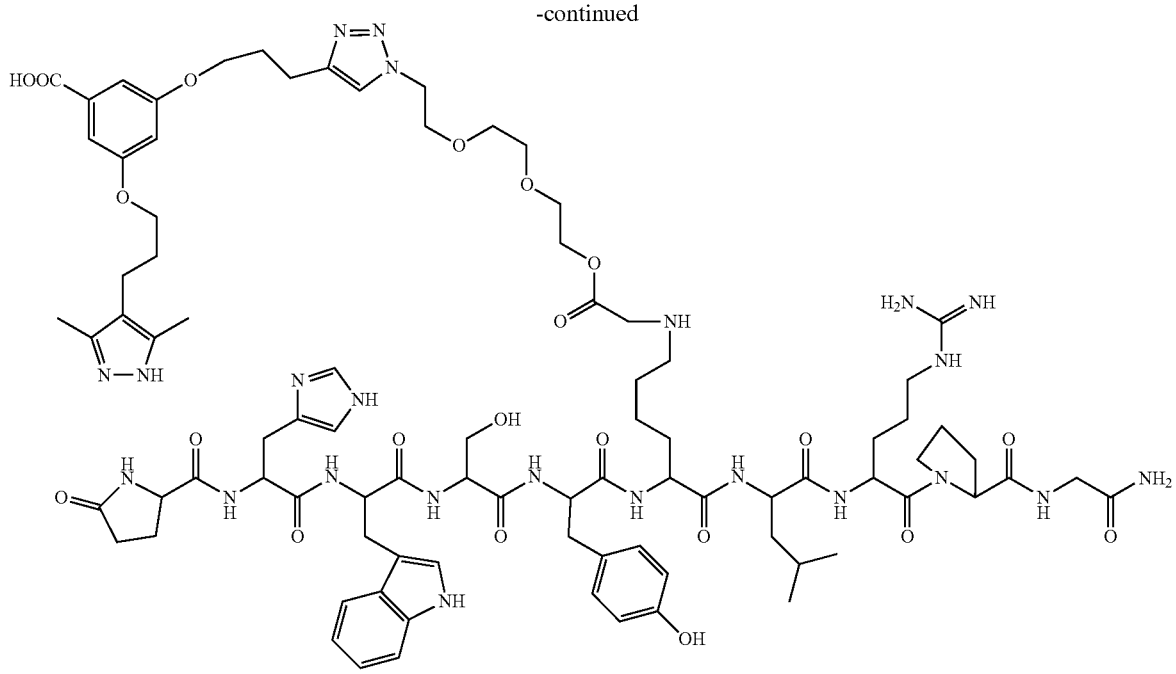

Conj4

Synthesis of GnRH-A

The GnRH peptides were synthesized employing the standard Fmoc/tBu protocols using solid phase synthesis. The synthesis was carried out on a Rink amide MBHA resin (Novobiochem #855003, 0.79 mmol/g). For the resin loading step, the resin (250 mg, 0.175 mmol) was reacted with Fmoc-Gly-OH (260 mg, 0.875 mmol) in DMF (3 ml) and N,N'-Diisopropylcarbodiimide (DIC) (0.137 ml, 0.875 mmol). The reaction mixture was shaken for 5 h, rt. The peptide was built by coupling Fmoc protected (L)-amino acid monomers (except D-Lys6) to the rink amide resin using DIC and HOBT, in DMF and shaking for 2 h. Once the GnRH deca-peptide synthesis was completed, it was cleaved from the resin and deprotection of side chain groups was performed by treating with a cleavage cocktail, containing TFA, phenol, deionized water and TIS (88:5:5:2 ratio). After cleavage, the resulting peptide was precipitated by collecting onto cold ether and washed again with ether. Then, the precipitate was separated by centrifugation, dissolved in water and lyophilized to give (D-Lys6)-GnRH (GnRH-A). [D-Lys$^6$]-GnRH (GnRH-A): purified yield=133.7 mg, 61%; (97.9% purity by HPLC): $t_R$ (column) (C18)=28.9 min; $t_R$ (C4)=19.5 min; ESI-MS: Exact mass calcd for $C_{59}H_{84}N_{18}O_{13}$ [M+H]$^+$ 1253.7; [M+2H]$^{2+}$ 627.3. Found: 1253.9, 627.7.

Synthesis of GnRH-A-Linker

The azide PEG-linker (VIIId, 119 mg, 0.48 mmol) was activated with NHS (70 mg, 0.6 mmol), DMAP (10 mg, 0.08 mmol), and DCC (600 μL of 1M solution in dichloromethane) in DMF (5 ml) for 20 h. Purification by flash silica gel chromatography gave (2-NHS) which was used directly. The linker was conjugated to the ε-amino group of lysine in GnRH-A (300 mg, 0.24 mmol) by reaction with VIIId-NHS (165 mg, 0.48 mmol) and trimethylamine (37 μL, 0.26 mmol) in DMF (3 ml). Purification by preparative HPLC gave GnRH-A-linker. GnRH-A-Linker: purified yield=126 mg, 37%; (97.2% purity by HPLC): $t_R$ (column) (C18)=33.9 min; $t_R$ (C4)=26.5 min; ESI-MS: Exact mass calcd for $C_{68}H_{99}N_{21}O_{17}$ [M+H]$^+$ 1482.7; [M+2H]$^{2+}$ 741.8. Found: 1482.5, 742.1.

Synthesis of Conj4

The click (CuAAC) reaction was carried out by reacting GnRH-A-Linker (60 mg, 0.04 mmol) with TLHE1 (43 mg, 0.12 mmol), CuI (38 mg, 0.2 mmol), and sodium ascorbate (39.6 mg, 0.2 mmol) DMF/piperidine (4:1) (0.5 ml). The mixture was shaken at room temperature for 16 h. The product (Conj4) was purified by preparative HPLC and analyzed as described above for GnRH-A-Linker. Conj4: purified yield=24 mg, 34%; (98.1% purity by HPLC): $t_R$ (column) (C18)=35.2 min; $t_R$ (C4)=29.4 min; ESI-MS: Exact mass calcd for $C_{88}H_{125}N_{23}O_{21}$ [M+H]$^+$ 1840.9; [M+2H]$^{2+}$ 920.9. Found: 1839.3, 920.6.

Synthesis of TLHE1-Small Molecule Drug Conjugate (Conj5)

Linker modified SN-38 was coupled to TLHE1 as described in FIG. 13. To a suspension of SN38 (Mwt: 392, 49.36 mg, 0.1259 mmoles) in 3 mL of anhydrous DCM were added di-tert-butyl dicarbonate (165 uL, 1.3 eq) and anhydrous pyridine (250 uL, 24 eq). The suspension was stirred o/n at RT. The solution was then filtered and washed with 0.5 N HCl (3×10 mL) and saturated NaHCO$_3$ (1×10 mL). The organic phase was separated and dried over anhydrous sodium sulfate, filtered, and evaporated under vacuum pressure to yield VIIIe (51.72 mg, 83% yield). MS confirmed [M+H]$^+$ : 492. To a solution of VIIIe (Mwt: 492, 48.5 mg, 0.09857 mmol) in 2 mL of anhydrous DCM, PEG-linker (32.66 mg, 1.34 eq), EDC (29.5 mg, 1.56 eq), DMAP (3.7 mg, 0.31 eq) were added and stirred for 3 hours. The reaction mixture was washed with 1% NaHCO$_3$ (2×10 mL), water (1×10 mL), and 0.1 N HCl (2×10 mL). The organic phase was separated and dried over NaSO$_4$, filtered, and evaporated under vacuum pressure to yield VIIIf (Mwt: 721, 36 mg, 50.6% yield). MS confirmed [M+H]$^+$ : 722.1. To a solution of VIIIf (Mwt: 721, 10 mg, 0.0138 mmol) and TLHE1 (Mwt: 356, 5 mg, 0.014 mmol) in 2 mL of anhydrous THF were added sodium ascorbate (0.8 mg, 0.3 eq) and copper sulfate (0.35 mg, 0.1 eq) in H$_2$O (0.5 mL). The solution was evaporated fully under vacuum pressure and purified via preparative HPLC to yield VIIIg (13 mg, 86.6% yield). MS confirmed [M+H]$^+$: 1078.5. To VIIIg (Mwt: 1078, 10 mg, 0.009 mmol) was added 20% TFA in DCM and stirred for 3 hours. The solution was then evaporated under vacuum pressure to yield Conj5 (8.5 mg, 93.7% yield). MS (ESI$^+$) m/z: found for C$_{51}$H$_{59}$N$_7$O$_{13}$ [M+H]$^+$: 978.4.

Chemical Synthesis of TLHE1-Imaging Agents Conjugates (Conj6 to Conj10):

Conj6, Conj7, Conj8, Conj9, and Conj10 (FIG. 11) were synthesized using Click chemistry. Linker modified Fluoresent dyes were coupled to TLHE1 similar to what is described in Scheme 1 (FIG. 12). The solution was evaporated under vacuum pressure and the resulting mixture was purified by HPLC and concentrated to yield the final product. The products were confirmed by ESI mass spectrometry. Conj6: MS (ESI$^+$) m/z: found for C$_{44}$H$_{43}$N$_7$O$_9$S [M+H]$^+$: [M+H]$^+$ (846.2). Conj7: MS (ESI$^+$) m/z: found for C$_{50}$H$_{53}$N$_7$O$_{11}$ [M+H]$^+$: [M+H]$^+$ (928.3). Conj8: MS (ESI$^+$) m/z: found for C$_{48}$H$_{47}$N$_7$O$_{11}$S [M+H]$^+$: [M+H]$^+$ (930.3). Conj9: MS (ESI$^+$) m/z: found for C$_{54}$H$_{63}$N$_8$O$_9$S [M+H]$^+$: [M+H]$^+$ (999.4). Conj10: MS (ESI$^+$) m/z: found for C$_{69}$H$_{85}$N$_8$O$_{18}$S$_4$ [M+H]$^+$: [M+H]$^+$ (1441.5).

We claim:

1. A method of administering an enhanced active agent to a subject, the method comprising: obtaining a conjugated active agent including an active agent and a delivery system for the agent, the delivery system having;

a ligand that is selective for transthyretin in the serum of the subject; and, a linker configured for operatively attaching the ligand covalently to the active agent, the linker selected to cause release of the active agent from the transthyretin in the subject as the conjugated active agent, wherein the linker ranges from 14-20 angstroms in length;

wherein, the delivery system has a structure comprising:

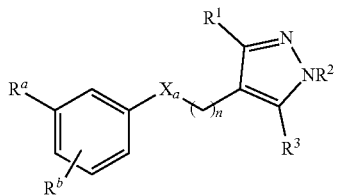

where, n is 1 to 8;

$R^1$ and $R^3$ are independently selected from a short chain alkyl having 1 to 4 carbon atoms;

$R^2$ is selected from the group consisting of a hydrogen, a short chain alkyl having 1 to 4 carbon atoms, and an aryl;

$X_a$ is $C(R^4)(R^5)$, O, N—$R^5$, or S; where $R^4$ and $R^5$ are independently selected from hydrogen, an alkyl having 1 to 4 carbon atoms, a substituted alkyl, an alkoxy, hydroxyl, an alkoxycarbonyl, an an amino;

$R^a$ is CHO, COOH, $COOCH_3$, $COOR^6$, $CONR^7R^8$, tetrazolyl, CONHOH, $B(OH)_2$, $CONHSO_2Ar$, CON-HCH($R^9$)COOH, halogen, acyl, substituted acyl, carboxyl, heterocyclic group, sulfonamide, sulfonyl fluoride, thioester, alkoxycarbonyl or substituted alkoxycarbonyl;

$R^b$ is the linker and is positioned ortho or meta to $R^a$, the linker including a CHO, COOH, $COOCH_3$, $COOR^6$, $CONR^7R^8$, tetrazolyl, CONHOH, $B(OH)_2$, $CONHSO_2Ar$, CONHCH(R)COOH, $CF_3$, hydrogen, halogen, alkyl, substituted alkyl, acyl, substituted acyl, carboxyl, heterocyclic group, sulfonamide, sulfonyl fluoride, ester, thioester, ether, thioether, triazolyl, alkoxycarbonyl or substituted alkoxycarbonyl;

$R^6$ is alkyl, haloalkyl, cycloalkyl, or heterocyclyl;

$R^7$ and $R^8$ are each independently hydrogen, alkyl, alkenyl, alkynyl, cycloalkyl, heterocyclyl, or heteroaryl; and, $R^9$ is the side chain of a naturally occurring α-amino carboxylic acid;

or, a pharmaceutically acceptable salt, ester, enol ether, enol ester, amide, acetal, ketal, orthoester, hemiacetal, hemiketal, hydrate, solvate or prodrug thereof; and administering the conjugated active agent to the subject.

2. The method of claim 1, wherein the obtaining includes having the delivery system with a ligand with the structure of Compound (VIIIc):

(VIIIc)

or, a pharmaceutically acceptable salt, ester, enol ether, enol ester, acetal, amide, ketal, orthoester, hemiacetal, hemiketal, hydrate, solvate or prodrug thereof; and, the linker is attached to the ligand ortho at C15 to the carboxyl group at C14.

3. The method of claim 1, wherein the obtaining includes having the delivery system with a ligand with the structure of Compound (VIIIc):

(VIIIc)

or, a pharmaceutically acceptable salt, ester, enol ether, enol ester, acetal, amide, ketal, orthoester, hemiacetal, hemiketal, hydrate, solvate or prodrug thereof; and, the linker is attached to the ligand meta at C16 to the carboxy carbon at C14.

4. The method of claim 1, further comprising selecting the active agent to have a structure selected from the group consisting of a peptide, an oligopeptide, a polypeptide, a protein, an antibody, an oligonucleotide, a polynucleotide, a virus-like particle, a small molecule, an oligosaccharide, an imaging agent, and combinations thereof.

5. The method of claim 1 further comprising increasing the half-life of the active agent in blood serum after the administering.

6. The method of claim 1 further comprising reducing the immunogenicity of the active agent in blood serum after the administering.

7. The method of claim 2 further comprising increasing the half-life of the active agent in blood serum after the administering.

8. The method of claim 2 further comprising reducing the immunogenicity of the active agent in blood serum after the administering.

9. The method of claim 3 further comprising increasing the half-life of the active agent in blood serum after the administering.

10. The method of claim 3 further comprising reducing the immunogenicity of the active agent in blood serum after the administering.

11. The method of claim 4 further comprising increasing the half-life of the active agent in blood serum after the administering.

12. The method of claim 4 further comprising reducing the immunogenicity of the active agent in blood serum after the administering.

13. The method of claim 1, wherein the obtaining includes having the delivery system with the linker, $R^b$, attached (i) to the ligand through an ether bond and (ii) to the active agent through an amide bond.

14. The method of claim 1, wherein the obtaining includes having the delivery system with the linker, $R^b$, attached (i) to the ligand through an ether bond and (ii) to the active agent through an ester.

15. The method of claim 1, wherein the obtaining includes having the delivery system with
the linker, $R^b$, attached (i) to the ligand through an ether bond and (ii) to the active agent through an amide bond or an ester bond;
$R^a$ comprising a carboxy group;
$R^1$ comprising a methyl group;
$R^2$ comprising hydrogen;
$R^3$ comprising a methyl group; and,
the active agent comprising a protein or peptide.

16. The method of claim 1, further comprising selecting the active agent to be a therapeutic agent and the administering occurs before the onset of a disease.

17. The method of claim 1, further comprising selecting the active agent to be a therapeutic agent and the administering occurs at an early stage after the onset of a disease.

18. The method of claim 1, further comprising selecting the active agent to be an imaging agent.

19. The method of claim 1, further comprising selective the active agent to be a therapeutic agent and the administering occurs before the onset of a disease to at least inhibit angiogenesis.

20. The method of claim 1, further comprising selecting the active agent to be a therapeutic agent and the administering occurs at an early stage after the onset of a disease to at least inhibit angiogenesis.

* * * * *